United States Patent
Lan et al.

(10) Patent No.: US 9,867,826 B2
(45) Date of Patent: Jan. 16, 2018

(54) HETEROCYCLES AS MODULATORS OF KINASE ACTIVITY

(71) Applicant: Merck Patent GmbH, Darmstadt (DE)

(72) Inventors: Ruoxi Lan, Waltham, MA (US); Xiaoling Chen, Chestnut Hill, MA (US); Yufang Xiao, Lexington, MA (US); Bayard R. Huck, Sudbury, MA (US); Andreas Goutopoulos, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/245,481

(22) Filed: Aug. 24, 2016

(65) Prior Publication Data

US 2016/0361316 A1 Dec. 15, 2016

Related U.S. Application Data

(63) Continuation of application No. 14/775,205, filed as application No. PCT/US2014/022479 on Mar. 10, 2014.

(60) Provisional application No. 61/776,440, filed on Mar. 11, 2013.

(51) Int. Cl.
*A61K 31/519* (2006.01)
*C07D 401/14* (2006.01)
*A61K 31/506* (2006.01)
*C07D 487/04* (2006.01)

(52) U.S. Cl.
CPC .......... *A61K 31/519* (2013.01); *A61K 31/506* (2013.01); *C07D 401/14* (2013.01); *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 7,754,722 B2 | 7/2010 | Magar | |
| 8,148,387 B2 | 4/2012 | Shepherd | |
| 8,334,293 B2 | 12/2012 | Geeganage | |
| 8,436,002 B2 | 5/2013 | Beight | |
| 9,139,568 B2 | 9/2015 | Huck | |
| 9,145,392 B2 | 9/2015 | Lan | |
| 9,458,134 B2 * | 10/2016 | Lan | C07D 401/14 |
| 2010/0093748 A1 | 4/2010 | Woodhead | |
| 2010/0120801 A1 * | 5/2010 | Shepherd | C07D 487/04 514/265.1 |
| 2011/0212977 A1 | 9/2011 | Geeganage | |
| 2013/0023522 A1 | 1/2013 | Yu | |
| 2013/0217709 A1 | 8/2013 | Huck | |
| 2014/0128390 A1 | 5/2014 | Lin | |
| 2014/0162983 A1 | 6/2014 | Hodous | |
| 2014/0343029 A1 | 11/2014 | Lan | |
| 2015/0126484 A1 | 5/2015 | Lan | |
| 2015/0225371 A1 | 8/2015 | Lan | |
| 2015/0239902 A1 | 8/2015 | Lan | |
| 2015/0284397 A1 | 10/2015 | Lin | |

FOREIGN PATENT DOCUMENTS

| | | |
|---|---|---|
| WO | 2003/064397 A1 | 8/2003 |
| WO | 2004/092154 A1 | 10/2004 |
| WO | 2005/033086 A1 | 4/2005 |
| WO | 2005/039506 A2 | 5/2005 |
| WO | 2005/054237 A1 | 6/2005 |
| WO | 2005/056014 A1 | 6/2005 |
| WO | 2005/117909 A2 | 12/2005 |
| WO | 2006/120573 A2 | 5/2006 |
| WO | 2006/071819 A1 | 7/2006 |
| WO | 2006/131835 A2 | 12/2006 |
| WO | 2006/136821 A1 | 12/2006 |
| WO | 2008/075109 A1 | 6/2008 |
| WO | 2008/140947 A1 | 11/2008 |
| WO | WO 2008140947 A1 * | 11/2008 |
| WO | 2010/056563 A1 | 5/2010 |
| WO | 20101056575 A1 | 5/2010 |
| WO | 2010/093419 A1 | 8/2010 |
| WO | 2011/050016 A1 | 4/2011 |
| WO | 2012/013282 A1 | 2/2012 |
| WO | 2012/016001 A1 | 2/2012 |
| WO | 2012/069146 A1 | 5/2012 |
| WO | 2013/040059 A1 | 3/2013 |

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
Barlund M. et al., Cancer Res., 2000, 60:5340-5346.
Couch et al., Cancer Res. (1999) 59: 1408-11.
Garcia-Bustos et al., EMBO J., 1994, 13(10):2352-2361.
Hanks/Hunter, FASEB J., 1995, 9:576-596.
Hardie/Hanks, The Protein Kinase Facts Book. I and II, 1995, Academic Press, San Diego, CA.
Hiles et al., Cell, 1992, 70:419-429.
Knighton et al., Science, 1991, 253:407-414.
Kunz et al., Cell, 1993, 73:585-596.
Wu et al., Cancer Res. (2000): 60: 5371-5375.

* cited by examiner

*Primary Examiner* — Alexander R Pagano
(74) *Attorney, Agent, or Firm* — Dwight D. Kim; EMD Serono Research and Development Institute

(57) ABSTRACT

The invention provides novel heterocyclic amines according to Formula (I) their manufacture and use for the treatment of hyperproliferative diseases, such as cancer.

12 Claims, No Drawings

HETEROCYCLES AS MODULATORS OF KINASE ACTIVITY

RELATED APPLICATIONS

This application is a continuation application of U.S. application Ser. No. 14/775,205, which is a U.S. national stage application of PCT international application PCT/US14/22479, filed on Mar. 10, 2014, which claims the benefit of U.S. provisional application U.S. Ser. No. 61/776,440, filed on Mar. 11, 2013. The entire contents of the aforementioned applications are hereby incorporated by reference.

FIELD OF THE INVENTION

The invention relates to a series of novel heterocyclic amines that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

BACKGROUND

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as S6K, p70/p85 S6 kinase, p70/p85 ribosomal S6 kinase and p70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumour metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumour cell proliferation and protection of cells from apoptosis is supported based on it participation in growth factor receptor signal transduction, overexpression and activation in tumour tissues. For example, Northern and Western analyses revealed that amplification of the pS6K gene was accompanied by corresponding increases in mRNA and protein expression, respectively (Cancer Res. (1999) 59: 1408-11-Localization of pS6K to Chromosomal Region 17q23 and Determination of Its Amplification in Breast Cancer).

Chromosome 17q23 is amplified in up to 20% of primary breast tumours, in 87% of breast tumours containing BRCA2 mutations and in 50% of tumours containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed. Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported. In response to energy stress, the tumour suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations. P70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140947, WO 10/056563, WO 10/093419, WO 12/013282, WO 12/016001 and WO 12/069146.

SUMMARY

In one aspect, the invention provides a compound of formula (I):

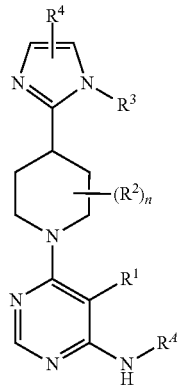

(I)

and pharmaceutically acceptable salts, solvates, solvates of salts, or prodrugs thereof, wherein each of $R^1$, $R^2$, $R^3$, $R^4$, $R^A$, and n is as defined herein.

DESCRIPTION OF THE INVENTION

It is the object of the present invention to provide novel compounds that modulate kinase activity. This protein kinase modulation includes, but is not limited to, p70S6K inhibition and Akt inhibition useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel heterocyclic amine compounds and pharmaceutically acceptable salts, solvates or prodrugs thereof, that are kinase inhibitors and useful in the treatment of the above mentioned diseases.

In one aspect, the invention provides a compound of Formula (I):

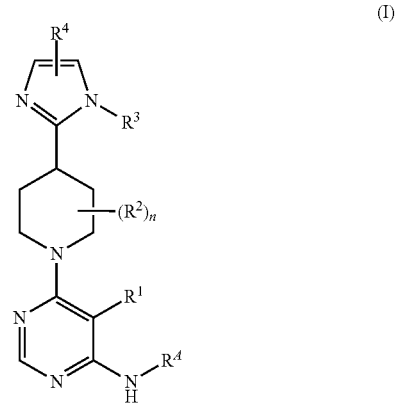

(I)

and pharmaceutically acceptable salts, solvates, solvates of salts, or prodrugs thereof, wherein:

$R^1$ is Hal, LA, OH, O(LA), $NH_2$ and/or NH(LA), $N(LA)_2$, $NO_2$, CN, OCN, COOH, COO(LA), $CONH_2$, CONH(LA), $CON(LA)_2$, NHCO(LA), NHCONH(LA), $NHCONH_2$, $NHSO_2(LA)$, CHO, CO(LA), or a mono- or bicyclic, aliphatic or aromatic homo- or heterocycle having 0, 1, 2, 3 or 4 N and/or O atoms and 4, 5 or 6, 7, 8, 9, or 10 skeleton atoms which may be unsubstituted or, independently of one another, mono-, di- or trisubstituted by Hal, LA, OH, O(LA), $NH_2$ and/or NH(LA), $N(LA)_2$, $NO_2$, CN, OCN, COOH, COO(LA), $CONH_2$, CONH(LA), $CON(LA)_2$, NHCO(LA), NHCONH(LA), $NHCONH_2$, CHO and/or CO(LA) or an unbranched or branched linear or cyclic alkyl having 1, 2, 3, 4, 5, 6, 7 or 8 C atoms, in which one or two $CH_2$ groups may be replaced by an O atom and/or by an —NH—, NH(LA), —CO—, —NHCO— or —CH=CH— group, and/or in which a CH group may be replaced by —N—;

$R^A$ is H; or $R^A$ and $R^1$, together with the atoms to which each is attached, forms a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; which is optionally substituted;

each $R^2$ is independently Hal, OH or A;

A is unbranched or branched alkyl group having 1, 2, 3, 4, 5 of 6 C atoms in which 1-4 H atoms can be replaced, independently of each other, by Hal;

$R^3$ H, or an unbranched or branched linear or mono- or bicyclic alkyl group having 1, 2, 3, 4, 5, 6, 7, 8 or 9 C atoms, in which one or two $CH_2$ groups may be replaced by an —O— or —NH— group, and/or in which one or two CH groups may be replaced by —N— and/or in which 1, 2 or 3 H atoms may be replaced by Hal or OH; or $R^3$ is unbranched or branched alkyl group having 1, 2, 3, 4, 5 of 6 C atoms, which is substituted by a 3-6 membered heterocyclic ring, which may be further optionally substituted;

$R^4$ is $C_{5-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is mono-, di- or trisubstituted by Hal, LA, OH, O(LA), NH$_2$ and/or NH(LA), N(LA)$_2$, NO$_2$, CN, OCN, COOH, COO(LA), CONH$_2$, CONH(LA), CON(LA)$_2$, NHCO(LA), NHCONH(LA), NHCONH$_2$, NHSO$_2$(LA), CHO or CO(LA);

LA is an unbranched or branched, saturated or partially unsaturated, linear hydrocarbon chain having 1, 2, 3 or 4 C atoms, wherein 1, 2 or 3 H atoms may be replaced by Hal;

Hal is F, Cl, Br or I; and n is 1 or 2.

In certain embodiments, R$^1$ is Hal, LA, OH, O(LA), NH$_2$ and/or NH(LA), N(LA)$_2$, NO$_2$, CN, OCN, COOH, COO(LA), CONH$_2$, CONH(LA), CON(LA)$_2$, NHCO(LA), NHCONH(LA), NHCONH$_2$, NHSO$_2$(LA), CHO, or CO(LA). In certain embodiments, R$^1$ is a mono- or bicyclic, aliphatic or aromatic homo- or heterocycle having 0, 1, 2, 3 or 4 N and/or O atoms and 4, 5 or 6, 7, 8, 9, or 10 skeleton atoms which may be unsubstituted or, independently of one another, mono-, di- or trisubstituted by Hal, LA, OH, O(LA), NH$_2$ and/or NH(LA), N(LA)$_2$, NO$_2$, CN, OCN, COOH, COO(LA), CONH$_2$, CONH(LA), CON(LA)$_2$, NHCO(LA), NHCONH(LA), NHCONH$_2$, CHO and/or CO(LA). In certain embodiments, R$^1$ is an unbranched or branched linear or cyclic alkyl having 1, 2, 3, 4, 5, 6, 7 or 8 C atoms, in which one or two CH$_2$ groups may be replaced by an O atom and/or by an —NH—, NH(LA), —CO—, —NHCO— or —CH=CH— group, and/or in which a CH group may be replaced by —N—;

In certain embodiments, R$^1$ is CN, CONH$_2$, Hal, O(LA), or an unbranched or branched linear or cyclic alkyl having 1, 2, 3, 4, 5, 6, 7 or 8 C atoms, in which one or two CH$_2$ groups may be replaced by an O atom and/or by an —NH—, NH(LA), —CO—, —NHCO— or —CH=CH— group, and/or in which a CH group may be replaced by —N—.

In certain embodiments, R$^1$ is methyl, ethyl, n-propyl, i-propyl, n-butyl, s-butyl, t-butyl, straight chain or branched pentyl, or straight chain or branched hexyl.

In certain embodiments, R$^1$ is selected from Table 1.

TABLE 1

Substituents for R$^1$ in Formula (I):

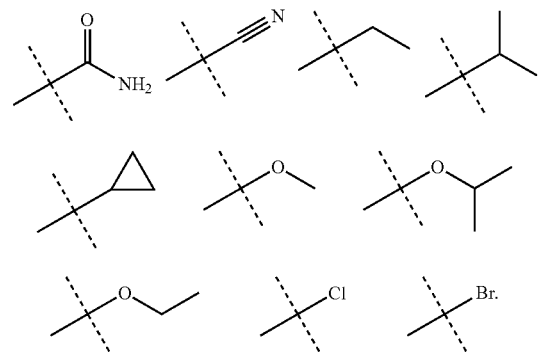

In certain embodiments, each R$^2$ is independently Hal. In certain embodiments, each R$^2$ is independently OH. In certain embodiments, each R$^2$ is independently unbranched or branched alkyl group having 1, 2, 3, 4, 5 of 6 C atoms in which 1-4 H atoms can be replaced, independently of each other, by Hal.

In certain embodiments, each R$^2$ is independently Hal, OH, methyl, ethyl, n-propyl, i-propyl, n-butyl, s-butyl, t-butyl, straight chain or branched pentyl, or straight chain or branched hexyl.

In certain embodiments, each R$^2$ is independently F, OH, or methyl.

In certain embodiments, R$^3$ is H.

In certain embodiments, R$^3$ is an unbranched or branched linear or mono- or bicyclic alkyl group having 1, 2, 3, 4, 5, 6, 7, 8 or 9 C atoms, in which one or two CH$_2$ groups may be replaced by an —O—, or —NH— group, and/or in which one or two CH groups may be replaced by —N— and/or in which 1, 2 or 3 H atoms may be replaced by Hal or OH.

In certain embodiments, R$^3$ is an unbranched or branched alkyl group having 1, 2, 3, 4, 5 of 6 C atoms, which is substituted by a 3-6 membered heterocyclic ring, which may be further optionally substituted. In certain embodiments, the substituted heterocyclic ring is aziridine, azetidine, pyrrolidine, imidazolidine, pyrazolidine, oxazolidine, isoxazolidine, thiazolidine, isothiazolidine, piperidine, morpholine, piperazine, hexahydropyrimidine, or hexahydropyridazine.

In certain embodiments, R$^3$ is selected from Table 2.

TABLE 2

Substituents for R$^3$ in Formula (I):

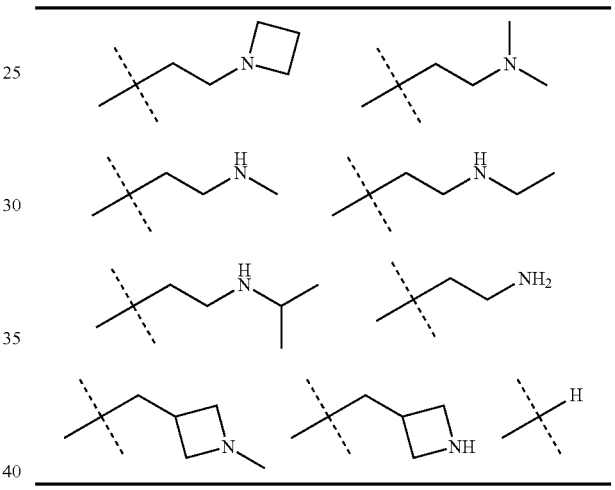

In certain embodiments, R$^4$ is C$_{5-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is mono-, di- or trisubstituted by Hal, LA, OH, O(LA), NH$_2$ and/or NH(LA), N(LA)$_2$, NO$_2$, CN, OCN, COOH, COO(LA), CONH$_2$, CONH(LA), CON(LA)$_2$, NHCO(LA), NHCONH(LA), NHCONH$_2$, NHSO$_2$(LA), CHO or CO(LA).

In certain embodiments, R$^4$ is C$_{5-10}$ aryl or a 5-6 membered monocyclic heteroaryl ring having 1-4 heteroatoms independently selected from nitrogen, oxygen, or sulfur; each of which is mono-, di- or trisubstituted by Hal, LA, OH, O(LA), NH$_2$ and/or NH(LA), N(LA)$_2$, NO$_2$, CN, OCN, COOH, COO(LA), CONH$_2$, CONH(LA), CON(LA)$_2$, NHCO(LA), NHCONH(LA), NHCONH$_2$, NHSO$_2$(LA), CHO or CO(LA).

In certain embodiments, R$^4$ is phenyl or pyridyl; each of which is mono-, di- or trisubstituted by Hal, LA, OH, O(LA), NH$_2$ and/or NH(LA), N(LA)$_2$, NO$_2$, CN, OCN, COOH, COO(LA), CONH$_2$, CONH(LA), CON(LA)$_2$, NHCO(LA), NHCONH(LA), NHCONH$_2$, NHSO$_2$(LA), CHO or CO(LA).

In certain embodiments, R$^4$ is selected from Table 3.

TABLE 3

Substituents for $R^4$ in Formula (I):

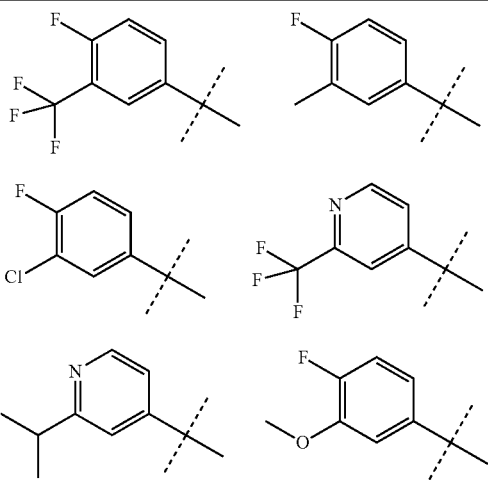

In certain embodiments, $R^4$ is H.

In certain embodiments, $R^4$ and $R^1$, together with the atoms to which each is attached, forms a 3-7 membered heterocylic ring having 1-4 heteroatoms independently selected from nitrogen, oxygen, or sulfur. In certain embodiments, $R^4$ and $R^1$, together with the atoms to which each is attached, forms a 5-6 membered monocyclic heteroaryl ring having 1-4 heteroatoms independently selected from nitrogen, oxygen, or sulfur In certain embodiments, $R^4$ and $R^1$, together with the atoms to which each is attached, forms a 5-membered heteroaryl ring; which is optionally substituted.

In certain embodiments, $R^4$ and $R^1$, together form

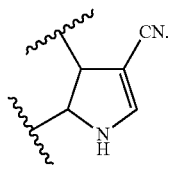

In general, all residues which occur more than once may be identical or different, i.e., are independent of one another.

In certain embodiments, the invention provides a compound of formula (II):

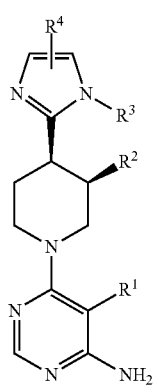

(II)

or a pharmaceutically acceptable salt thereof, wherein each of $R^1$, $R^2$, $R^3$, and $R^4$, is as defined above and described in embodiments, classes and subclasses above and herein, singly or in combination.

In certain embodiments, the compound of formula (II) is racemic. In certain embodiments, the compound of formula (II) is chiral. In certain embodiments, $R^2$ is F. In certain embodiments, $R^2$ is methyl.

In certain embodiments, the invention provides a compound of formula (III):

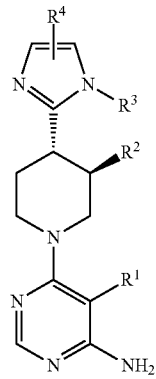

(III)

or a pharmaceutically acceptable salt thereof, wherein each of $R^1$, $R^2$, $R^3$, and $R^4$, is as defined above and described in embodiments, classes and subclasses above and herein, singly or in combination.

In certain embodiments, the compound of formula (III) is racemic. In certain embodiments, the compound of formula (III) is chiral. In certain embodiments, $R^2$ is F. In certain embodiments, $R^2$ is methyl.

In certain embodiments, the invention provides a compound of formula (IV):

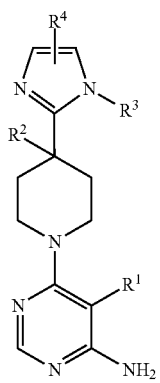

(IV)

or a pharmaceutically acceptable salt thereof, wherein each of $R^1$, $R^2$, $R^3$, and $R^4$, is as defined above and described in embodiments, classes and subclasses above and herein, singly or in combination.

In certain embodiments, $R^2$ is OH.

In certain embodiments, the invention provides a compound of formula (V):

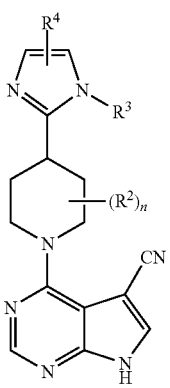

(V)

or a pharmaceutically acceptable salt thereof, wherein each of $R^2$, $R^3$, $R^4$, and n is as defined above and described in embodiments, classes and subclasses above and herein, singly or in combination.

In certain embodiments, $R^2$ is F.

In another embodiment the invention provides compounds according to Formula (I) are selected from the group consisting of:

4-Amino-6-{3,4-cis-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carbonitrile (racemic) ("1");

4-Amino-6-{3,4-cis-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carboxamide (racemic) ("2");

4-amino-6-[(3R,4S)-4-[1-[2-(azetidin-1-yl)ethyl]-4-[4-fluoro-3-(trifluoromethyl)phenyl]imidazol-2-yl]-3-fluoro-1-piperidyl]pyrimidine-5-carboxamide (chiral) ("3");

4-amino-6-[(3S,4R)-4-[1-[2-(azetidin-1-yl)ethyl]-4-[4-fluoro-3-(trifluoromethyl)phenyl]imidazol-2-yl]-3-fluoro-1-piperidyl]pyrimidine-5-carboxamide (chiral) ("4");

4-Amino-6-{3,4-cis-4-[1-(2-azetidin-1-yl-ethyl)-4-(4-fluoro-3-trifluoromethyl-phenyl)-1H-imidazol-2-yl]-3-methyl-piperidin-1-yl}-pyrimidine-5-carbonitrile (racemic) ("5");

4-Amino-6-{3,4-cis-4-[1-(2-azetidin-1-yl-ethyl)-4-(4-fluoro-3-trifluoromethyl-phenyl)-1H-imidazol-2-yl]-3-methyl-piperidin-1-yl}-pyrimidine-5-carboxamide (racemic) ("6");

4-amino-6-{3,4-trans-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carbonitrile (racemic) ("7");

4-Amino-6-{3,4-trans-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carboxamide (racemic) ("8");

4-amino-6-{3,4-cis-4-[1-(2-dimethylaminoethyl)-4-(4-fluoro-3-methyl-phenyl)imidazol-2-yl]-3-fluoro-1-piperidyl]}-pyrimidine-5-carbonitrile (racemic) ("9");

6-{3,4-cis-4-[1-(2-Azetidin-1-yl-ethyl)-4-(4-fluoro-3-trifluoromethyl-phenyl)-1H-imidazol-2-yl]-3-fluoro-piperidin-1-yl}-5-chloro-pyrimidin-4-ylamine (racemic) ("10");

6-{3,4-trans-4-[1-(2-Azetidin-1-yl-ethyl)-4-(4-fluoro-3-trifluoromethyl-phenyl)-1H-imidazol-2-yl]-3-fluoro-piperidin-1-yl}-5-chloro-pyrimidin-4-ylamine (racemic) ("11");

5-chloro-6-{3,4-cis-4-[1-(2-dimethylamino-ethyl)-4-(4-fluoro-3-methyl-phenyl)-1H-imidazol-2-yl]-3-fluoro-piperidin-1-yl}-pyrimidin-4-ylamine (racemic) ("12");

6-{3,4-cis-4-[1-(2-Azetidin-1-yl-ethyl)-4-(4-fluoro-3-trifluoromethyl-phenyl)-1H-imidazol-2-yl]-3-fluoro-piperidin-1-yl}-5-ethyl-pyrimidin-4-ylamine (racemic) ("13");

4-Amino-6-{3,4-cis-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carbonitrile (racemic) ("14");

4-Amino-6-{3,4-cis-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carbonitrile (racemic) ("15");

6-{3,4-cis-4-[1-(2-Azetidin-1-yl-ethyl)-4-(4-fluoro-3-trifluoromethyl-phenyl)-1H-imidazol-2-yl]-3-fluoro-piperidin-1-yl}-5-ethoxy-pyrimidin-4-ylamine (racemic) ("16");

6-{cis-4-[1-(2-Dimethylamino-ethyl)-4-(4-fluoro-3-trifluoromethyl-phenyl)-1H-imidazol-2-yl]-3-fluoro-piperidin-1-yl}-5-isopropyl-pyrimidin-4-ylamine (racemic) ("17");

4-Amino-6-{cis-4-[1-(2-azetidin-1-yl-ethyl)-4-(4-fluoro-3-methyl-phenyl)-1H-imidazol-2-yl]-3-fluoro-piperidin-1-yl}-pyrimidine-5-carbonitrile (racemic) ("18");

4-Amino-6-{cis-4-[1-(2-azetidin-1-yl-ethyl)-4-(4-fluoro-3-methyl-phenyl)-1H-imidazol-2-yl]-3-fluoro-piperidin-1-yl}-pyrimidine-5-carboxylic acid amide (racamic) ("19");

4-Amino-6-{(3S,4R)-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carboxylic acid amide (chiral) ("20");

4-Amino-6-{(3R,4S)-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carboxylic acid amide (chiral) ("21");

6-{(3R,4S)-4-[1-(2-Azetidin-1-yl-ethyl)-4-(4-fluoro-3-trifluoromethyl-phenyl)-1H-imidazol-2-yl]-3-fluoro-piperidin-1-yl}-5-ethoxy-pyrimidin-4-ylamine (chiral) ("22");

6-{(3S,4R)-4-[1-(2-Azetidin-1-yl-ethyl)-4-(4-fluoro-3-trifluoromethyl-phenyl)-1H-imidazol-2-yl]-3-fluoro-piperidin-1-yl}-5-ethoxy-pyrimidin-4-ylamine (chiral) ("23");

6-{cis-4-[1-(2-Azetidin-1-yl-ethyl)-4-(4-fluoro-3-methyl-phenyl)-1H-imidazol-2-yl]-3-fluoro-piperidin-1-yl}-5-isopropyl-pyrimidin-4-ylamine (racemic) ("24");

5-Chloro-6-cis-4-[1-(2-dimethylamino-ethyl)-4-(4-fluoro-3-trifluoromethyl-phenyl)-1H-imidazol-2-yl]-3-fluoro-piperidin-1-yl}-pyrimidin-4-ylamine (racemic) ("25");

6-{cis-3-Fluoro-4-[4-(4-fluoro-3-trifluoromethyl-phenyl)-1H-imidazol-2-yl]-piperidin-1-yl}-5-isopropyl-pyrimidin-4-ylamine (racemic) ("26");

4-Amino-6-{(3R,4S)-4-[1-(2-azetidin-1-yl-ethyl)-4-(4-fluoro-3-methyl-phenyl)-1H-imidazol-2-yl]-3-fluoro-piperidin-1-yl}-pyrimidine-5-carboxylic acid amide (chiral) ("27");

4-Amino-6-{(3S,4R)-4-[1-(2-azetidin-1-yl-ethyl)-4-(4-fluoro-3-methyl-phenyl)-1H-imidazol-2-yl]-3-fluoro-piperidin-1-yl}-pyrimidine-5-carboxylic acid amide (chiral) ("28");

5-Chloro-6-{(3R,4S)-4-[1-(2-dimethylamino-ethyl)-4-(4-fluoro-3-trifluoromethyl-phenyl)-1H-imidazol-2-yl]-3-fluoro-piperidin-1-yl}-pyrimidin-4-ylamine (chiral) ("29");

5-Chloro-6-{(3S,4R)-4-[1-(2-dimethylamino-ethyl)-4-(4-fluoro-3-trifluoromethyl-phenyl)-1H-imidazol-2-yl]-3-fluoro-piperidin-1-yl}-pyrimidin-4-ylamine (chiral) ("30");

6-{(3S,4R)-4-[1-(2-Dimethylamino-ethyl)-4-(4-fluoro-3-trifluoromethyl-phenyl)-1H-imidazol-2-yl]-3-fluoro-piperidin-1-yl}-5-isopropyl-pyrimidin-4-ylamine (chiral) ("31");

6-{(3R,4S)-4-[1-(2-Dimethylamino-ethyl)-4-(4-fluoro-3-trifluoromethyl-phenyl)-1H-imidazol-2-yl]-3-fluoro-piperidin-1-yl}-5-isopropyl-pyrimidin-4-ylamine (chiral) ("32");

6-{cis-4-[1-(2-Amino-ethyl)-4-(4-fluoro-3-trifluoromethyl-phenyl)-1H-imidazol-2-yl]-3-fluoro-piperidin-1-yl}-5-isopropyl-pyrimidin-4-ylamine (racemic) ("33");

6-{(3S,4R)-4-[1-(2-Azetidin-1-yl-ethyl)-4-(4-fluoro-3-methyl-phenyl)-1H-imidazol-2-yl]-3-fluoro-piperidin-1-yl}-5-isopropyl-pyrimidin-4-ylamine (chiral) ("34");

6-{(3R,4S)-4-[1-(2-Azetidin-1-yl-ethyl)-4-(4-fluoro-3-methyl-phenyl)-1H-imidazol-2-yl]-3-fluoro-piperidin-1-yl}-5-isopropyl-pyrimidin-4-ylamine (chiral) ("35");

6-{(cis-4-[1-(2-Amino-ethyl)-4-(4-fluoro-3-trifluoromethyl-phenyl)-1H-imidazol-2-yl]-3-fluoro-piperidin-1-yl}-5-chloro-pyrimidin-4-ylamine (racemic) ("36");

6-{cis-3-Fluoro-4-[4-(4-fluoro-3-methyl-phenyl)-1-(2-isopropylamino-ethyl)-1H-imidazol-2-yl]-piperidin-1-yl}-5-isopropyl-pyrimidin-4-ylamine (racemic) ("37");

6-{cis-3-Fluoro-4-[4-(4-fluoro-3-methyl-phenyl)-1-(2-methylamino-ethyl)-1H-imidazol-2-yl]-piperidin-1-yl}-5-isopropyl-pyrimidin-4-ylamine (racemic) ("38");

6-{cis-4-[1-(2-Azetidin-1-yl-ethyl)-4-(4-fluoro-3-methyl-phenyl)-1H-imidazol-2-yl]-3-fluoro-piperidin-1-yl}-5-isopropoxy-pyrimidin-4-ylamine (racemic) ("39");

4-Amino-6-{(3R,4S)-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carbonitrile (chiral) ("40");

6-{cis-4-[1-Azetidin-3-ylmethyl-4-(4-fluoro-3-methyl-phenyl)-1H-imidazol-2-yl]-3-fluoro-piperidin-1-yl}-5-isopropyl-pyrimidin-4-ylamine (racemic) ("41");

cis-4-[1-(2-Azetidin-1-yl-ethyl)-4-(4-fluoro-3-trifluoromethyl-phenyl)-1H-imidazol-2-yl]-3-fluoro-piperidin-1-yl}-7H-pyrrolo[2,3-d]pyrimidine-5-carbonitrile (racemic) ("42");

cis-4-[1-(2-Azetidin-1-yl-ethyl)-4-(2-trifluoromethyl-pyridin-4-yl)-1H-imidazol-2-yl]-3-fluoro-piperidin-1-yl}-7H-pyrrolo[2,3-d]pyrimidine-5-carbonitrile (racemic) ("43");

4-Amino-6-{4-[1-(2-azetidin-1-yl-ethyl)-4-(4-fluoro-3-methyl-phenyl)-1H-imidazol-2-yl]-4-hydroxy-piperidin-1-yl}-pyrimidine-5-carbonitrile ("44");

1-(6-Amino-5-isopropyl-pyrimidin-4-yl)-4-[1-(2-azetidin-1-yl-ethyl)-4-(4-fluoro-3-methyl-phenyl)-1H-imidazol-2-yl]-piperidin-4-ol ("45");

1-(6-Amino-5-ethyl-pyrimidin-4-yl)-4-[1-(2-azetidin-1-yl-ethyl)-4-(4-fluoro-3-methyl-phenyl)-1H-imidazol-2-yl]-piperidin-4-ol ("46");

1-(6-Amino-5-chloro-pyrimidin-4-yl)-4-[1-(2-azetidin-1-yl-ethyl)-4-(4-fluoro-3-methyl-phenyl)-1H-imidazol-2-yl]-piperidin-4-ol ("47");

4-Amino-6-{4-[1-(2-azetidin-1-yl-ethyl)-4-(4-fluoro-3-methyl-phenyl)-1H-imidazol-2-yl]-3,3-difluoro-piperidin-1-yl}-pyrimidine-5-carbonitrile ("48");

4-Amino-6-{4-[1-(2-azetidin-1-yl-ethyl)-4-(4-fluoro-3-methyl-phenyl)-1H-imidazol-2-yl]-3,3-difluoro-piperidin-1-yl}-pyrimidine-5-carboxylic acid amide ("49"); and 6-{4-[1-(2-Azetidin-1-yl-ethyl)-4-(4-fluoro-3-methyl-phenyl)-1H-imidazol-2-yl]-3,3-difluoro-piperidin-1-yl}-5-isopropyl-pyrimidin-4-ylamine ("50");

and pharmaceutically acceptable salts, solvates or prodrugs thereof.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "substituted" preferably relates to the substitution by the above-mentioned substituents, where a plurality of different degrees of substitution are possible, unless indicated otherwise.

All physiologically acceptable salts, derivatives, solvates, solvates of salts, and stereoisomers of these compounds, including mixtures thereof in all ratios, are also in accordance with the invention.

The compounds of Formula (I) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3. A method for the resolution of racemates containing ester groups (for example acetyl esters) is the use of enzymes, in particular esterases.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors. The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogenous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.2 milligrams to about 2000 milligrams, preferably from about 0.5 milligram to about 1000 milligrams. In the case of a 70 kg adult human, the total daily dose will generally be from about 0.5 milligrams to about 1000 milligrams. These aforementioned dosage regimens may be adjusted to provide the optimal therapeutic response.

The invention also relates to a set (kit) consisting of separate packs of
a) an effective amount of a compound according to the invention or a physiologically acceptable salt, solvate or prodrug thereof, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

In another embodiment the present invention describes a pharmaceutical composition or a medicament comprising a compound according to Formula (I), or a pharmaceutically acceptable salt, solvate or prodrug thereof, as active ingredient, together with a pharmaceutically acceptable carrier.

In another embodiment the present invention describes the use of a compound, pharmaceutical composition or a medicament comprising a compound according to Formula (I) for use in treating cancer.

In another embodiment the present invention describes the use of a compound, pharmaceutical composition or a medicament comprising a compound according to Formula (I) for the preparation of a medicament for the treatment of cancer.

In another embodiment the present invention describes a method for treating cancer comprising administering to a subject a compound, pharmaceutical composition or a medicament comprising a compound according to Formula (I). In certain embodiments said cancer is selected from the group consisting of brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma and Kaposi's sarcoma.

In another embodiment the present invention describes a set (kit) comprising separate packs of: a) an effective amount of a compound according to Formula (I) or a pharmaceutically acceptable salt, solvate or prodrug thereof, and b) an effective amount of a further medicament active ingredient.

Experimental Section

Some abbreviations that may appear in this application are as follows:

| Abbreviations | |
|---|---|
| Designation | |
| ACN | acetonitrile |
| AcOH | Acetic acid |
| AIBN | Azobisisobutylonitrile |
| ATP | Adenosine triphosphate |
| b | Broad peak |
| Bop-Cl | Bis(2-oxo-3-oxazolidinyl)phosphinic chloride |
| Conc. | concentrated |
| d | Doublet |
| DCM | Dichloromethane |
| DCE | dichloroethane |
| DMAP | dimethylaminopyridine |
| DMF | dimethylformamide |
| DMSO | dimethylsulfoxide |
| DIEA/DIPEA | N,N-Diisopropylethylamine |
| DTT | dithiothreitol |
| EDTA | Ethylenediaminetetraacetic acid |
| equiv./eq. | equivalents |

| Abbreviations -continued | |
|---|---|
| Designation | |
| Et | ethyl |
| h/hr | hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| LiOH | Lithium hydroxide |
| m | multiplet |
| M | Molecular ion |
| m/z | Mass-to-charge ratio |
| Me | methyl |
| MeOH | methanol |
| min | minute |
| MS | Mass spectrometry |
| N | Normal (unit of concentration) |
| NaOH | Sodium hydroxide |
| NBS | N-bromosuccinimide |
| NMO | 4-methylmorpholine N-oxide |
| NMP | N-Methyl-2-pyrrolidone |
| NMR | Nuclear Magnetic Resonance |
| PG | Protecting group |
| psi | Pounds per square inch |
| PyBOP | (Benzotriazol-1-yloxy)tripyrrolidinophosphonium hexafluorophosphate |
| q | Quartette (or quartet) |
| Rf | Retention factor |
| RT/rt | Room temperature |
| Rt. | Retention time |
| s | Singlet |
| T3P | Propylphosphonic anhydride |
| TBAF | Tetrabutylammonium fluoride |
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above.

Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formula (I) according to the hereinafter described schemes and working examples.

Synthetic Schemes Describing Intermediate and End Product Compounds

Piperidine intermediates are prepared according to the synthesis outlined in Scheme 1 and Scheme 2.

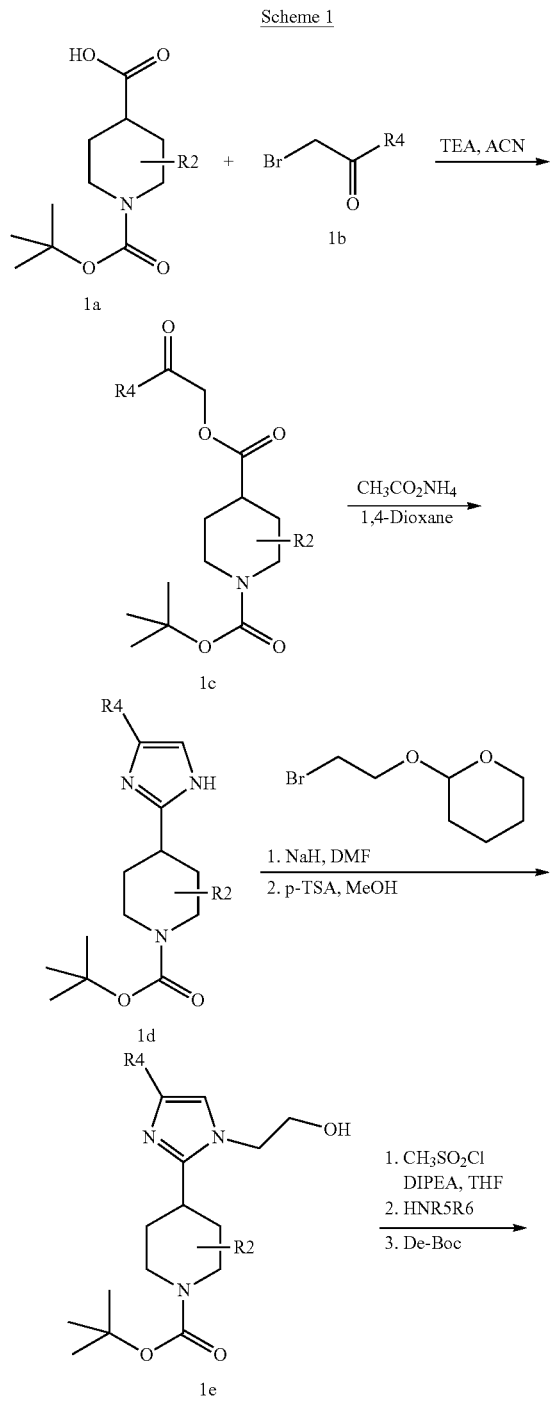

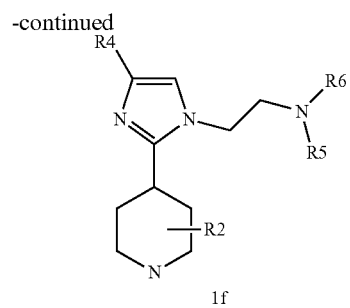

Substituted-piperidine-1,4-dicarboxylic acid 1-tert-butyl ester 1a was reacted with 1-substituted-2-bromoethanone 1b in the presence of base to provide the ester 1c, which was then reacted with ammonium acetate to yield the imidazole derivative 1d. Alkylation of 1d with 2-(2-bromo-ethoxy)-tetrahydropyran in the presence of sodium hydride in DMF, followed by deprotection with p-toluenesulfonic acid in methanol yielded the alcohol 1e. Alcohol 1e was converted to methanesulfonate intermediate and then the Boc protected amine, which was deprotected to give piperidine derivative 1f.

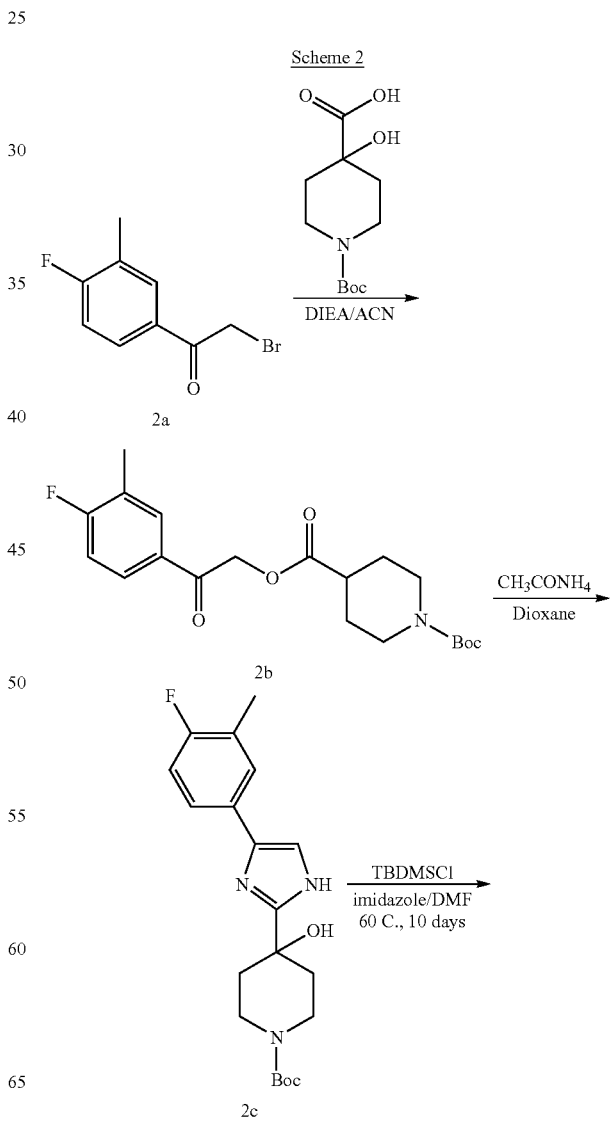

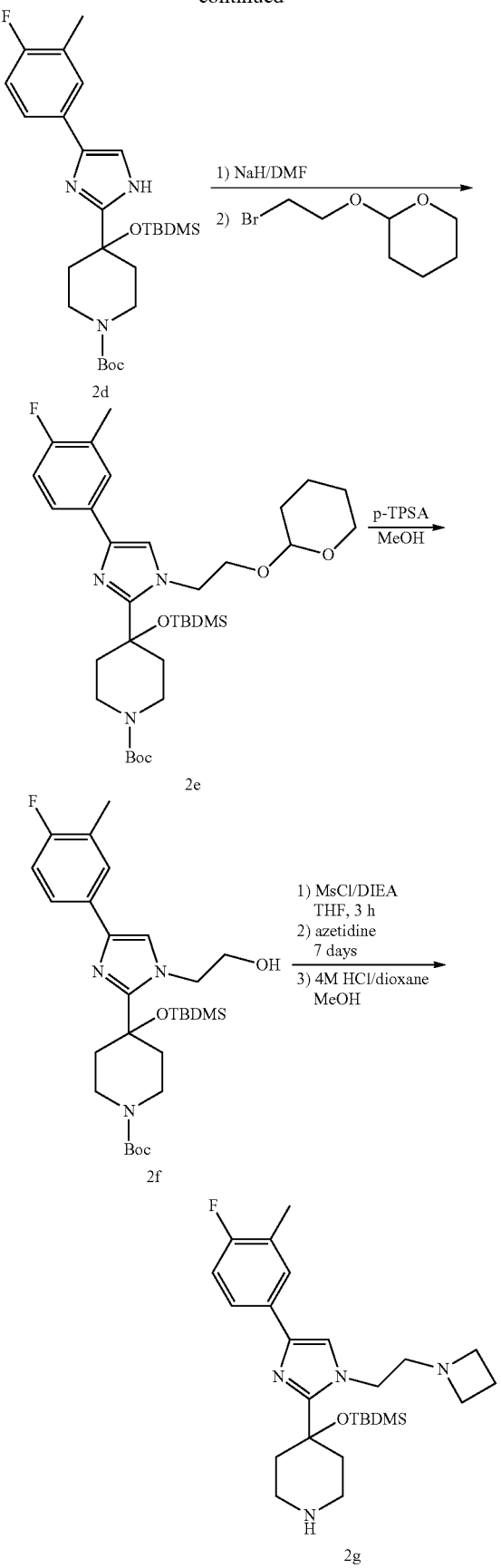

2-Bromo-1-(4-fluoro-3-methylphenyl)-ethanone 2a was reacted with 4-hydroxy-piperidine-1,4-dicarboxylic acid 1-tert-butyl ester in the presence of base to provide the ester 2b, which was then reacted with ammonium acetate to yield the imidazole derivative 2c. Protection of the hydroxyl group with TBDMSCl provided compound 2d, which was alkylated with 2-(2-bromo-ethoxy)-tetrahydropyran in the presence of sodium hydride in DMF, followed by deprotection with p-toluenesulfonic acid in methanol to yield the alcohol 2f. Alcohol 2f was converted to methanesulfonate intermediate and then the Boc protected amine, which was deprotected to give piperidine derivative 2g.

The end compounds of Formula (I) are prepared according to the synthetic route outlined in Scheme 3.

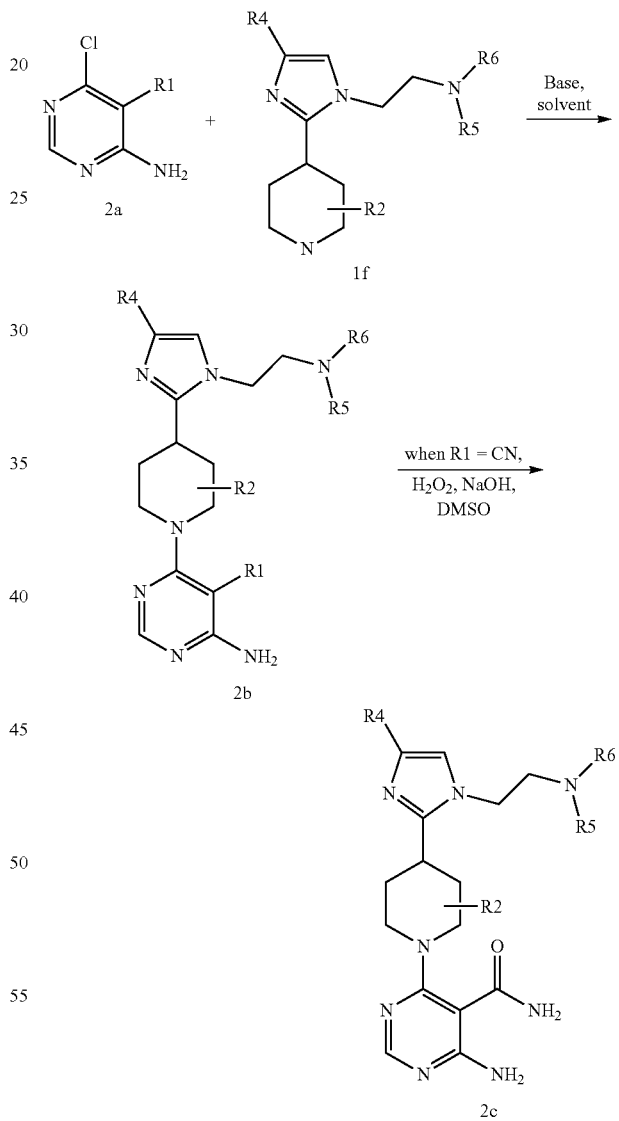

4-Amino-6-chloro-5-substituted-pyrimidine 3a was reacted with piperidine derivative under basic condition to afford the desired pyrimidine derivative 3b. 5-nitrile pyrimidine 3b (if R1=nitrile) was further converted to 5-carboxamide pyrimidine 3c with hydrogen peroxide and sodium hydroxide in DMSO.

Analytical Methodology

Analytical LC/MS was Performed Using the Following Three Methods:

Method A:

A Discovery $C^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B:

A Waters Symmetry $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C:

Gradient: 4.2 min/Flow: 2 ml/min 99:01-0:100 Water+ 0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC

Preparative HPLC was performed using either a Waters Atlantis $dC_{18}$ OBD™ 10 μM (30×250 mm) column or a Waters Sunfire Prep $C_{18}$ OBD 10 μM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

EXAMPLES

The working examples presented below are intended to illustrate particular embodiments of the invention, and are not intended to limit the scope of the specification or the claims in any way.

Example 1. Preparation of Intermediates cis-4-[1-(2-Azetidin-1-yl-ethyl)-4-(4-fluoro-3-trifluoromethyl-phenyl)-1H-imidazol-2-yl]-3-fluoropiperidine (racemic)

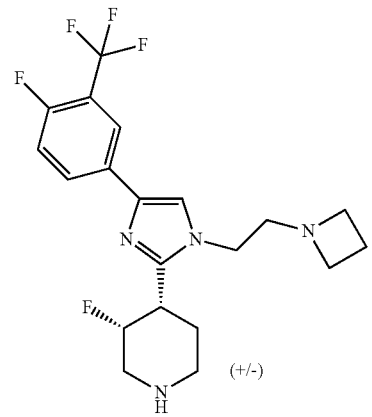 [SMILES: Fc1ccc(-c2cn(CCN3CCC3)c([C@@H]3CCNC[C@@H]3F)n2)cc1C(F)(F)F]

Step 1: 3-Fluoro-piperidine-1,4-dicarboxylic acid 1-tert-butyl ester 4-[2-(4-fluoro-3-trifluoromethyl-phenyl)-2-oxo-ethyl] ester 2-Bromo-1-(4-fluoro-3-trifluoromethyl-phenyl)-ethanone (2.23 g; 8.07 mmol; 1.0 eq.) was added to a solution of 3-fluoro-piperidine-1,4-dicarboxylic acid 1-tert-butyl ester (2.0 g; 8.07 mmol; 1.0 eq.) and triethylamine (1.36 ml; 9.68 mmol; 1.20 eq.) in acetonitrile (20 ml) at rt in one portion. The resulting mixture was stirred at rt for 1.5 h. The reaction mixture was diluted with 60 ml of ethyl acetate, washed with saturated sodium bicarbonate solution once and brine twice. The organic layer was dried over MgSO4 and then concentrated to yield the title compound as light brown solid (3.75 g, 103% yield).

Step 2: 3-Fluoro-4-[4-(4-fluoro-3-trifluoromethyl-phenyl)-1H-imidazol-2-yl]-piperidine-1-carboxylic acid tert-butyl ester A solution of 3-fluoro-piperidine-1,4-dicarboxylic acid 1-tert-butyl ester 4-[2-(4-fluoro-3-trifluoromethyl-phenyl)-2-oxo-ethyl] ester (3.60 g; 7.98 mmol; 1.0 eq.) and ammonium acetate (6.15 g; 79.75 mmol; 10.0 eq.) in 1,4-dioxane (20 ml) was stirred at 110 C. for 3 h. After cooling to rt, the reaction mixture was diluted with 100 ml of ethyl acetate, washed with saturated sodium bicarbonate once and brine twice, dry over MgSO4 and concentrated. The residue was dried in oven overnight to yield a light brown solid as the title compound (3.5 g, 102% yield), which was used for the next step without purification.

Step 3: trans-3-Fluoro-4-[4-(4-fluoro-3-trifluoromethyl-phenyl)-1-(2-hyd-roxy-ethyl)-1H-imidazol-2-yl]-piperidine-1-carboxylic acid tert-butyl ester and cis-3-Fluoro-4-[4-(4-fluoro-3-trifluoromethyl-phenyl)-1-(2-hydroxy-ethyl)-1H-imidazol-2-yl]-piperidine-1-carboxylic acid tert-butyl ester Sodium hydride (60% dispersion in mineral oil, 417.21 mg; 10.43 mmol; 3.0 eq.) was added to the solution of 3-fluoro-4-[4-(4-fluoro-3-trifluoromethyl-phenyl)-1H-imidazol-2-yl]-piperidine-1-carboxylic acid tert-butyl ester (1.50 g; 3.48 mmol; 1.0 eq.) in DMF (8.0 ml) at rt. After stirring for 30 min, 2-(2-Bromo-ethoxy)-tetrahydropyran (1.58 ml; 10.43 mmol; 3.00 eq.) was added dropwise. The resulting mixture was stirred at rt overnight. The reaction mixture was diluted with 70 ml of ethyl acetate, washed with water once and brine twice. The separated organic layer was dried over MgSO4 and concentrated to afford the crude tert-butyl 3-fluoro-4-(4-(4-fluoro-3-(trifluoromethyl)phenyl)-1-(2-((tetrahydro-2H-pyran-2-yl)oxy)ethyl)-1H-imidazol-2-yl)piperidine-1-carboxylate.

A solution of the above tert-butyl 3-fluoro-4-(4-(4-fluoro-3-(trifluoromethyl)phenyl)-1-(2-((tetrahydro-2H-pyran-2-yl)oxy)ethyl)-1H-imidazol-2-yl)piperidine-1-carboxylate and toluene-4-sulfonic acid hydrate (0.99 g, 5.22 mmole, 1.5 eq.) in methanol (10 ml) was stirred at rt for 1.5 h. After removal of the solvent, the residue was dissolved in ethyl acetate (100 ml) and saturated ammonium chloride solution (50 ml), the organic layer was washed with brine twice, dried over MgSO4 and concentrated. The crude was purified by pre-HPLC (Waters, basic condition) to yield cis-3-fluoro-4-[4-(4-fluoro-3-trifluoromethyl-phenyl)-1-(2-hydroxy-ethyl)-1H-imidazol-2-yl]-piperidine-1-carboxylic acid tert-butyl ester (440 mg, 31% yield) as the first fraction and trans-3-Fluoro-4-[4-(4-fluoro-3-trifluoromethyl-phenyl)-1-(2-hydroxy-ethyl)-1H-imidazol-2-yl]-piperidine-1-carboxylic acid tert-butyl ester (490 mg, 34% yield) as the second fraction.

Step 4: cis-4-[1-(2-Azetidin-1-yl-ethyl)-4-(4-fluoro-3-trifluoromethyl-phenyl)-1H-imidazol-2-yl]-3-fluoro-piperidine Methanesulfonyl chloride (0.07 ml; 0.95 mmol; 1.5 eq.) was added to a solution of cis-3-fluoro-4-[4-(4-fluoro-3-trifluoromethyl-phenyl)-1-(2-hydroxy-ethyl)-1H-imidazol-2-yl]-piperidine-1-carboxylic acid tert-butyl ester (300.0 mg; 0.63 mmol; 1.0 eq.) and diisopropylethylamine (0.23 ml; 1.26 mmol; 2.0 eq.) in THF (3 ml) at rt and stirred for 3 hrs. Azetidine (360 mg; 6.31 mmol; 10.0 eq.) was added to the reaction mixture and stirred at rt overnight. The reaction mixture was concentrated for the next step without purification.

The above crude compound was dissolved in a 1:1 (v/v) mixture of trifluoroacetic acid and dicholometnane (2 ml) and stirred at rt for 2 h. The reaction mixture was concentrated and purified by pre-HPLC (Waters, basic condition) to yield the title compound as off-white solid (196 mg, 75% yield).

cis-4-[1-(2-Azetidin-1-yl-ethyl)-4-(4-fluoro-3-trifluoromethyl-phenyl)-1H-imidazol-2-yl]-3-methyl-piperidine (racemic)

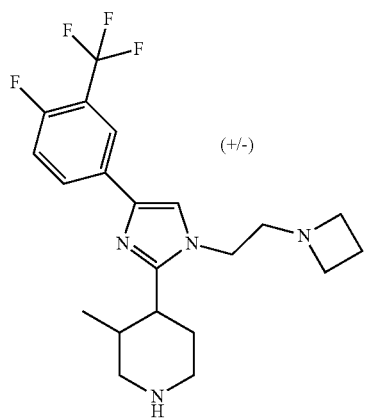 [SMILES: CC1CNCCC1c1nc(-c2ccc(F)c(C(F)(F)F)c2)cn1CCN1CCC1]

Step 1: 3-Methyl-piperidine-1, 4-dicarboxylic acid 1-tert-butyl ester 4-[2-(4-fluoro-3-trifluoromethyl-phenyl)-2-oxo-ethyl] ester To a solution of 2-bromo-1-(4-fluoro-3-trifluoromethyl-phenyl)-ethanone (1000.00 mg; 3.51 mmol; 1.00 eq.) and 3-methyl-piperidine-1,4-dicarboxylic acid 1-tert-butyl ester (981.62 mg; 4.03 mmol; 1.15 eq.) in 10 ml acetone, was added cesium carbonate (1714.6 mg; 5.26 mmol; 1.50 eq.). The resulting mixture was stirred at RT for 30 min. LC-MS showed the reaction was done with the desired product formed. The reaction solution was poured to 50 ml of ethyl acetate and washed with 5% NaHCO3 aqueous solution, then brine. The organic phase was dried and concentrated to afford the title compound, which was directly used for the next step reaction. LC-MS (M+H=448, obsd=448).

Step 2: 4-[4-(4-Fluoro-3-trifluoromethyl-phenyl)-1-(2-hydroxy-ethyl)-1H-imidazol-2-yl]-3-methyl-piperidine-1-carboxylic acid tert-butyl ester A mixture of 3-methyl-piperidine-1, 4-dicarboxylic acid 1-tert-butyl ester 4-[2-(4-fluoro-3-trifluoromethyl-phenyl)-2-oxo-ethyl] ester (1800.00 mg; 4.02 mmol; 1.00 eq.), ammonium acetate (3101.09 mg; 40.23 mmol; 10.00 eq.) and 1-butanol (3 ml) in microwave tube was placed in microwave at 125 C. for 20 min. The reaction was purified by HPLC to yield the title compound (300 mg). LC-MS (M+H=472, obsd=472).

Step 3: 4-{4-(4-Fluoro-3-trifluoromethyl-phenyl)-1-[2-(tetrahydro-pyran-2-yloxy)-ethyl]-1H-imidazol-2-yl}-3-methyl-piperidine-1-carboxylic acid tert-butyl ester To a solution of 4-[4-(4-fluoro-3-trifluoromethyl-phenyl)-1H-imidazol-2-yl]-3-methyl-piperidine-1-carboxylic acid tert-butyl ester (1000.00 mg; 2.34 mmol; 1.00 eq.) in DMF (8 ml), added NaH (280.72 mg; 7.02 mmol; 3.00 eq.). After stirring at RT for 30 mins, 2-(2-bromo-ethoxy)-tetrahydro-pyran (1467.45 mg; 7.02 mmol; 3.00 eq.) was added. The reaction mixture was stirred at 85° C. for 1 hr., LC-MS showed that the reaction was completed. The reaction mixture was cooled, poured into water, and extracted with ethyl acetate. The organic layer was washed with brine, dried and concentrated to afford the title compound, which was directly used for the next step reaction without further purification. LC-MS (M+H=556, obsd=556).

Step 4: 4-[4-(4-Fluoro-3-trifluoromethyl-phenyl)-1-(2-hydroxy-ethyl)-1H-imidazol-2-yl]-3-methyl-piperidine-1-carboxylic acid tert-butyl ester To a solution of 4-{4-(4-fluoro-3-trifluoromethyl-phenyl)-1-[2-(tetrahydro-pyran-2-yloxy)-ethyl]-1H-imidazol-2-yl}-3-methyl-piperidine-1-carboxylic acid tert-butyl ester (1290.00 mg; 2.32 mmol; 1.00 eq.) in methanol (20 ml) was added toluene-4-sulfonic acid (39.98 mg; 0.23 mmol; 0.10 eq.). The reaction mixture was stirred at RT overnight. As the LC-MS showed the starting material was major, another 2 eq of toluene-4-sulfonic acid (800 mg) was added and stirred at rt for 30 min by monitoring with LC-MS. After Removal of the solvent, 50 ml of ethyl acetate was added and washed with 10% sodium carbonate aqueous solution, then brine. The organic phase was dried and concentrated to give the crude residue, which was purified by prep HPLC to yield the title compound (200 mg, yield 18.3%). LC-MS (M+H=472, obsd=472).

Step 5: 4-[1-(2-Azetidin-1-yl-ethyl)-4-(4-fluoro-3-trifluoromethyl-phenyl)-1H-imidazol-2-yl]-3-methyl-piperidine-1-carboxylic acid tert-butyl ester To 4-[4-(4-fluoro-3-trifluoromethyl-phenyl)-1-(2-hydroxy-ethyl)-1H-imidazol-2-yl]-piperidine-1-carboxylic acid tert-butyl ester (200.00 mg; 0.44 mmol; 1.00 eq.) in THF (2 ml), was added ethyldiisopropylamine (0.16 ml; 0.87 mmol; 2.00 eq.), following by methanesulfonyl chloride (0.05 ml; 0.66 mmol; 1.50 eq.). The reaction mixture was stirred at rt overnight. LC-MS showed the formation of mesylate was completed. Azetidine (249.61 mg; 4.37 mmol; 10.00 eq.) was added and stirred at rt for 8 hr. The reaction mixture was purified by HPLC to afford the title compound (90 mg, yield 38%). LC-MS (M+H=511, obsd=511).

Step 6: 4-[1-(2-Azetidin-1-yl-ethyl)-4-(4-fluoro-3-trifluoromethyl-phenyl)-1H-imidazol-2-yl]-3-methyl-piperidine trihydrochloride To a solution of 4-[1-(2-azetidin-1-yl-ethyl)-4-(4-fluoro-3-trifluoromethyl-phenyl)-1H-imidazol-2-yl]-3-methyl-piperidine-1-carboxylic acid tert-butyl ester (70.00 mg; 0.14 mmol; 1.00 eq.) in methanol (0.5 ml), was added 4.0M HCl in dioxane 0.5 ml and, the reaction was stirred at RT for 3 hr. The reaction mixture was concentrated to give the title compound as a white solid (71.3 mg). LC-MS (M+H=411, obsd=411).

cis-4-[1-(2-Azetidin-1-yl-ethyl)-4-(4-fluoro-3-methyl-phenyl)-1H-imidazol-2-yl]-3-fluoro-piperidine (racemic)

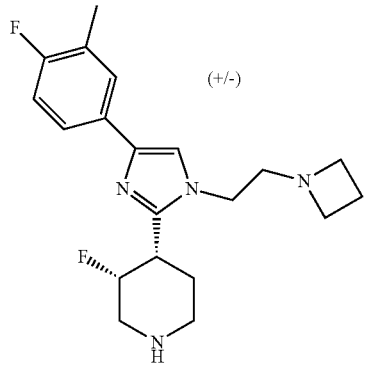 [SMILES: Cc1cc(-c2cn(CCN3CCC3)c([C@@H]3CCNC[C@@H]3F)n2)ccc1F]

Step 1: 3-Fluoro-piperidine-1,4-dicarboxylic acid 1-tert-butyl ester 4-[2-(4-fluoro-3-methyl-phenyl)-2-oxo-ethyl] ester 2-Bromo-1-(4-fluoro-3-methyl-phenyl)-ethanone (9344.79 mg; 40.44 mmol; 1.00 eq.) was added to a solution of 3-fluoro-piperidine-1,4-dicarboxylic acid 1-tert-butyl ester (10.00 g; 40.44 mmol; 1.00 eq.) and triethylamine (6.82 ml; 48.53 mmol; 1.20 eq.) in MeCN (100.00 ml; 1914.60 mmol; 47.34 eq.) at RT in one portion. The resulting mixture was stirred at RT for 2.5 h. The reaction was done by monitoring with LC-MS. The reaction mixture was diluted with 300 ml of ethyl acetate and washed with saturated aqueous NaHCO₃ once and then brine twice. The organic layer was dried over MgSO4 and concentrated. The light brown solid as the trans- and cis-mixture was used directly for the next step reaction. (14.80 g; 37.24 mmol)). LC-MS (M+H=398, obsd.=398).

Step 2: cis-3-Fluoro-4-[4-(4-fluoro-3-methyl-phenyl)-1H-imidazol-2-yl]-piperidine-1-carboxylic acid tert-butyl ester, racemic A solution of 3-fluoro-piperidine-1,4-dicarboxylic acid 1-tert-butyl ester 4-[2-(4-fluoro-3-methyl-phenyl)-2-oxo-ethyl] ester (14.80 g; 37.24 mmol; 1.00 eq.) and ammonium acetate (28706.37 mg; 372.41 mmol; 10.00 eq.) in dioxane (100.00 ml; 1173.60 mmol; 31.51 eq.) was stirred at 100° C. The reaction was completed after 2 h by monitoring with LC-MS. After cooled to RT, the reaction mixture was diluted with 300 ml of ethyl acetate, washed with saturated aqueous sodium bicarbonate twice and brine twice. The organic phase was dried over MgSO4 and concentrated. The residue (containing both trans and cis products and by-product) was dried in an oven overnight to yield a light brown solid, DCM (20 ml) was added and stirred for 10 mins, and ethyl acetate (40 ml) was added and stirred for another 1 h. The precipitate was collected by filtration and washed with small amount of ethyl acetate to yield a light yellow solid as cis-racemate product. LC-MS (M+H=378, obsd.=378).

Step 3: cis-3-Fluoro-4-[4-(4-fluoro-3-methyl-phenyl)-1-(2-hydroxy-ethyl)-1H-imidazol-2-yl]-piperidine-1-carboxylic acid tert-butyl ester, racemic To a solution of racemic cis-3-fluoro-4-[4-(4-fluoro-3-methyl-phenyl)-1H-imidazol-2-yl]-piperidine-1-carboxylic acid tert-butyl ester (5310.00 mg; 14.07 mmol; 1.00 eq.) in DMF (30 ml), was added NaH (1406.77 mg; 35.17 mmol; 2.50 eq.). After stirring at RT for 30 mins, 2-(2-Bromo-ethoxy)-tetrahydro-pyran (4.26 ml; 28.14 mmol; 2.00 eq.) was added dropwise. The reaction mixture was stirred at RT overnight. The reaction mixture was poured into water (200 ml) and extracted with ethyl acetace (200 ml×2). The combined organic layer was washed with brine, dried and concentrated to afford racemic cis-3-fluoro-4-{4-(4-fluoro-3-methyl-phenyl)-1-[2-(tetrahydro-pyran-2-yloxy)-ethyl]-1H-imidazol-2-yl}-piperidine-1-carboxylic acid tert-butyl ester. LC-MS (M+H=506, obsd.=506). To the above compound in methanol (100 ml), was added toluene-4-sulfonic acid hydrate (4014.24 mg; 21.10 mmol; 1.50 eq.). The resulting mixture was stirred at RT for 2 h. LC-MS showed the reaction was done. After removal of the solvent, the residue was diluted with ethyl acetate (200 ml), washed with 5% Na₂CO₃ aq, and then brine. The organic phase was dried and concentrated which was then treated with ether 10 ml to afford an off-white solid as the title compound (4.4 g). LC-MS (M+H=422, obsd.=422).

Step 4: cis-4-[1-(2-Azetidin-1-yl-ethyl)-4-(4-fluoro-3-methyl-phenyl)-1H-imidazol-2-yl]-3-fluoro-piperidine-1-carboxylic acid tert-butyl ester, racemic To a solution of cis-3-fluoro-4-[4-(4-fluoro-3-methyl-phenyl)-1-(2-hydroxy-ethyl)-1H-imidazol-2-yl]-piperidine-1-carboxylic acid tert-butyl ester (4400.00 mg; 10.44 mmol; 1.00 eq.) and ethyldiisopropylamine (3.75 ml; 20.88 mmol; 2.00 eq.) in THF (50 ml), was added methanesulfonyl chloride (1.21 ml; 15.66 mmol; 1.50 eq.) at 0° C. The resulting mixture was stirred at RT for 3 h. LC-MS indicated cis-3-fluoro-4-[4-(4-fluoro-3-methyl-phenyl)-1-(2-methanesulfonyloxy-ethyl)-1H-imidazol-2-yl]-piperidine-1-carboxylic acid tert-butyl ester was formed as a clean product. The reaction mixture was cooled with ice bath and azetidine (5960.26 mg; 104.39 mmol; 10.00 eq.) was added dropwise, and then stirred at RT overnight. The reaction mixture was diluted with ethyl acetate (150 ml), washed with 5% NaHCO₃ aq, and then brine. The organic phase was dried and concentrated to yield the title compound, which was used directly for the next step reaction. LC-MS (M+H=461, obsd.=461).

Step 5: cis-4-[1-(2-Azetidin-1-yl-ethyl)-4-(4-fluoro-3-methyl-phenyl)-1H-imidazol-2-yl]-3-fluoro-piperidine, racemic To a solution of cis-4-[1-(2-azetidin-1-yl-ethyl)-4-(4-fluoro-3-methyl-phenyl)-1H-imidazol-2-yl]-3-fluoro-piperidine-1-carboxylic acid tert-butyl ester (4700.00 mg; 10.20 mmol; 1.00 eq.) in methanol (15 ml), was added 4.0 M HCl in dioxane (17.86 ml; 71.43 mmol; 7.00 eq.) at 0° C. The reaction mixture was then stirred at RT for 2 h. After removal of the solvents, the residue was treated with ether to yield a light yellow solid as cis-4-[1-(2-azetidin-1-yl-ethyl)-4-(4-fluoro-3-methyl-phenyl)-1H-imidazol-2-yl]-3-fluoro-piperidine tetrahydrochloride. LC-MS (M+H=361, obsd.=361).

cis-3-[4-(4-Fluoro-3-methyl-phenyl)-2-(cis-3-fluoro-piperidin-4-yl)-imidazol-1-ylmethyl]-azetidine-1-carboxylic acid tert-butyl ester (racemic)

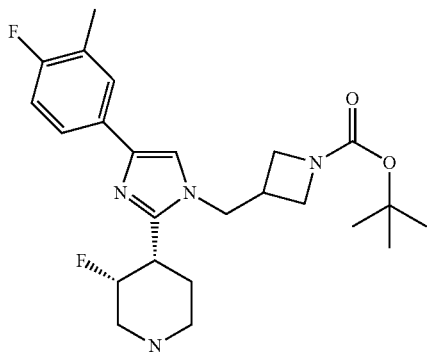 [SMILES: Cc1cc(-c2cn(CC3CN(C(=O)OC(C)(C)C)C3)c([C@@H]3CCNC[C@@H]3F)n2)ccc1F]

Step 1: cis-3-Fluoro-4-[4-(4-fluoro-3-methyl-phenyl)-1H-imidazol-2-yl]-piperidine-1-carboxylic acid benzyl ester, racemic To a solution of racemic cis-3-fluoro-4-[4-(4-fluoro-3-methyl-phenyl)-1H-imidazol-2-yl]-piperidine-1-carboxylic acid tert-butyl ester (1230.00 mg; 3.26 mmol; 1.00 eq.) in DCM (5 ml), was added trifluoroacetic acid (3715.90 mg; 32.59 mmol; 10.00 eq.). The mixture was stirred at RT for 1 hr and the LC-MS showed the reaction was complete. The reaction mixture was concentrated to yield cis-3-fluoro-4-[4-(4-fluoro-3-methyl-phenyl)-1H-imidazol-2-yl]-piperidine as TFA salt.

To a solution of the above TFA salt (2300.00 mg; 3.14 mmol; 1.00 eq.) in DCM (25 ml), were added benzyl (2,5-dioxopyrrolidin-1-yl) carbonate (1172.2 mg, 4.7 mmol; 1.5 eq.) and ethyldiisopropylamine (3.94 ml; 21.95 mmol; 7.00 eq.). The reaction mixture was stirred at RT overnight, diluted with DCM, washed with 5% NaHCO3, then Brine. The organic phase was dried and concentrated to yield the title compound, which was directly carried out for the next step reaction. LC-MS (M+H=546, obsd.=546).

Step 2: cis-4-[1-(1-tert-Butoxycarbonyl-azetidin-3-ylmethyl)-4-(4-fluoro-3-methyl-phenyl)-1H-imidazol-2-yl]-3-fluoro-piperidine-1-carboxylic acid benzyl ester, racemic To a solution of racemic cis-3-fluoro-4-[4-(4-fluoro-3-methyl-phenyl)-1H-imidazol-2-yl]-piperidine-1-carboxylic acid benzyl ester (1200.00 mg; 2.92 mmol; 1.00 eq.) in DMF (12 ml), was added NaH (349.96 mg; 8.75 mmol; 3.00 eq.). After stirring at RT for 30 min, 3-Iodomethyl-azetidine-1-carboxylic acid tert-butyl ester (1.13 ml; 5.25 mmol; 1.80 eq.) was added dropwise. The reaction mixture was stirred at RT for 2 h. The reaction was quenched with saturated aqueous NH₄Cl solution and ether acetate was added (60 ml), washed with water, 5% NaHCO3, then brine. The organic phase was dried and concentrated. The residue was purified by prep HPLC to affold the title compound. LC-MS (M+H=581, obsd.=581).

Step 3: cis-3-[4-(4-Fluoro-3-methyl-phenyl)-2-(cis-3-fluoro-piperidin-4-yl)-imidazol-1-ylmethyl]-azetidine-1-carboxylic acid tert-butyl ester, racemic To a solution of racemic cis-4-[1-(1-tert-Butoxycarbonyl-azetidin-3-ylmethyl)-4-(4-fluoro-3-methyl-phenyl)-1H-imidazol-2-yl]-3-fluoro-piperidine-1-carboxylic acid benzyl ester (120.00 mg; 0.21 mmol; 1.00 eq.) in methanol (5 ml), was added trifluoroacetic acid (47.13 mg; 0.41 mmol; 2.00 eq.). After stirring for 5 min, wet 10% Pd/C (120 mg) was added, following by ammonium formate (130.31 mg; 2.07 mmol; 10.00 eq.). The reaction mixture was stirred at 25° C. for 1 hr. After removal of catalyst and concentration, the residue was purified by prep HPLC to affold the title compound. LC-MS (M+H=447, obsd.=447).

cis-4-[1-(2-Azetidin-1-yl-ethyl)-2-(cis-3-fluoro-piperidin-4-yl)-1H-imidazol-4-yl]-2-trifluoromethyl-pyridine (racemic)

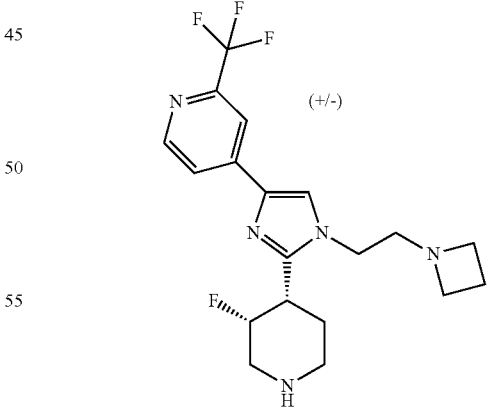

Step 1: cis-1-tert-butyl 4-{2-oxo-2-[2-(trifluoromethyl)pyridin-4-yl]ethyl} piperidine-1,4-dicarboxylate To a solution of cis-3-fluoro-piperidine-1,4-dicarboxylic acid 1-tert-butyl ester (3690.07 mg; 14.92 mmol; 1.00 eq.)

and 2-bromo-1-(2-trifluoromethyl-pyridin-4-yl)-ethanone (4000.00 mg; 14.92 mmol; 1.00 eq.) in THF (50 ml), was added ethyldiisopropylamine (5.21 ml; 29.85 mmol; 2.00 eq.) dropwise at RT. The reaction mixture was stirred at RT for another 1 hr as the LC-MS showed the reaction was complete. The reaction was quenched with saturated aqueous NH$_4$Cl solution and extracted with ethyl acetate (200 ml). The separated organic layer was washed with saturated aqueous NH$_4$Cl solution (100 ml×4), dried and concentrated to affold the title compound as yellow oil (5400 mg, 100% yield). LC-MS (M+H=435, obsd.=435).

Step 2: cis-3-Fluoro-4-[4-(2-trifluoromethyl-pyridin-4-yl)-1H-imidazol-2-yl]-piperidine-1-carboxylic acid tert-butyl ester To a solution of cis-3-fluoro-piperidine-1,4-dicarboxylic acid 1-tert-butyl ester 4-[2-oxo-2-(2-trifluoromethyl-pyridin-4-yl)-ethyl] ester (5000.00 mg; 11.51 mmol; 1.00 eq.) in dioxane (100 ml), was added ammonium acetate (8872.72 mg; 115.11 mmol; 10.00 eq.). The reaction mixture was stirred at 110° C. for 1.5 h which was monitored by LC-MS for completion. After cooled to RT, the reaction mixture was diluted with 150 ml of ethyl acetate, washed with brine, and then saturated sodium bicarbonate and brine. The organic phase was dried over MgSO4 and concentrated to give the title compound (3830 mg, yield 80.7%). LC-MS (M+H=415, obsd.=415).

Step 3: cis-3-Fluoro-4-[1-(2-hydroxy-ethyl)-4-(2-trifluoromethyl-pyridin-4-yl)-1H-imidazol-2-yl]-piperidine-1-carboxylic acid tert-butyl ester To a solution of cis-3-fluoro-4-[4-(2-trifluoromethyl-pyridin-4-yl)-1H-imidazol-2-yl]-piperidine-1-carboxylic acid tert-butyl ester (3830.00 mg; 9.24 mmol; 1.00 eq.) in DMF (18 ml), was added NaH (831.74 mg; 20.80 mmol; 2.25 eq.). After stirring at 0° C. for 30 min, 2-(2-bromo-ethoxy)-tetrahydro-pyran (2.10 ml; 13.86 mmol; 1.50 eq.) was added dropwise. The reaction mixture was stirred at RT overnight. The reaction was quenched with saturated NH$_4$Cl aqueous solution (50 ml) and extracted with ethyl acetate (100 ml×2). The combined organic layer was washed with brine, dried and concentrated. The residue was purified by Biotage (SNAP column, eluted with DCM contained 2% methanol and 0.2% TEA) to yield cis-3-fluoro-4-[1-[2-(tetrahydro-pyran-2-yloxy)-ethyl]-4-(2-trifluoromethyl-pyridin-4-yl)-1H-imidazol-2-yl]-piperidine-1-carboxylic acid tert-butyl ester (1.7 g).

To the above product dissolved in methanol (20 ml), was added toluene-4-sulfonic acid hydrate (879.03 mg; 4.62 mmol; 0.50 eq.). The reaction mixture was stirred at RT for 1 hr. After removal of the solvent, to the residue were added ethyl acetate (60 ml) and 10% Na$_2$CO$_3$ aqueous solution (20 ml) and stirred for 20 min. The separated organic layer was washed with brine, dried and concentrated to afford the title compound as a yellow solid (1300 mg, yield 30.7%). LC-MS (M+H=459, obsd.=459).

Step 4: cis-4-[1-(2-Azetidin-1-yl-ethyl)-4-(2-trifluoromethyl-pyridin-4-yl)-1H-imidazol-2-yl]-3-fluoro-piperidine-1-carboxylic acid tert-butyl ester To a solution of cis-3-chloro-4-[1-(2-hydroxy-ethyl)-4-(2-trifluoromethyl-pyridin-4-yl)-1H-imidazol-2-yl]-piperidine-1-carboxylic acid tert-butyl ester (1300.00 mg; 2.84 mmol; 1.00 eq.) and ethyl-diisopropyl-amine (0.76 ml; 4.25 mmol; 1.50 eq.) in THF (10 ml), was added methanesulfonyl chloride (0.30 ml; 3.83 mmol; 1.35 eq.) at 0° C. The reaction mixture was stirred at same temperature for 30 min and then at RT for 2 hr as the LC-MS showed the mesylation was completed. Azetidine (2.02 ml; 28.36 mmol; 10.00 eq.) was added to the above mixture and stirred at RT for 72 hr. After removal of the solvent, the residue was added 50 ml of ethyl acetate and washed with brine, 10% citric acid solution, 10% NaHCO$_3$ solution and brine. The organic phase was dried and concentrated, which was purified by SNAP column (DCM contained 1% methanol and 0.2% TEA) to the title compound. LC-MS (M+H=498, obsd.=498).

Step 5: 4-[1-(2-Azetidin-1-yl-ethyl)-2-(cis-3-fluoro-piperidin-4-yl)-1H-imidazol-4-yl]-2-trifluoromethyl-pyridine To a solution of cis-4-[1-(2-azetidin-1-yl-ethyl)-4-(2-trifluoromethyl-pyridin-4-yl)-1H-imidazol-2-yl]-3-fluoro-piperidine-1-carboxylic acid tert-butyl ester (650.00 mg; 1.31 mmol; 1.00 eq.) in methanol (3 ml), was added 4 M HCl in dioxane (2.29 ml; 9.15 mmol; 7.00 eq.) dropwise at 0° C. The reaction mixture was then stirred at RT for 2 hr as the LC-MS showed the reaction was completed. After removal of the solvents, the residue was dissolved in water (10 ml) and washed with DCM. Sodium carbonate (692.34 mg; 6.53 mmol; 5.00 eq.) and DCM (20 ml) were added to the aqueous phase and stirred at RT for 1 hr. The separated organic layer was washed with brine, dried and concentrated to affold the title compound as yellow solid (430 mg, yield 82.8%). LC-MS (M+H=398, obsd.=398).

4-[1-(2-Azetidin-1-yl-ethyl)-4-(4-fluoro-3-methyl-phenyl)-1H-imidazol-2-yl]-3,3-difluoro-piperidine

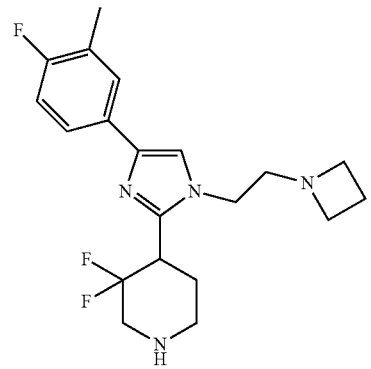 [SMILES: Cc1cc(-c2cn(CCN3CCC3)c(C3CCNCC3(F)F)n2)ccc1F]

Step 1: 3,3-Difluoro-piperidine-1,4-dicarboxylic acid 1-tert-butyl ester 4-[2-(4-fluoro-3-methyl-phenyl)-2-oxo-ethyl] ester To a solution of 3,3-Difluoro-piperidine-1,4-dicarboxylic acid 1-tert-butyl ester (3000.00 mg; 11.31 mmol; 1.00 eq.) and triethylamine (1.91 ml; 13.57 mmol; 1.20 eq.) in ACN (30 ml), was added 2-bromo-1-(4-fluoro-3-methyl-phenyl)-ethanone (2561.03 mg; 11.08 mmol; 0.98 eq.). The mixture was stirred at RT for 30 min. The reaction solution was poured to ethyl acetate (100 ml) and washed with 5% NaHCO$_3$ aq, then brine. The organic phase was dried over NaSO$_4$ and concentrated to affold the title compound. LC-MS (M+H=416, obsd=416).

Step 2: 3,3-Difluoro-4-[4-(4-fluoro-3-methyl-phenyl)-1H-imidazol-2-yl]-piperidine-1-carboxylic acid tert-butyl ester To a solution of 3,3-difluoro-piperidine-1,4-dicarboxylic acid 1-tert-butyl ester 4-[2-(4-fluoro-3-methyl-phenyl)-2-oxo-ethyl] ester (5000.00 mg; 12.04 mmol; 1.00 eq.) in dioxane (50 ml) was added ammonium acetate (9278.08 mg; 120.36 mmol; 10.00 eq.). The reaction mixture was stirred at 1101 for 2 hr, added another 2 g ammonium acetate, and stirred at 120° C. for another 1 hr. Aft er cooled to rt, the reaction mixture was poured into ethyl acetate (100 ml) and water (50 ml). The separated organic layer was washed with 5% NaHCO₃ aq, then brine, dried and concentrated to affold the title compound as a yellow solid (4796 mg, yield 92%), which was directly used for the next step reaction. LC-MS (M+H=396, obsd=396).

Step 3: 3,3-Difluoro-4-[4-(4-fluoro-3-methyl-phenyl)-1-(2-hydroxy-ethyl)-1H-imidazol-2-yl]-piperidine-1-carboxylic acid tert-butyl ester To a solution of 3,3-difluoro-4-[4-(4-fluoro-3-methyl-phenyl)-1H-imidazol-2-yl]-piperidine-1-carboxylic acid tert-butyl ester (4330.00 mg; 10.95 mmol; 1.00 eq.) in DMF (18 ml), was added NaH (1094.95 mg; 27.38 mmol; 2.50 eq.). After stirring at RT for 30 min, 2-(2-Bromo-ethoxy)-tetrahydro-pyran (3.32 ml; 21.90 mmol; 2.00 eq.) was added dropwise. The reaction mixture was stirred at RT overnight. LC-MS showed the reaction was completed. The reaction mixture was diluted with 100 ml of ethyl acetate, washed with saturate aqueous ammonium chloride and brine, dried over MgSO4 and concentrated to give the residue as 3,3-difluoro-4-{4-(4-fluoro-3-methyl-phenyl)-1-[2-(tetrahydro-pyran-2-yloxy)-ethyl]-1H-imidazol-2-yl}-piperidine-1-carboxylic acid tert-butyl ester.

The reaction mixture of the above product and toluene-4-sulfonic acid hydrate (3124.45 mg; 16.43 mmol; 1.50 eq.) in methanol (30 ml) was stirred at rt for 2 h. After removal of the solvent, the residue was dissolved in ethyl acetate, washed with 10% Na₂CO₃ aq. The organic phase was dried and concentrated. The residue was purified by prep HPLC, to affod the title compound (1190 mg, yield 24%). LC-MS (M+H=440, obsd=440).

Step 4: 4-[1-(2-Azetidin-1-yl-ethyl)-4-(4-fluoro-3-methyl-phenyl)-1H-imidazol-2-yl]-3,3-difluoro-piperidine To a solution of 3,3-difluoro-4-[4-(4-fluoro-3-methyl-phenyl)-1-(2-hydroxy-ethyl)-1H-imidazol-2-yl]-piperidine-1-carboxylic acid tert-butyl ester (1200.00 mg; 2.73 mmol; 1.00 eq.) and contained ethyl-diisopropyl-amine (0.98 ml; 5.46 mmol; 2.00 eq.) in THF, was added methanesulfonyl chloride (0.32 ml; 4.10 mmol; 1.50 eq.). The reaction mixture was stirred at RT for 3 hr and the mesylation was completed by monitoring with LC-MS. Azetidine (1.95 ml; 27.31 mmol; 10.00 eq.) was added and then stirred at RT overnight. After removal of the solvent, the residue was added DCM (5.0 ml), and then trifluoroacetic acid (3113.46 mg; 27.31 mmol; 10.00 eq.). The mixture was stirred at RT for 2 hr. After concentration, the residue was purified by prep HPLC to affold the title compound. LC-MS (M+H=379, obsd=379).

4-[1-(2-Azetidin-1-yl-ethyl)-4-(4-fluoro-3-methyl-phenyl)-1H-imidazol-2-yl]-4-(tert-butyl-dimethyl-silanyloxy)-piperidine

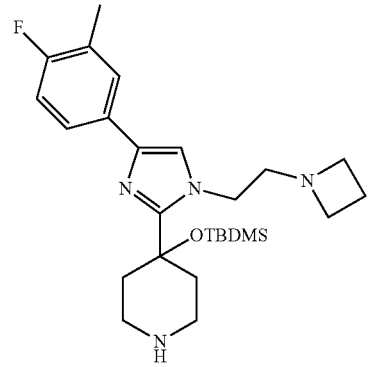 [SMILES: Cc1cc(-c2cn(CCN3CCC3)c(C3(O[Si](C)(C)C(C)(C)C)CCNCC3)n2)ccc1F]

Step 1: 4-Hydroxy-piperidine-1,4-dicarboxylic acid 1-tert-butyl ester 4-[2-(4-fluoro-3-methyl-phenyl)-2-oxo-ethyl] ester 2-Bromo-1-(4-fluoro-3-methyl-phenyl)-ethanone (2633.06 mg; 11.40 mmol; 1.00 eq.) was added to a solution of 4-hydroxy-piperidine-1,4-dicarboxylic acid 1-tert-butyl ester (2796.0 mg; 11.40 mmol; 1.00 eq.) and triethylamine (1.92 ml; 13.67 mmol; 1.20 eq.) in acetonitile (30 ml) at rt in one portion. The resulting mixture was stirred at RT for 100 min. The reaction mixture was diluted with 100 ml of ethyl acetate and washed with saturated NaHCO₃ once and brine twice. The organic layer was dried over MgSO4 and then concentrated to yield the title compound as a light brown solid, which was used directly for the next step reaction. LC-MS (M+H=396, obsd=396)

Step 2: 4-[4-(4-Fluoro-3-methyl-phenyl)-1H-imidazol-2-yl]-4-hydroxy-piperidine-1-carboxylic acid tert-butyl ester To a solution of 4-hydroxy-piperidine-1,4-dicarboxylic acid 1-tert-butyl ester 4-[2-(4-fluoro-3-methyl-phenyl)-2-oxo-ethyl] ester (4900.00 mg; 12.39 mmol; 1.00 eq.) in dioxane (30 ml), was added ammonium acetate (9551.99 mg; 123.92 mmol; 10.00 eq.). The mixture was stirred at 120° C. for 2 hr. After cooling to RT, the reaction was diluted with ethyl acetate (100 ml) and washed with brine, 5% NaHCO₃, then brine. The organic phase was dried and concentrated to give the crude product, which was treated with ether and stirred for 1 hr. The precipitate was collected to affold the title compound (4652 mg, yield 43%). LC-MS (M+H=376, obsd=376)

Step 3: 4-(tert-Butyl-dimethyl-silanyloxy)-4-[4-(4-fluoro-3-methyl-phenyl)-1H-imidazol-2-yl]-piperidine-1-carboxylic acid tert-butyl ester A mixture of 4-[4-(4-fluoro-3-methyl-phenyl)-1H-imidazol-2-yl]-4-hydroxy-piperidine-1-carboxylic acid tert-butyl ester (1600.00 mg; 4.26 mmol; 1.00 eq.), 1H-imidazole (870.37 mg; 12.79 mmol; 3.00 eq.) and tert-butyl-chloro-dimethyl-silane (1927.00 mg; 12.79 mmol; 3.00 eq.) in DMF (5 ml) was stirred at 60° C. f or 10 day and the reaction was monitored by lc-ms. The reaction mixture was poured into water and extracted with ethyl acetate. The organic phase was washed with brine, dried and concentrated to give the residue, which was treated with hexane to affold the title compound as a white solid (2087 mg, yield 91%). LC-MS (M+H=490, obsd=490)

Step 4: 4-(tert-Butyl-dimethyl-silanyloxy)-4-{4-(4-fluoro-3-methyl-phenyl)-1-[2-(tetrahydro-pyran-2-yloxy)-ethyl]-1H-imidazol-2-yl}-piperidine-1-carboxylic acid tert-butyl ester To a stirring solution of 4-(tert-butyl-dimethyl-silanyloxy)-4-[4-(4-fluoro-3-methyl-phenyl)-1H-imidazol-2-yl]-piperidine-1-carboxylic acid tert-butyl ester (1.50 g; 3.06 mmol; 1.00 eq.) in DMF (8 ml), was added NaH (0.28 g; 7.05 mmol; 2.30 eq.) by portion at 0° C. The reaction mixture was stirred at same temperature for 30 min, 2-(2-bromo-ethoxy)-tetrahydro-pyran (0.70 ml; 4.59 mmol; 1.50 eq.) was then added. The reaction mixture was stirred at RT overnight. The reaction solution was poured into water and extracted with ethyl acetate. The organic phase was washed with brine, dried and concentrated to affold the title compound (1.9 g), which was directly used for the next step reaction. LC-MS (M+H=618, obsd=618).

Step 5: 4-(tert-Butyl-dimethyl-silanyloxy)-4-[4-(4-fluoro-3-methyl-phenyl)-1-(2-hydroxy-ethyl)-1H-imidazol-2-yl]-piperidine-1-carboxylic acid tert-butyl ester To a solution of 4-(tert-butyl-dimethyl-silanyloxy)-4-{4-(4-fluoro-3-methyl-phenyl)-1-[2-(tetrahydro-pyran-2-yloxy)-ethyl]-1H-imidazol-2-yl}-piperidine-1-carboxylic acid tert-butyl ester (1.9 g, 3.06 mmol) in methanol (10 ml), was added toluene-4-sulfonic acid hydrate (0.87 g; 4.59 mmol; 1.50 eq.). The mixture was stirred at RT for 1 hr. After removal of the solvent, the residue was added ethyl acetate (100 ml), washed with 5% NaHCO$_3$, then brine, dried and concentrated. The crude was treated with ether and the precipitate was collected to yield the title compound as a light yellow solid (1.64 g). LC-MS (M+H=534, obsd=534).

Step 6: 4-[1-(2-Azetidin-1-yl-ethyl)-4-(4-fluoro-3-methyl-phenyl)-1H-imidazol-2-yl]-4-(tert-butyl-dimethyl-silanyloxy)-piperidine To a solution of 4-(tert-butyl-dimethyl-silanyloxy)-4-[4-(4-fluoro-3-methyl-phenyl)-1-(2-hydroxy-ethyl)-1H-imidazol-2-yl]-piperidine-1-carboxylic acid tert-butyl ester (1600.00 mg; 3.00 mmol; 1.00 eq.) and ethyl-diisopropyl-amine (0.81 ml; 4.50 mmol; 1.50 eq.) in THF (50 ml), was added methanesulfonyl chloride (0.31 ml; 4.05 mmol; 1.35 eq.) at 0° C. The resulting mixture was stirred at same temperature for 30 min and at RT for 2 hr. LC-MS showed the mesylation was completed. Azetidine (2.14 ml; 29.98 mmol; 10.00 eq.) was added and the reaction mixture was stirred at RT for 7 day by monitoring with LC-MS. After removal of the solvent, the residue was diluted with 50 ml of ethyl acetate and washed with brine, dried and concentrated to affold 4-[1-(2-azetidin-1-yl-ethyl)-4-(4-fluoro-3-methyl-phenyl)-1H-imidazol-2-yl]-4-(tert-butyl-dimethyl-silanyloxy)-piperidine-1-carboxylic acid tert-butyl ester (1717 mg).

To the above product dissolved in methanol (30 ml) and cooled with ice bath, was added 4.0M HCl in dioxane (5.25 ml; 20.98 mmol; 7.00 eq.) during 10 min. The resulting mixture was stirred at RT for 90 min. After removal of the solvents, the residue was neutralized with 10% Na$_2$CO$_3$ solution to pH=9, and extracted with ethyl acetate (50 ml×3). The combined organic layer was washed with brine, dried and concentrated to affold the title compound as a yellow oil (1417 mg). LC-MS (M+H=473, obsd=473).

Example 2. Compounds

4-Amino-6-{3,4-cis-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carbonitrile (racemic) ("1")

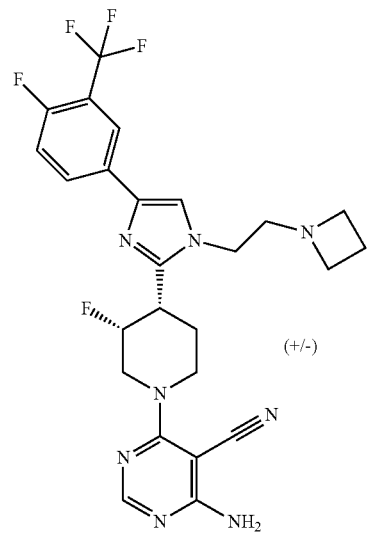 [SMILES: N#Cc1c(N)ncnc1N1CC[C@@H](c2nc(-c3ccc(F)c(C(F)(F)F)c3)cn2CCN2CCC2)[C@@H](F)C1]

To a solution of cis-4-[1-(2-azetidin-1-yl-ethyl)-4-(4-fluoro-3-trifluoromethyl-phenyl)-1H-imidazol-2-yl]-3-fluoro-piperidine (130.0 mg; 0.31 mmol; 1.0 eq.) in acetonitrile (2 ml), was added diisopropylethylamine (0.08 ml; 0.47 mmol; 1.5 eq.), followed by 4-amino-6-chloro-pyrimidine-5-carbonitrile (48.5 mg; 0.31 mmol; 1.0 eq.). The resulting mixture was stirred at rt for 3 hr as monitored by LC-MS. The precipitate was collected by filtration, washed with acetonitrile as the pure title compounds (white solid, 150 mg, 90% yield). LC-MS (M+H=533, obsd.=533). $^1$H NMR (400 MHz, DMSO-d6) δ 8.13-8.00 (m, 10H), 7.79 (s, 4H), 7.48 (dd, J=10.7, 8.8 Hz, 4H), 7.25 (s, 7H), 4.34 (dd, J=13.2, 6.3 Hz, 4H), 3.92 (tt, J=14.6, 7.3 Hz, 7H), 3.79 (dd, J=13.1, 3.4 Hz, 3H), 3.71 (d, J=9.9 Hz, 2H), 3.35 (dd, J=8.4, 4.2 Hz, 3H), 3.13 (d, J=7.0 Hz, 10H), 2.98 (d, J=6.5 Hz, 1H), 2.74-2.63 (m, 4H), 2.43 (d, J=7.1 Hz, 1H), 2.20 (s, 5H), 1.95 (d, J=7.0 Hz, 4H), 1.85 (d, J=10.0 Hz, 5H), 1.00-0.89 (m, 15H), 0.72 (d, J=6.9 Hz, 10H).

4-Amino-6-{3,4-cis-4-{1-(2-azetidin-1-yl-ethyl)-4-(4-fluoro-3-trifluoromethyl-phenyl)-1H-imidazol-2-yl}-3-fluoro-piperidin-1-yl}-pyrimidine-5-carboxamide (racemic) ("2")

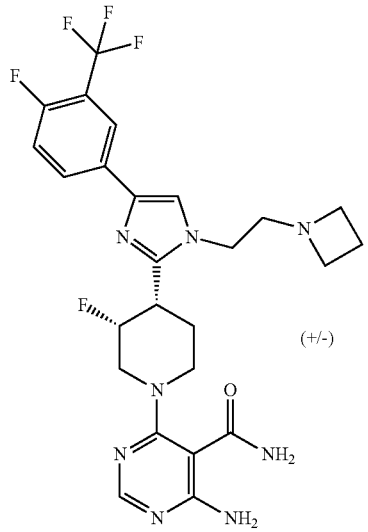 [SMILES: NC(=O)c1c(N)ncnc1N1CC[C@@H](c2nc(-c3ccc(F)c(C(F)(F)F)c3)cn2CCN2CCC2)[C@@H](F)C1]

To a solution of 4-amino-6-{3,4-cis-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carbonitrile (50.0 mg; 0.09 mmol; 1.0 eq.) in DMSO (5 ml), was added hydrogen peroxide (0.09 ml; 0.94 mmol; 10.0 eq.), followed by 2.0 M sodium hydroxide (0.47 ml; 0.94 mmol; 10.0 eq.). The reaction mixture was stirred at rt for 2 hr. The crude was purified by pre-HPLC (Waters, basic condition) yield the title compound as white solid (41 mg, 79% yield). LC-MS (M+H=551, obsd.=551). $^1$H NMR (400 MHz, DMSO-d6) δ 8.04 (d, J=1.9 Hz, 3H), 7.79 (d, J=1.7 Hz, 1H), 7.69 (s, 1H), 7.60 (s, 1H), 7.49 (t, J=9.7 Hz, 1H), 6.89 (s, 2H), 5.03-4.78 (m, 1H), 4.38-4.19 (m, 1H), 3.98 (s, 2H), 3.86-3.72 (m, 1H), 3.10 (t, J=10.8 Hz, 2H), 2.93-2.56 (m, 2H), 1.95 (dd, J=27.3, 13.6 Hz, 4H).

4-amino-6-[(3R,4S)-4-[1-[2-(azetidin-1-yl)ethyl]-4-[4-fluoro-3-(trifluoromethyl)phenyl]imidazol-2-yl]-3-fluoro-1-piperidyl]pyrimidine-5-carboxamide (chiral, absolute configuration undetermined) ("3")

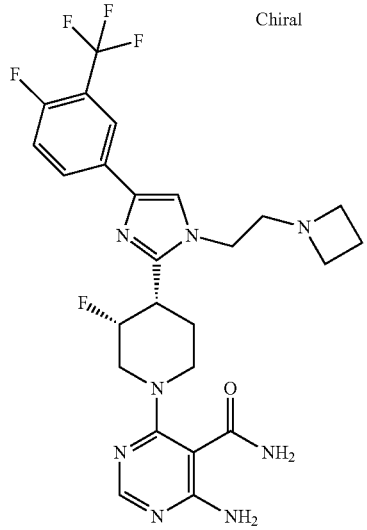 [SMILES: NC(=O)c1c(N)ncnc1N1CC[C@@H](c2nc(-c3ccc(F)c(C(F)(F)F)c3)cn2CCN2CCC2)[C@@H](F)C1]

The title compound was obtained by SFC chiral separation of racemic 4-amino-6-{3,4-cis-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carboxamide. LC-MS (M+H=551, obsd.=551).

4-amino-6-[(3S,4R)-4-[1-[2-(azetidin-1-yl)ethyl]-4-[4-fluoro-3-(trifluoromethyl)phenyl]imidazol-2-yl]-3-fluoro-1-piperidyl]pyrimidine-5-carboxamide (chiral, absolute configuration undetermined) ("4")

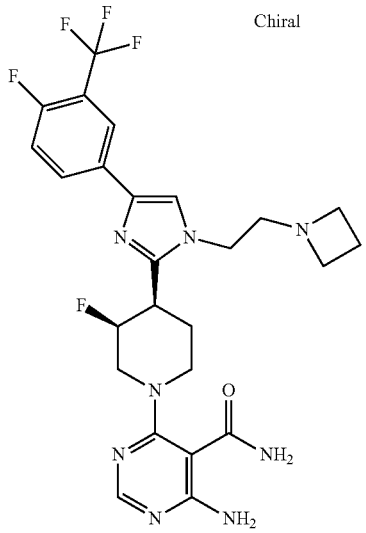 [SMILES: NC(=O)c1c(N)ncnc1N1CC[C@H](c2nc(-c3ccc(F)c(C(F)(F)F)c3)cn2CCN2CCC2)[C@H](F)C1]

The title compound was obtained by SFC chiral separation of racemic 4-amino-6-{3,4-cis-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carboxamide. LC-MS (M+H=551, obsd.=551).

4-Amino-6-{3,4-cis-4-[1-(2-azetidin-1-yl-ethyl)-4-(4-fluoro-3-trifluoromethyl-phenyl)-1H-imidazol-2-yl]-3-methyl-piperidin-1-yl}-pyrimidine-5-carbonitrile (racemic) ("5")

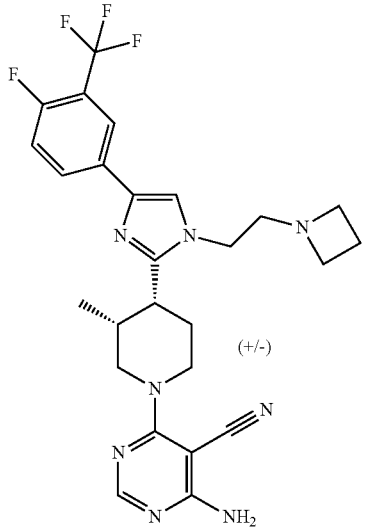 [SMILES: C[C@H]1CN(c2ncnc(N)c2C#N)CC[C@H]1c1nc(-c2ccc(F)c(C(F)(F)F)c2)cn1CCN1CCC1]

The title compound was prepared according to the procedure described for the preparation of compound "1" by using racemic cis-4-(1-(2-(azetidin-1-yl)ethyl)-4-(4-fluoro-3-(trifluoromethyl)phenyl)-1H-imidazol-2-yl)-3-methylpiperidine instead of 3,4-cis-4-[1-(2-azetidin-1-yl-ethyl)-4-(4-fluoro-3-trifluoromethyl-phenyl)-1H-imidazol-2-yl]-3-fluoro-piperidine. LC-MS (M+H=529, obsd.=529). ¹H NMR (400 MHz, DMSO-d6) δ 8.16-7.98 (m, 6H), 7.79 (s, 2H), 7.48 (dd, J=10.7, 8.8 Hz, 2H), 7.25 (s, 4H), 4.34 (dd, J=13.2, 6.3 Hz, 2H), 3.92 (dt, J=13.3, 7.1 Hz, 4H), 3.79 (dd, J=13.1, 3.4 Hz, 2H), 3.71 (d, J=9.9 Hz, 1H), 3.12 (t, J=7.0 Hz, 8H), 2.72 (dd, J=11.9, 5.9 Hz, 3H), 2.20 (s, 3H), 1.96 (p, J=6.9 Hz, 4H), 1.89-1.73 (m, 3H), 1.01-0.87 (m, 9H), 0.72 (d, J=6.9 Hz, 6H).

4-Amino-6-{3,4-cis-4-[1-(2-azetidin-1-yl-ethyl)-4-(4-fluoro-3-trifluoromethyl-phenyl)-1H-imidazol-2-yl]-3-methyl-piperidin-1-yl}-pyrimidine-5-carboxamide (racemic) ("6")

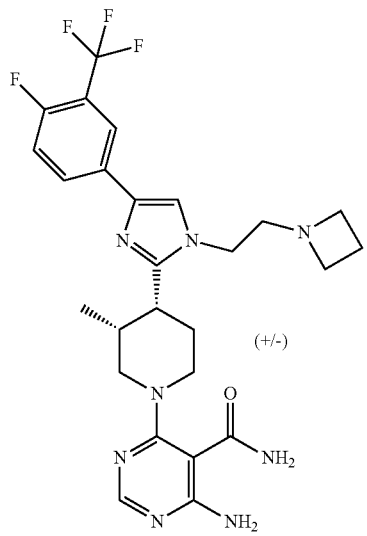 [SMILES: C[C@H]1CN(c2ncnc(N)c2C(N)=O)CC[C@H]1c1nc(-c2ccc(F)c(C(F)(F)F)c2)cn1CCN1CCC1]

The title compound was prepared according to the procedure described for the preparation of compound 2 by using 4-amino-6-{3,4-cis-4-[1-(2-azetidin-1-yl-ethyl)-4-(4-fluoro-3-trifluoromethyl-phenyl)-1H-imidazol-2-yl]-3-methyl-piperidin-1-yl}-pyrimidine-5-carbonitrile. LC-MS (M+H=547, obsd.=547). ¹H NMR (400 MHz, DMSO-d6) δ 8.12-8.01 (m, 4H), 7.98 (s, 2H), 7.77 (s, 2H), 7.48 (dd, J=10.3, 8.0 Hz, 6H), 6.73 (s, 3H), 4.02-3.76 (m, 5H), 3.44 (dd, J=12.8, 3.4 Hz, 2H), 3.26-3.19 (m, 1H), 3.11 (t, J=7.0 Hz, 6H), 2.70 (h, J=6.2 Hz, 3H), 2.24-2.02 (m, 3H), 1.95 (p, J=6.9 Hz, 3H), 1.78 (s, 2H), 0.69 (d, J=6.9 Hz, 4H).

4-amino-6-{3,4-trans-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carbonitrile (racemic) ("7")

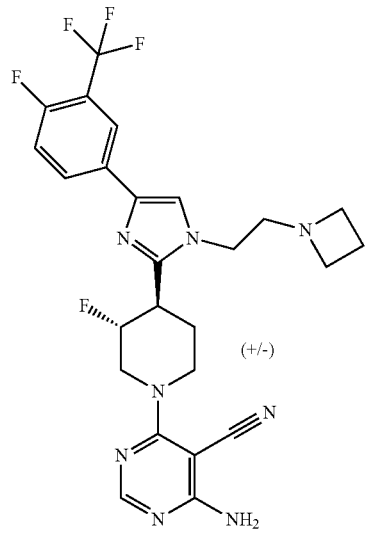 [SMILES: N#Cc1c(N)ncnc1N1CC[C@H](c2nc(-c3ccc(F)c(C(F)(F)F)c3)cn2CCN2CCC2)[C@@H](F)C1]

The title compound was prepared according to the procedure described for the preparation of compound "1" by using trans-4-[1-(2-azetidin-1-yl-ethyl)-4-(4-fluoro-3-trifluoromethyl-phenyl)-1H-imidazol-2-yl]-3-fluoro-piperidine. LC-MS (M+H=533, obsd.=533).

4-Amino-6-{3,4-trans-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carboxamide (racemic) ("8")

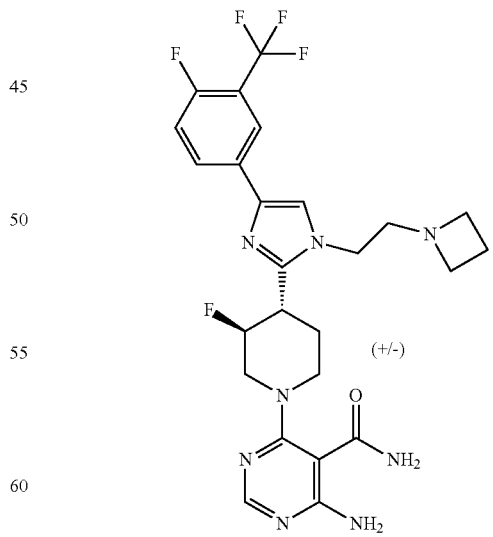

The title compound was prepared according to the procedure described for the preparation of compound "2" by using 4-amino-6-{3,4-trans-4-[1-(2-azetidin-1-yl-ethyl)-4-(4-fluoro-3-trifluoromethyl-phenyl)-1H-imidazol-2-yl]-3- fluoro-piperidin-1-yl}-pyrimidine-5-carbonitrile. LC-MS (M+H=551, obsd.=551). ¹H NMR (400 MHz, DMSO-d6) δ 8.04 (d, J=1.9 Hz, 3H), 7.79 (d, J=1.7 Hz, 1H), 7.69 (s, 1H), 7.60 (s, 1H), 7.49 (t, J=9.7 Hz, 1H), 6.89 (s, 2H), 5.06-4.94 (m, 0.5H), 4.88 (q, J=7.3, 5.0 Hz, 0.5H), 4.38-4.27 (m, 1H), 3.98 (s, 2H), 3.88-3.71 (m, 2H), 3.10 (t, J=10.8 Hz, 2H), 2.96-2.60 (m, 3H), 1.95 (dd, J=27.3, 13.6 Hz, 4H).

4-amino-6-{3,4-cis-4-[1-(2-dimethylaminoethyl)-4-(4-fluoro-3-methyl-phenyl)imidazol-2-yl]-3-fluoro-1-piperidyl]}-pyrimidine-5-carbonitrile (racemic) ("9")

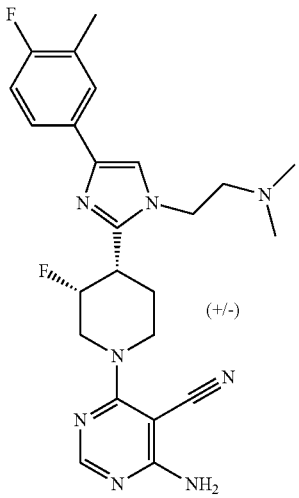 [SMILES: Cc1cc(-c2cn(CCN(C)C)c([C@@H]3CCN(c4ncnc(N)c4C#N)C[C@@H]3F)n2)ccc1F]

The title compound was prepared according to the procedure described for the preparation of compound "1" by using racemic cis-2-(4-(4-fluoro-3-methylphenyl)-2-(3-fluoropiperidin-4-yl)-1H-imidazol-1-yl)-N,N-dimethyl-ethanamine. LC-MS (M+H=467, obsd.=467).

6-{3,4-cis-4-[1-(2-Azetidin-1-yl-ethyl)-4-(4-fluoro-3-trifluoromethyl-phenyl)-1H-imidazol-2-yl]-3-fluoro-piperidin-1-yl}-5-chloro-pyrimidin-4-ylamine (racemic) ("10")

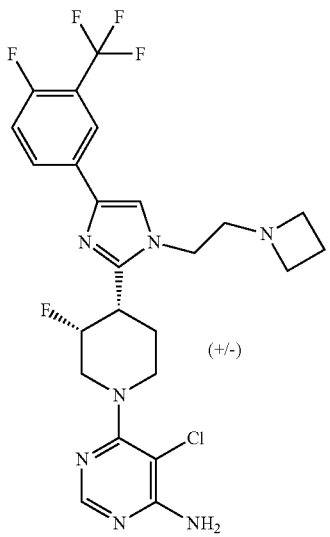

A reaction mixture of 5,6-dichloro-pyrimidin-4-ylamine (28.00 mg; 0.17 mmol; 1.00 eq.), cis-4-[1-(2-azetidin-1-yl-ethyl)-4-(4-fluoro-3-trifluoromethyl-phenyl)-1H-imidazol-2-yl]-3-fluoro-piperidine racemate (84.91 mg; 0.20 mmol; 1.20 eq.) and ethyldiisopropylamine (0.06 ml; 0.34 mmol; 2.00 eq.) in ACN (1.5 ml) was stirred at 70° C. for 2 days. The reaction mixture was concentrated and purified by HPLC to afford the title compound. LC-MS (M+H=542, obsd.=542). ¹H NMR (400 MHz, DMSO-d6) δ 8.13-7.96 (m, 3H), 7.81 (d, J=1.5 Hz, 1H), 7.48 (t, J=9.7 Hz, 1H), 6.82 (s, 2H), 5.13-4.85 (m, 1H), 4.38-4.17 (m, 2H), 3.94 (t, J=6.3 Hz, 2H), 3.53-3.47 (m, 1H), 3.43 (d, J=13.7 Hz, 1H), 3.11 (t, J=6.9 Hz, 5H), 2.74 (d, J=6.6 Hz, 2H), 2.66-2.51 (m, 1H), 1.95 (p, J=7.0 Hz, 2H), 1.80 (d, J=13.9 Hz, 1H).

6-{3,4-trans-4-[1-(2-Azetidin-1-yl-ethyl)-4-(4-fluoro-3-trifluoromethyl-phenyl)-1H-imidazol-2-yl]-3-fluoro-piperidin-1-yl}-5-chloro-pyrimidin-4-ylamine (racemic) ("11")

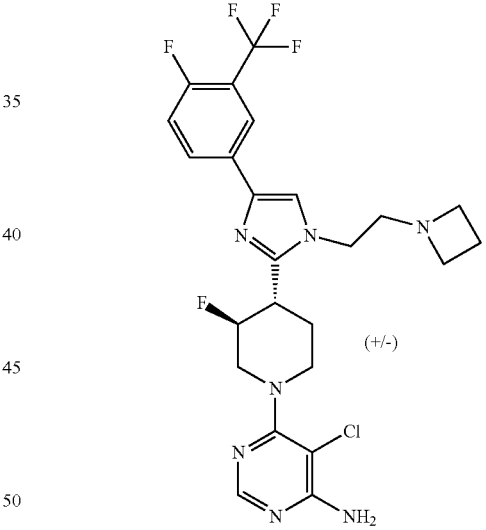

The title compound was prepared according to the procedure described for the preparation of compound "10" by using racemic trans-4-[1-(2-azetidin-1-yl-ethyl)-4-(4-fluoro-3-trifluoromethyl-phenyl)-1H-imidazol-2-yl]-3-fluoro-piperidine. LC-MS (M+H=542, obsd.=542). ¹H NMR (400 MHz, DMSO-d6) δ 8.05 (q, J=6.4 Hz, 3H), 7.78 (s, 1H), 7.48 (t, J=9.7 Hz, 1H), 6.92 (s, 2H), 4.95 (dtd, J=48.0, 9.8, 4.6 Hz, 1H), 4.33 (dt, J=11.7, 5.2 Hz, 1H), 4.04 (d, J=13.4 Hz, 1H), 3.93 (t, J=6.4 Hz, 2H), 3.21-2.96 (m, 6H), 2.70 (d, J=7.0 Hz, 2H), 2.02 (t, J=13.5 Hz, 1H), 1.99-1.78 (m, 3H).

5-chloro-6-{3,4-cis-4-[1-(2-dimethylamino-ethyl)-4-(4-fluoro-3-methyl-phenyl)-1H-imidazol-2-yl]-3-fluoro-piperidin-1-yl}-pyrimidin-4-ylamine (racemic) ("12")

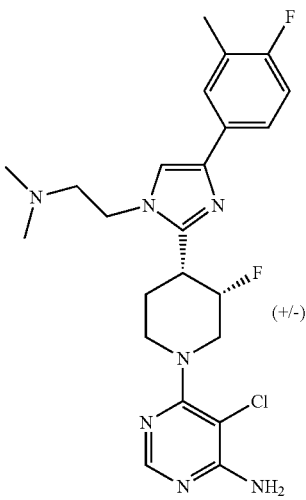 [SMILES: Cc1cc(-c2cn(CCN(C)C)c([C@H]3CCN(c4ncnc(N)c4Cl)C[C@H]3F)n2)ccc1F]

The title compound was prepared according to the procedure described for the preparation of compound "10" by using racemic cis-2-(4-(4-fluoro-3-methylphenyl)-2-(3-fluoropiperidin-4-yl)-1H-imidazol-1-yl)-N,N-dimethylethanamine. LC-MS (M+H=476, obsd.=476).

6-{3,4-cis-4-[1-(2-Azetidin-1-yl-ethyl)-4-(4-fluoro-3-trifluoromethyl-phenyl)-1H-imidazol-2-yl]-3-fluoro-piperidin-1-yl}-5-ethyl-pyrimidin-4-ylamine (racemic) ("13")

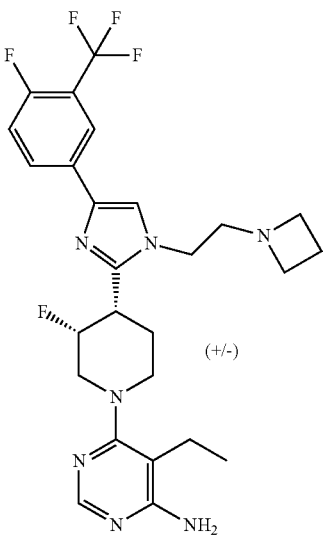 [SMILES: CCc1c(N)ncnc1N1CC[C@@H](c2nc(-c3ccc(F)c(C(F)(F)F)c3)cn2CCN2CCC2)[C@@H](F)C1]

A reaction mixture of 6-chloro-5-ethyl-pyrimidin-4-ylamine (30.00 mg; 0.19 mmol; 1.00 eq.), cis 4-[1-(2-Azetidin-1-yl-ethyl)-4-(4-fluoro-3-trifluoromethyl-phenyl)-1H-imidazol-2-yl]-3-fluoro-piperidine racemate (78.89 mg; 0.19 mmol; 1.00 eq.), 2,3,4,6,7,8,9,10-octahydro-pyrimido[1,2-a]azepine (0.05 ml; 0.38 mmol; 2.00 eq.) and NMP (0.4 ml) in 5 ml microwave tube was placed in microwave at 135° C. for 8 hr. The reaction mixture was purified by prep HPLC to affold the title compound. LC-MS (M+H=536, obsd.=536). $^1$H NMR (400 MHz, DMSO-d6) δ 8.12-7.93 (m, 3H), 7.81 (s, 1H), 7.52-7.42 (m, 1H), 6.27 (s, 2H), 5.16-4.90 (m, 1H), 4.04-3.87 (m, 5H), 3.65 (d, J=12.8 Hz, 2H), 3.09 (dt, J=16.3, 7.0 Hz, 4H), 2.80-2.57 (m, 4H), 2.01-1.88 (m, 1H), 1.82 (d, J=13.4 Hz, 1H), 1.12 (t, J=7.3 Hz, 3H).

4-Amino-6-{3,4-cis-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carbonitrile (racemic) ("14")

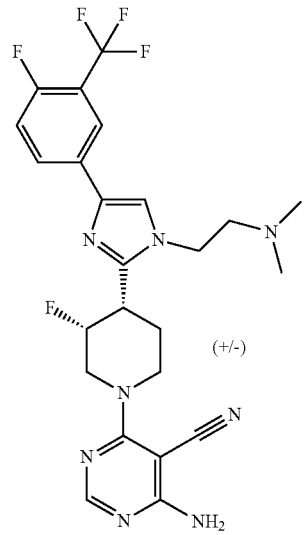 [SMILES: CN(C)CCn1cc(-c2ccc(F)c(C(F)(F)F)c2)nc1[C@@H]1CCN(c2ncnc(N)c2C#N)C[C@@H]1F]

The title compound was prepared according to the procedure described for the preparation of compound "1" by using 4-amino-6-chloro-pyrimidine-5-carbonitrile and racemic cis-2-(4-(4-fluoro-3-trifluoromethylphenyl)-2-(3-fluoropiperidin-4-yl)-1H-imidazol-1-yl)-N,N-dimethylethanamine. LC-MS (M+H=521, obsd.=521). $^1$H NMR (400 MHz, DMSO-d6) δ 8.13-7.96 (m, 5H), 7.84 (s, 1H), 7.47 (t, J=9.7 Hz, 2H), 7.33 (s, 3H), 5.12-4.92 (m, 2H), 4.87 (dd, J=14.4, 9.3 Hz, 2H), 4.71 (d, J=13.6 Hz, 2H), 4.09 (t, J=6.5 Hz, 3H), 3.68 (d, J=14.3 Hz, 1H), 3.59 (d, J=13.8 Hz, 2H), 3.51 (d, J=10.4 Hz, 1H), 3.36 (d, J=12.8 Hz, 1H), 2.63 (hept, J=5.7 Hz, 3H), 2.47-2.34 (m, 1H), 2.22 (s, 8H), 1.86 (d, J=12.4 Hz, 2H).

4-Amino-6-{3,4-cis-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carbonitrile (racemic) ("15")

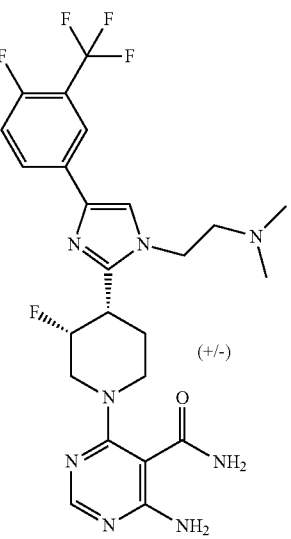

The title compound was prepared according to the procedure described for the preparation of compound "2" by using 4-amino-6-{3,4-cis-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carbonitrile. LC-MS (M+H=539, obsd.=539). ¹H NMR (400 MHz, DMSO-d6) δ 8.10-7.97 (m, 3H), 7.82 (s, 1H), 6.89 (s, 2H), 4.96 (d, J=47.6 Hz, 1H), 4.18 (d, J=13.2 Hz, 1H), 4.08 (d, J=6.5 Hz, 2H), 4.03-3.88 (m, 1H), 3.59-3.38 (m, 2H), 3.19 (t, J=11.5 Hz, 1H), 2.60 (hept, J=6.4 Hz, 2H), 2.21 (s, 6H), 1.83-1.70 (m, 1H), 6.97-6.83 (m, 2H).

6-{3,4-cis-4-[1-(2-Azetidin-1-yl-ethyl)-4-(4-fluoro-3-trifluoromethyl-phenyl)-1H-imidazol-2-yl]-3-fluoro-piperidin-1-yl}-5-ethoxy-pyrimidin-4-ylamine (racemic) ("16")

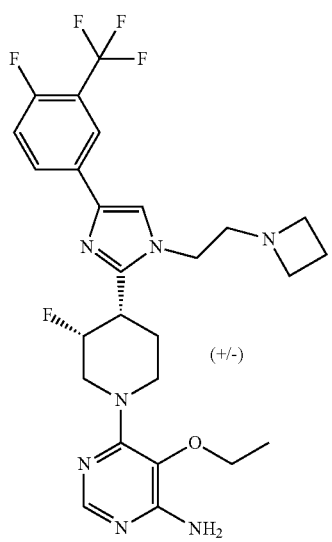 [SMILES: CCOc1c(N)ncnc1N1CC[C@@H](c2nc(-c3ccc(F)c(C(F)(F)F)c3)cn2CCN2CCC2)[C@@H](F)C1]

The title compound was prepared according to the procedure described for the preparation of compound "13" by using 6-chloro-5-ethoxypyrimidin-4-amine instead of 6-chloro-5-ethyl-pyrimidin-4-amine. LC-MS (M+H=552, obsd.=552). ¹H NMR (400 MHz, DMSO-d6) δ 8.11-7.96 (m, 2H), 7.81 (d, J=2.0 Hz, 2H), 7.48 (dd, J=10.7, 8.5 Hz, 1H), 6.19 (s, 2H), 5.01 (d, J=47.9 Hz, 1H), 4.61 (t, J=11.3 Hz, 1H), 4.46 (d, J=13.2 Hz, 1H), 3.95 (q, J=7.7, 6.4 Hz, 2H), 3.78 (q, J=7.0 Hz, 2H), 3.59-3.35 (m, 1H), 3.11 (t, J=7.0 Hz, 4H), 2.79-2.68 (m, 2H), 1.95 (p, J=6.9 Hz, 2H), 1.79 (d, J=12.9 Hz, 1H), 1.31 (t, J=7.0 Hz, 3H).

6-{cis-4-[1-(2-Dimethylamino-ethyl)-4-(4-fluoro-3-trifluoromethyl-phenyl)-1H-imidazol-2-yl]-3-fluoro-piperidin-1-yl}-5-isopropyl-pyrimidin-4-ylamine (racemic) ("17")

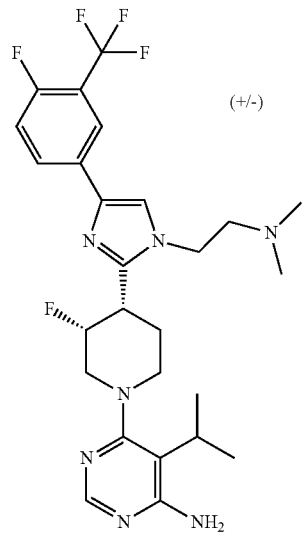 [SMILES: CC(C)c1c(N)ncnc1N1CC[C@@H](c2nc(-c3ccc(F)c(C(F)(F)F)c3)cn2CCN(C)C)[C@@H](F)C1]

To a solution of racemic cis-3-fluoro-piperidin-4-yl)-4-(4-fluoro-3-trifluoromethyl-phenyl)-imidazol-1-yl]-ethyl}-dimethyl-amine (82.06 mg; 0.20 mmol; 1.00 eq.) in NMP (0.3 ml) in a 5 ml microwave tube, were added 6-chloro-5-isopropyl-pyrimidin-4-ylamine (35.00 mg; 0.20 mmol; 1.00 eq.) and 2,3,4,6,7,8,9,10-octahydro-pyrimido[1,2-a]azepine (0.06 ml; 0.41 mmol; 2.00 eq.). The reaction mixture was placed in microwave at 130° C. for 12 h. The crude was purified by HPLC to afford the title compound. LC-MS (M+H=552, obsd.=552). ¹H NMR (400 MHz, Methanol-d4) δ 8.11-7.94 (m, 10H), 7.61 (d, J=1.1 Hz, 2H), 7.33 (q, J=9.3 Hz, 2H), 6.22 (d, J=3.1 Hz, 1H), 5.05 (s, 2H), 4.93 (s, 2H), 4.21 (q, J=7.8, 7.0 Hz, 3H), 3.94 (d, J=3.4 Hz, 1H), 3.65-3.51 (m, 3H), 3.44 (q, J=9.0, 7.3 Hz, 2H), 3.38 (d, J=6.5 Hz, 1H), 3.24 (d, J=13.6 Hz, 1H), 2.85-2.60 (m, 6H), 2.32-2.26 (m, 3H), 1.95-1.87 (m, 2H), 1.45-1.34 (m, 11H), 1.31 (s, 1H).

4-Amino-6-{cis-4-[1-(2-azetidin-1-yl-ethyl)-4-(4-fluoro-3-methyl-phenyl)-1H-imidazol-2-yl]-3-fluoro-piperidin-1-yl}-pyrimidine-5-carbonitrile (racemic) ("18")

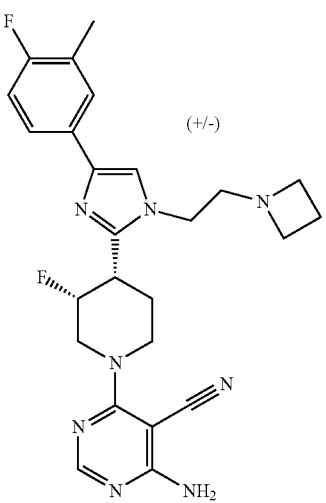 [SMILES: Cc1cc(-c2cn(CCN3CCC3)c([C@@H]3CCN(c4ncnc(N)c4C#N)C[C@@H]3F)n2)ccc1F]

To a solution of cis-4-[1-(2-azetidin-1-yl-ethyl)-4-(4-fluoro-3-methyl-phenyl)-1H-imidazol-2-yl]-3-fluoro-piperidine (80.00 mg; 0.22 mmol; 1.00 eq.) in acetonitrile, were added ethyldiisopropylamine (0.06 ml; 0.33 mmol; 1.50 eq.) and 4-amino-6-chloro-pyrimidine-5-carbonitrile (34.30 mg; 0.22 mmol; 1.00 eq.). The mixture was stirred at RT for 1 h. The crude was purified by prep HPLC to affod the title compound. LC-MS (M+H=477, obsd.=477). $^1$H NMR (400 MHz, DMSO-d6) δ 8.09 (s, 2H), 7.63 (d, J=7.5 Hz, 2H), 7.55 (d, J=11.4 Hz, 4H), 7.33 (s, 3H), 7.07 (t, J=9.2 Hz, 2H), 5.05 (d, J=47.4 Hz, 2H), 4.86 (dd, J=14.3, 9.5 Hz, 2H), 4.71 (d, J=13.7 Hz, 2H), 4.11-3.99 (m, 2H), 3.99-3.85 (m, 3H), 3.71-3.40 (m, 4H), 3.36 (s, 1H), 3.29 (s, 2H), 3.18 (d, J=5.5 Hz, 2H), 3.10 (t, J=7.0 Hz, 7H), 2.71 (q, J=7.9, 7.1 Hz, 4H), 2.44 (d, J=13.1 Hz, 1H), 2.25 (s, 5H), 1.95 (p, J=7.0 Hz, 4H), 1.90-1.78 (m, 2H), 1.19 (t, J=7.2 Hz, 2H).

4-Amino-6-{cis-4-[1-(2-azetidin-1-yl-ethyl)-4-(4-fluoro-3-methyl-phenyl)-1H-imidazol-2-yl]-3-fluoro-piperidin-1-yl}-pyrimidine-5-carboxylic acid amide (racamic) ("19")

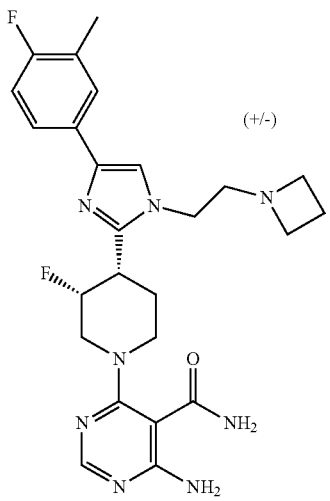 [SMILES: Cc1cc(-c2cn(CCN3CCC3)c([C@@H]3CCN(c4ncnc(N)c4C(N)=O)C[C@@H]3F)n2)ccc1F]

To a solution of 4-amino-6-{cis-4-[1-(2-azetidin-1-yl-ethyl)-4-(4-fluoro-3-methyl-phenyl)-1H-imidazol-2-yl]-3-fluoro-piperidin-1-yl}-pyrimidine-5-carbonitrile (70.00 mg; 0.15 mmol; 1.00 eq.) in DMSO (8 ml) were added H$_2$O$_2$ (0.14 ml; 1.46 mmol; 10.00 eq.) and 2.0M NaOH aq (0.73 ml; 1.46 mmol; 10.00 eq.) at rt. The resulting mixture was stirred at rt for 2 h. Purification of the crude by HPLC (basic) afforded the title compound. LC-MS (M+H=497, obsd.=497). $^1$H NMR (400 MHz, Methanol-d4) δ 8.06 (d, J=1.2 Hz, 2H), 7.61 (d, J=7.5 Hz, 2H), 7.54 (q, J=8.1, 6.6 Hz, 1H), 7.40 (s, 1H), 7.00 (t, J=9.0 Hz, 2H), 5.06 (s, 1H), 4.94 (s, 1H), 4.29-4.13 (m, 3H), 4.03 (t, J=6.6 Hz, 3H), 3.59-3.37 (m, 4H), 3.26 (t, J=7.2 Hz, 8H), 2.91-2.79 (m, 3H), 2.77-2.59 (m, 2H), 2.30 (s, 4H), 2.12 (p, J=7.3 Hz, 3H), 1.93-1.84 (m, 2H).

4-Amino-6-{(3S,4R)-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carboxylic acid amide (chiral, absolute configuration undetermined) ("20")

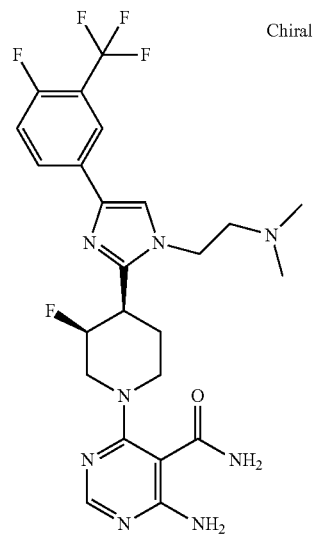 [SMILES: CN(C)CCn1cc(-c2ccc(F)c(C(F)(F)F)c2)nc1[C@H]1CCN(c2ncnc(N)c2C(N)=O)C[C@H]1F]

The title compound was obtained by SFC chiral separation of racemic 4-amino-6-{cis-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carboxylic acid amide. LC-MS (M+H=539, obsd.=539).

4-Amino-6-{(3R,4S)-4-[1-(2-dimethylamino-ethyl)-4-(4-fluoro-3-trifluoromethyl-phenyl)-1H-imidazol-2-yl]-3-fluoro-piperidin-1-yl}-pyrimidine-5-carboxylic acid amide (chiral, absolute configuration undetermined) ("21")

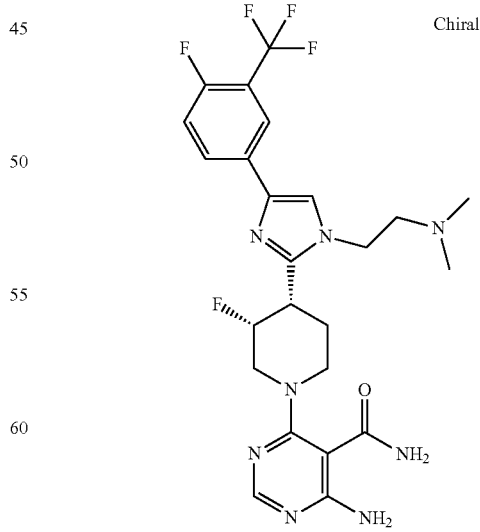

The title compound was obtained by SFC chiral separation of racemic 4-amino-6-{cis-4-[1-(2-dimethylaminoethyl)-4-(4-fluoro-3-trifluoromethyl-phenyl)-1H-imidazol-2-yl]-3-fluoro-piperidin-1-yl}-pyrimidine-5-carboxylic acid amide. LC-MS (M+H=539, obsd.=539).

6-{(3R,4S)-4-[1-(2-Azetidin-1-yl-ethyl)-4-(4-fluoro-3-trifluoromethyl-phenyl)-1H-imidazol-2-yl]-3-fluoro-piperidin-1-yl}-5-ethoxy-pyrimidin-4-ylamine (chiral, absolute configuration undetermined) ("22")

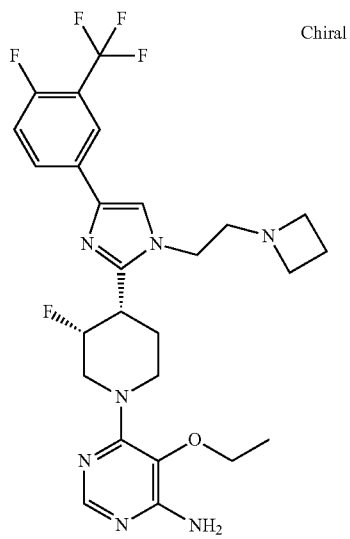 [SMILES: CCOc1c(N)ncnc1N1CC[C@@H](c2nc(-c3ccc(F)c(C(F)(F)F)c3)cn2CCN2CCC2)[C@@H](F)C1]

The title compound was obtained by SFC chiral separation of racemic 6-{cis-4-[1-(2-azetidin-1-yl-ethyl)-4-(4-fluoro-3-trifluoromethyl-phenyl)-1H-imidazol-2-yl]-3-fluoro-piperidin-1-yl}-5-ethoxy-pyrimidin-4-ylamine. LC-MS (M+H=552, obsd.=552).

6-{(3S,4R)-4-[1-(2-Azetidin-1-yl-ethyl)-4-(4-fluoro-3-trifluoromethyl-phenyl)-1H-imidazol-2-yl]-3-fluoro-piperidin-1-yl}-5-ethoxy-pyrimidin-4-ylamine (chiral, absolute configuration undetermined) ("23")

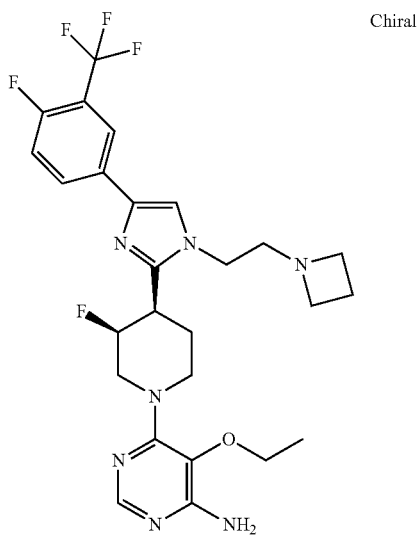 [SMILES: CCOc1c(N)ncnc1N1CC[C@H](c2nc(-c3ccc(F)c(C(F)(F)F)c3)cn2CCN2CCC2)[C@H](F)C1]

The title compound was obtained by SFC chiral separation of racemic 6-{cis-4-[1-(2-azetidin-1-yl-ethyl)-4-(4-fluoro-3-trifluoromethyl-phenyl)-1H-imidazol-2-yl]-3-fluoro-piperidin-1-yl}-5-ethoxy-pyrimidin-4-ylamine. LC-MS (M+H=552, obsd.=552).

6-{cis-4-[1-(2-Azetidin-1-yl-ethyl)-4-(4-fluoro-3-methyl-phenyl)-1H-imidazol-2-yl]-3-fluoro-piperidin-1-yl}-5-isopropyl-pyrimidin-4-ylamine (racemic) ("24")

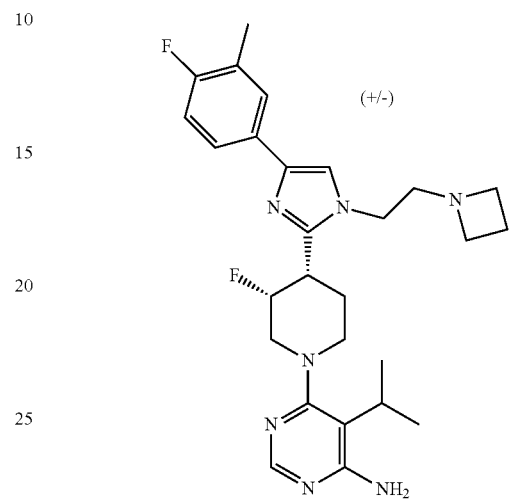

To a solution of cis-4-[1-(2-azetidin-1-yl-ethyl)-4-(4-fluoro-3-methyl-phenyl)-1H-imidazol-2-yl]-3-fluoro-piperidine (100.81 mg; 0.28 mmol; 1.00 eq.) in NMP (0.3 ml), were added 2,3,4,6,7,8,9,10-octahydro-pyrimido[1,2-a]azepine (0.08 ml; 0.56 mmol; 2.00 eq.) and 6-chloro-5-isopropyl-pyrimidin-4-ylamine (48.00 mg; 0.28 mmol; 1.00 eq.). The reaction mixture was placed in microwave at 130° C. for 7 h. The crude was purified by prep HPLC to afford the title compound. LC-MS (M+H=496, obsd.=496).

5-Chloro-6-cis-4-[1-(2-dimethylamino-ethyl)-4-(4-fluoro-3-trifluoromethyl-phenyl)-1H-imidazol-2-yl]-3-fluoro-piperidin-1-yl}-pyrimidin-4-ylamine (racemic) ("25")

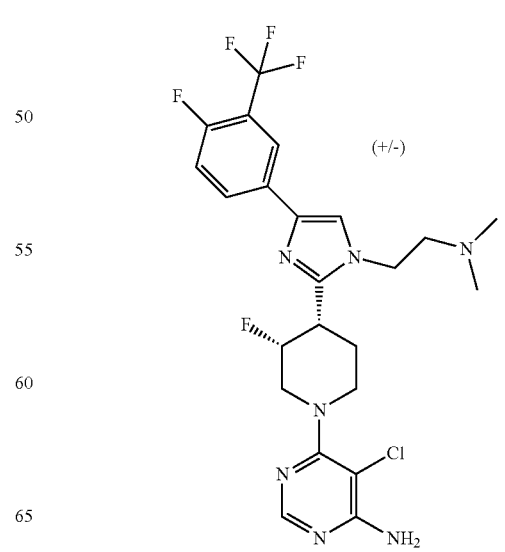

To a solution of {2-[2-((cis-3-fluoro-piperidin-4-yl)-4-(4-fluoro-3-trifluoromethyl-phenyl)-imidazol-1-yl]-ethyl}-dimethyl-amine (racemic) (82.00 mg; 0.20 mmol; 1.00 eq.) in acetonitrile (1 ml), were added ethyldiisopropylamine (0.05 ml; 0.30 mmol; 1.50 eq.) and 5,6-dichloro-pyrimidin-4-ylamine (32.60 mg; 0.20 mmol; 1.00 eq.). The mixture was stirred at 100° C. overnight. The crude was purified by prep HPLC to affold the title compound. LC-MS (M+H=530, obsd.=530). $^1$H NMR (400 MHz, DMSO-d6) δ 8.11-7.97 (m, 3H), 7.85-7.78 (m, 1H), 7.48 (t, J=9.6 Hz, 1H), 6.83 (s, 2H), 5.07-4.84 (m, 1H), 4.37-4.19 (m, 2H), 4.10 (q, J=7.7, 6.5 Hz, 2H), 3.51 (d, J=14.0 Hz, 1H), 3.43 (t, J=10.4 Hz, 1H), 3.12 (t, J=12.0 Hz, 1H), 2.62 (td, J=13.5, 7.0 Hz, 3H), 2.31-2.17 (m, 5H), 2.19-2.11 (m, 1H), 1.80 (d, J=13.1 Hz, 1H).

6-{cis-3-Fluoro-4-[4-(4-fluoro-3-trifluoromethyl-phenyl)-1H-imidazol-2-yl]-piperidin-1-yl}-5-isopropyl-pyrimidin-4-ylamine (racemic) ("26")

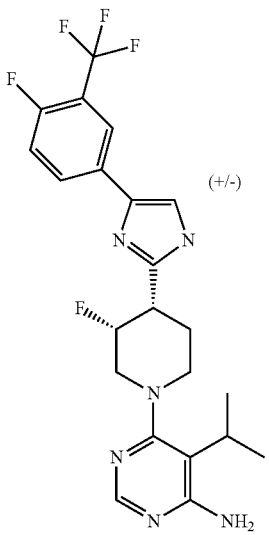 [SMILES: CC(C)c1c(N)ncnc1N1CC[C@@H](c2nc(-c3ccc(F)c(C(F)(F)F)c3)c[nH]2)[C@@H](F)C1]

A reaction mixture of 6-chloro-5-isopropyl-pyrimidin-4-ylamine (110.00 mg; 0.64 mmol; 1.00 eq.), cis-3-fluoro-4-[4-(4-fluoro-3-trifluoromethyl-phenyl)-1H-imidazol-2-yl]-piperidine (racemic) (212.33 mg; 0.64 mmol; 1.00 eq.) and 2,3,4,6,7,8,9,10-octahydro-pyrimido[1,2-a]azepine (0.18 ml; 1.28 mmol; 2.00 eq.) in NMP (0.4 ml) was placed in microwave at 135° C. for 10 h. The crude was purified by prep HPLC to yield the title compound. LC-MS (M+H=467, obsd.=467). $^1$H NMR (400 MHz, DMSO-d6) δ 8.09 (dd, J=7.4, 5.1 Hz, 2H), 8.03 (s, 1H), 7.74 (s, 1H), 7.49 (t, J=10.0 Hz, 1H), 6.19 (s, 2H), 5.09 (d, J=48.0 Hz, 1H), 3.53 (dd, J=14.4, 9.4 Hz, 1H), 3.39 (dd, J=20.8, 10.3 Hz, 2H), 3.24-3.02 (m, 1H), 2.91 (t, J=11.8 Hz, 1H), 2.41-2.28 (m, 1H), 2.00-1.90 (m, 1H), 1.36-1.20 (m, 6H).

4-Amino-6-{(3R,4S)-4-[1-(2-azetidin-1-yl-ethyl)-4-(4-fluoro-3-methyl-phenyl)-1H-imidazol-2-yl]-3-fluoro-piperidin-1-yl}-pyrimidine-5-carboxylic acid amide (chiral, absolute configuration undetermined) ("27")

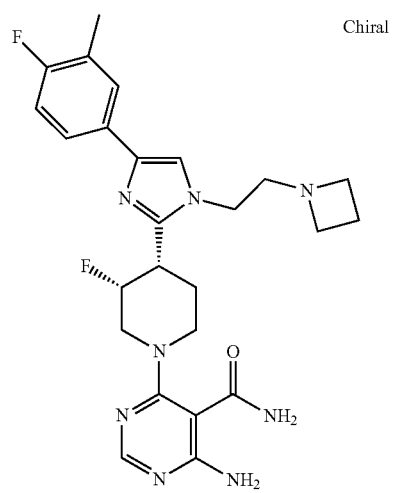 [SMILES: Cc1cc(-c2cn(CCN3CCC3)c([C@@H]3CCN(c4ncnc(N)c4C(N)=O)C[C@@H]3F)n2)ccc1F]

The title compound was obtained by SFC chiral separation of racemic 4-amino-6-{cis-4-[1-(2-azetidin-1-yl-ethyl)-4-(4-fluoro-3-methyl-phenyl)-1H-imidazol-2-yl]-3-fluoro-piperidin-1-yl}-pyrimidine-5-carboxylic acid amide. LC-MS (M+H=497, obsd.=497).

4-Amino-6-{(3S,4R)-4-[1-(2-azetidin-1-yl-ethyl)-4-(4-fluoro-3-methyl-phenyl)-1H-imidazol-2-yl]-3-fluoro-piperidin-1-yl}-pyrimidine-5-carboxylic acid amide (chiral, absolute configuration undetermined) ("28").

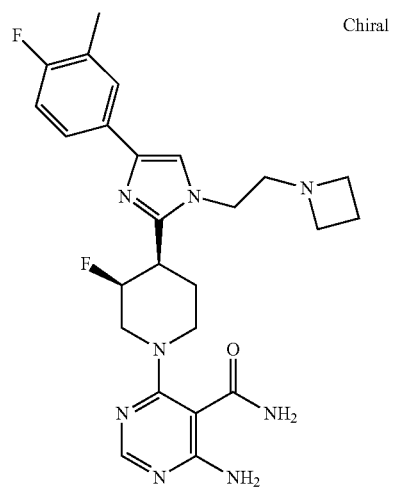 [SMILES: Cc1cc(-c2cn(CCN3CCC3)c([C@H]3CCN(c4ncnc(N)c4C(N)=O)C[C@H]3F)n2)ccc1F]

The title compound was obtained by SFC chiral separation of racemic 4-amino-6-{cis-4-[1-(2-azetidin-1-yl-ethyl)-4-(4-fluoro-3-methyl-phenyl)-1H-imidazol-2-yl]-3-fluoro-piperidin-1-yl}-pyrimidine-5-carboxylic acid amide. LC-MS (M+H=497, obsd.=497).

5-Chloro-6-{(3R,4S)-4-[1-(2-dimethylamino-ethyl)-4-(4-fluoro-3-trifluoromethyl-phenyl)-1H-imidazol-2-yl]-3-fluoro-piperidin-1-yl}-pyrimidin-4-ylamine (chiral, absolute configuration undetermined) ("29")

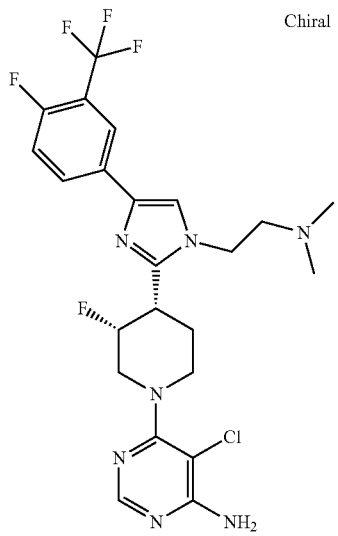 [SMILES: CN(C)CCn1cc(-c2ccc(F)c(C(F)(F)F)c2)nc1[C@@H]1CCN(c2ncnc(N)c2Cl)C[C@@H]1F]

The title compound was obtained by SFC chiral separation of racemic 5-chloro-6-{cis-4-[1-(2-dimethylamino-ethyl)-4-(4-fluoro-3-trifluoromethyl-phenyl)-1H-imidazol-2-yl]-3-fluoro-piperidin-1-yl}-pyrimidin-4-ylamine. LC-MS (M+H=530, obsd.=530).

5-Chloro-6-{(3S,4R)-4-[1-(2-dimethylamino-ethyl)-4-(4-fluoro-3-trifluoromethyl-phenyl)-1H-imidazol-2-yl]-3-fluoro-piperidin-1-yl}-pyrimidin-4-ylamine (chiral, absolute configuration undetermined) ("30")

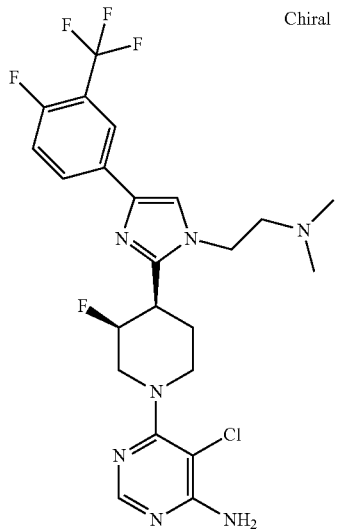 [SMILES: CN(C)CCn1cc(-c2ccc(F)c(C(F)(F)F)c2)nc1[C@H]1CCN(c2ncnc(N)c2Cl)C[C@H]1F]

The title compound was obtained by SFC chiral separation of racemic 5-chloro-6-{cis-4-[1-(2-dimethylamino-ethyl)-4-(4-fluoro-3-trifluoromethyl-phenyl)-1H-imidazol-2-yl]-3-fluoro-piperidin-1-yl}-pyrimidin-4-ylamine. LC-MS (M+H=530, obsd.=530).

6-{(3S,4R)-4-[1-(2-Dimethylamino-ethyl)-4-(4-fluoro-3-trifluoromethyl-phenyl)-1H-imidazol-2-yl]-3-fluoro-piperidin-1-yl}-5-isopropyl-pyrimidin-4-ylamine (chiral, absolute configuration undetermined) ("31")

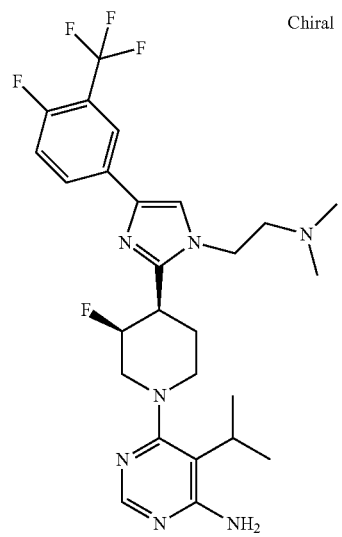 [SMILES: CC(C)c1c(N)ncnc1N1CC[C@H](c2nc(-c3ccc(F)c(C(F)(F)F)c3)cn2CCN(C)C)[C@H](F)C1]

The title compound was obtained by SFC chiral separation of racemic 6-{3,4-cis-4-[1-(2-dimethylamino-ethyl)-4-(4-fluoro-3-trifluoromethyl-phenyl)-1H-imidazol-2-yl]-3-fluoro-piperidin-1-yl}-5-isopropyl-pyrimidin-4-ylamine. LC-MS (M+H=538, obsd.=538).

6-{(3R,4S)-4-[1-(2-Dimethylamino-ethyl)-4-(4-fluoro-3-trifluoromethyl-phenyl)-1H-imidazol-2-yl]-3-fluoro-piperidin-1-yl}-5-isopropyl-pyrimidin-4-ylamine (chiral, absolute configuration undetermined) ("32")

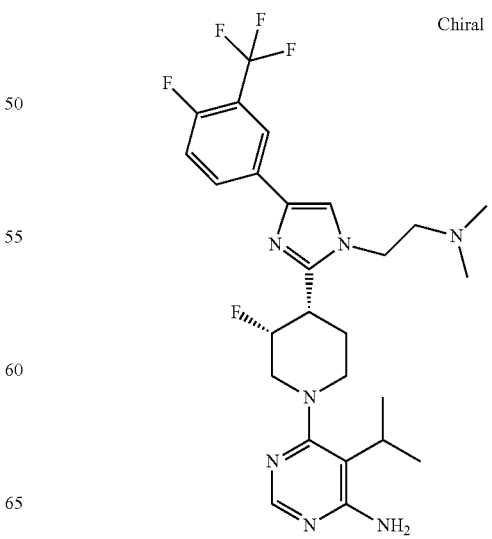

The title compound was obtained by SFC chiral separation of racemic 6-{3,4-cis-4-[1-(2-dimethylamino-ethyl)-4-(4-fluoro-3-trifluoromethyl-phenyl)-1H-imidazol-2-yl]-3-fluoro-piperidin-1-yl}-5-isopropyl-pyrimidin-4-ylamine. LC-MS (M+H=538, obsd.=538).

6-{cis-4-[1-(2-Amino-ethyl)-4-(4-fluoro-3-trifluoromethyl-phenyl)-1H-imidazol-2-yl]-3-fluoro-piperidin-1-yl}-5-isopropyl-pyrimidin-4-ylamine (racemic) ("33")

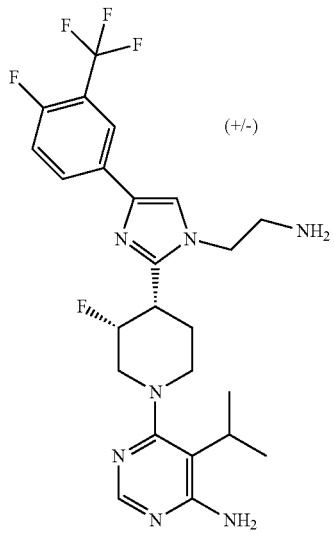 [SMILES: CC(C)c1c(N)ncnc1N1CC[C@@H](c2nc(-c3ccc(F)c(C(F)(F)F)c3)cn2CCN)[C@@H](F)C1]

Step 1: 2-[cis-3-Fluoro-piperidin-4-yl)-4-(4-fluoro-3-trifluoromethyl-phenyl)-imidazol-1-yl]-ethylamine To a solution of 3-fluoro-4-[4-(4-fluoro-3-trifluoromethyl-phenyl)-1H-imidazol-2-yl]-piperidine-1-carboxylic acid tert-butyl ester (3000.00 mg; 6.95 mmol; 1.00 eq.) in DMF (10.00 ml; 129.70 mmol; 18.65 eq.), was added NaH (639.72 mg; 15.99 mmol; 2.30 eq.). After stirring at RT for 30 min, (2-bromoethyl)-carbamic acid tert-butyl ester was added (2805.09 mg; 12.52 mmol; 1.80 eq.) and stirred at RT for 10 days. The reaction mixture was diluted with ethyl acetate (100 ml) and washed with brine. The organic phase was dried and concentrated to yield (4-[1-(2-tert-Butoxycarbonylamino-ethyl)-4-(4-fluoro-3-trifluoromethyl-phenyl)-1H-imidazol-2-yl]-3-fluoro-piperidine-1-carboxylic acid tert-butyl ester.

To the above product in DCM (10 ml), was added trifluoroacetic acid (1189.40 mg; 10.43 mmol; 1.50 eq.). The reaction mixture was stirred at RT for 1 h. After removal of the solvent, the residue was purified by prep HPLC (basic) to yield the title compound. LC-MS (M+H=375, obsd.=375).

Step 2: 6-{cis-4-[1-(2-Amino-ethyl)-4-(4-fluoro-3-trifluoromethyl-phenyl)-1H-imidazol-2-yl]-3-fluoro-piperidin-1-yl}-5-isopropyl-pyrimidin-4-ylamine (racemic)

A mixture of 2-[2-cis-3-fluoro-piperidin-4-yl)-4-(4-fluoro-3-trifluoromethyl-phenyl)-imidazol-1-yl]-ethylamine (80.00 mg; 0.21 mmol; 1.00 eq.), 6-chloro-5-isopropyl-pyrimidin-4-ylamine (34.84 mg; 0.20 mmol; 0.95 eq.) and 2,3,4,6,7,8,9,10-octahydro-pyrimido[1,2-a]azepine (0.06 ml; 0.43 mmol; 2.00 eq.) in NMP (0.2 ml) was placed in microwave at 130° C. for 11 h. The crude was purified by HPLC to yield the title compound. LC-MS (M+H=510, obsd.=510).

6-{(3S,4R)-4-[1-(2-Azetidin-1-yl-ethyl)-4-(4-fluoro-3-methyl-phenyl)-1H-imidazol-2-yl]-3-fluoro-piperidin-1-yl}-5-isopropyl-pyrimidin-4-ylamine (chiral, absolute configuration undetermined) ("34")

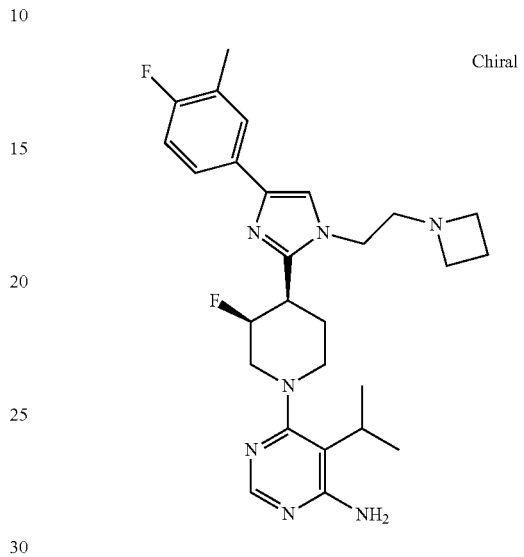

The title compound was obtained by SFC chiral separation of racemic 6-{cis-4-[1-(2-azetidin-1-yl-ethyl)-4-(4-fluoro-3-methyl-phenyl)-1H-imidazol-2-yl]-3-fluoro-piperidin-1-yl}-5-isopropyl-pyrimidin-4-ylamine. LC-MS (M+H=496, obsd.=496).

6-{(3R,4S)-4-[1-(2-Azetidin-1-yl-ethyl)-4-(4-fluoro-3-methyl-phenyl)-1H-imidazol-2-yl]-3-fluoro-piperidin-1-yl}-5-isopropyl-pyrimidin-4-ylamine (chiral, absolute configuration undetermined) ("35")

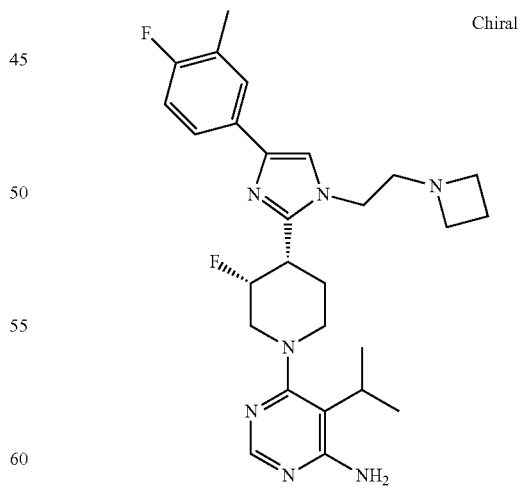

The title compound was obtained by SFC chiral separation of racemic 6-{cis-4-[1-(2-azetidin-1-yl-ethyl)-4-(4-fluoro-3-methyl-phenyl)-1H-imidazol-2-yl]-3-fluoro-piperidin-1-yl}-5-isopropyl-pyrimidin-4-ylamine. LC-MS (M+H=496, obsd.=496).

6-{(cis-4-[1-(2-Amino-ethyl)-4-(4-fluoro-3-trifluoromethyl-phenyl)-1H-imidazol-2-yl]-3-fluoro-piperidin-1-yl}-5-chloro-pyrimidin-4-ylamine (racemic) ("36")

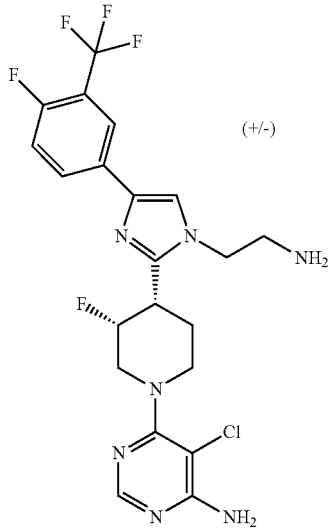 [SMILES: NCCn1cc(-c2ccc(F)c(C(F)(F)F)c2)nc1[C@@H]1CCN(c2ncnc(N)c2Cl)C[C@@H]1F]

A reaction mixture of 5,6-dichloro-pyrimidin-4-ylamine (35.00 mg; 0.21 mmol; 1.00 eq.), racemic 2-[2-(cis-3-fluoro-piperidin-4-yl)-4-(4-fluoro-3-trifluoromethyl-phenyl)-imidazol-1-yl]-ethylamine (87.89 mg; 0.23 mmol; 1.10 eq.), and ethyldiisopropylamine (0.08 ml; 0.43 mmol; 2.00 eq.) in ACN (1.5 ml) was stirred at 70° C. for 48 h. After removal of the solvent, the crude was purified by HPLC to yield the title compound. LC-MS (M+H=502, obsd.=502).

6-{cis-3-Fluoro-4-[4-(4-fluoro-3-methyl-phenyl)-1-(2-isopropylamino-ethyl)-1H-imidazol-2-yl]-piperidin-1-yl}-5-isopropyl-pyrimidin-4-ylamine (racemic) ("37")

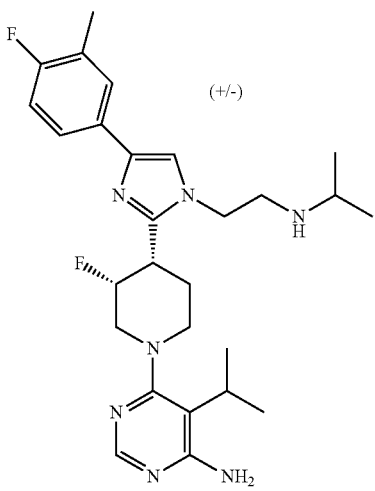 [SMILES: Cc1cc(-c2cn(CCNC(C)C)c([C@@H]3CCN(c4ncnc(N)c4C(C)C)C[C@@H]3F)n2)ccc1F]

Step 1: 2-[4-(4-Fluoro-3-methyl-phenyl)-2-(cis-3-fluoro-piperidin-4-yl)-imidazol-1-yl]-ethanol To a solution of racemic cis-3-fluoro-4-{4-(4-fluoro-3-methyl-phenyl)-1-[2-(tetrahydro-pyran-2-yloxy)-ethyl]-1H-imidazol-2-yl}-piperidine-1-carboxylic acid tert-butyl ester (4226.79 mg; 8.36 mmol; 1.00 eq.) in DCM (15 ml), was added trifluoroacetic acid (11438.82 mg; 100.32 mmol; 12.00 eq.). The reaction mixture was stirred at RT for 1 hr. After removal of the solvent, the residue was purified by pre-HPLC to afford the title compound (1100 mg, yield 40.9%). LC-MS (M+H=322, obsd.=322).

Step 2: 2-[2-[(cis-1-(6-Amino-5-isopropyl-pyrimidin-4-yl)-3-fluoro-piperidin-4-yl]-4-(4-fluoro-3-methyl-phenyl)-imidazol-1-yl]-ethanol The mixture of 2-[4-(4-fluoro-3-methyl-phenyl)-2-(cis-3-fluoro-piperidin-4-yl)-imidazol-1-yl]-ethanol (337.04 mg; 1.05 mmol; 1.00 eq.) and 6-chloro-5-isopropyl-pyrimidin-4-ylamine (180.00 mg; 1.05 mmol; 1.00 eq) in NMP (0.5 ml) was placed in microwave at 140° C. for 10 hr. The residue was purified by prep H PLC to yield the title compound. LC-MS (M+H=457, obsd.=457).

Step 3: 6-{cis-3-Fluoro-4-[4-(4-fluoro-3-methyl-phenyl)-1-(2-isopropylamino-ethyl)-1H-imidazol-2-yl]-piperidin-1-yl}-5-isopropyl-pyrimidin-4-ylamine (racemic)

To a solution of 2-[2-[cis-1-(6-amino-5-isopropyl-pyrimidin-4-yl)-3-fluoro-piperidin-4-yl]-4-(4-fluoro-3-methyl-phenyl)-imidazol-1-yl]-ethanol (210.00 mg; 0.46 mmol; 1.00 eq.) and ethyldiisopropylamine (0.17 ml; 0.92 mmol; 2.00 eq.) in THF (1 ml), was added methanesulfonyl chloride (0.05 ml; 0.69 mmol; 1.50 eq.). The reaction mixture was stirred at RT for 3 hr. LC-MS showed the mesylation was completed. Isopropylamine (0.34 ml; 4.60 mmol; 10.00 eq.) was added to the reaction mixture and then stirred at RT overnight and at 40° C. for another 24 hr. The crude was purified by prep HPLC to affold the title compound. LC-MS (M+H=478, obsd.=478). $^1$H NMR (400 MHz, DMSO-d6) δ 8.03 (s, 1H), 7.71-7.61 (m, 1H), 7.57 (d, J=14.3 Hz, 2H), 7.08 (t, J=9.2 Hz, 1H), 6.16 (s, 2H), 5.01 (d, J=47.8 Hz, 1H), 4.00 (t, J=6.6 Hz, 2H), 3.56-3.40 (m, 2H), 3.25-3.08 (m, 1H), 2.93-2.81 (m, 3H), 2.72 (q, J=6.2 Hz, 1H), 1.90-1.64 (m, 3H), 1.29 (dd, J=19.8, 7.2 Hz, 6H), 0.97 (dd, J=6.3, 2.5 Hz, 6H).

6-{cis-3-Fluoro-4-[4-(4-fluoro-3-methyl-phenyl)-1-(2-methylamino-ethyl)-1H-imidazol-2-yl]-piperidin-1-yl}-5-isopropyl-pyrimidin-4-ylamine (racemic) ("38")

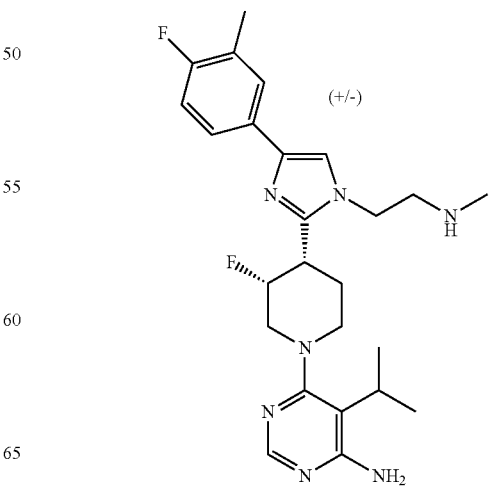

To a solution of 2-[2-[cis-1-(6-amino-5-isopropyl-pyrimidin-4-yl)-3-fluoro-piperidin-4-yl]-4-(4-fluoro-3-methyl-phenyl)-imidazol-1-yl]-ethanol (102.00 mg; 0.22 mmol; 1.00 eq.) and ethyldiisopropylamine (0.08 ml; 0.45 mmol; 2.00 eq.) in THF (1 ml), was added methanesulfonyl chloride (0.025 ml; 0.336 mmol; 1.50 eq.). The reaction mixture was stirred at RT for 3 hr. LC-MS showed the mesylation was completed. Methylamine (2.0M in THF, 1.12 ml; 2.24 mmol; 10.00 eq.) was added. The reaction mixture was stirred at RT for 24 hr and then 40° C. for another 24 hr. After removal of the solvent, the crude was purified by prep HPLC to affold the title compound. LC-MS (M+H=470, obsd.=470).

6-{cis-4-[1-(2-Azetidin-1-yl-ethyl)-4-(4-fluoro-3-methyl-phenyl)-1H-imidazol-2-yl]-3-fluoro-piperidin-1-yl}-5-isopropoxy-pyrimidin-4-ylamine (racemic) ("39")

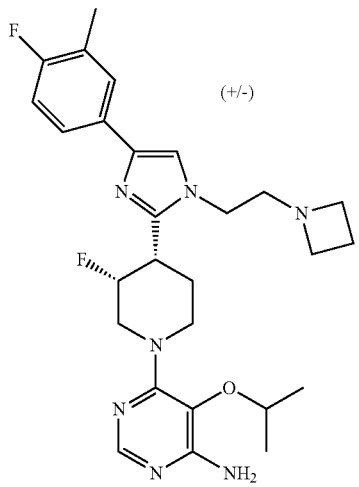 [SMILES: Cc1cc(-c2cn(CCN3CCC3)c([C@@H]3CCN(c4ncnc(N)c4OC(C)C)C[C@@H]3F)n2)ccc1F]

The solution of cis-4-[1-(2-azetidin-1-yl-ethyl)-4-(4-fluoro-3-methyl-phenyl)-1H-imidazol-2-yl]-3-fluoro-piperidine (86.45 mg; 0.24 mmol; 1.00 eq.), 6-chloro-5-isopropoxy-pyrimidin-4-ylamine (45.00 mg; 0.24 mmol; 1.00 eq.) and 2,3,4,6,7,8,9,10-octahydro-pyrimido[1,2-a]azepine (73 mg; 0.48 mmol; 2.00 eq.) in NMP (0.5 ml) was placed in microwave at 140° C. for 10 hr. The crude was purified by prep HPLC to affold the title compound. LC-MS (M+H=512, obsd.=512). $^1$H NMR (400 MHz, DMSO-d6) δ 7.82 (s, 2H), 7.62 (d, J=9.0 Hz, 3H), 7.54 (d, J=9.6 Hz, 5H), 7.07 (t, J=8.9 Hz, 3H), 6.14 (d, J=11.5 Hz, 4H), 5.05 (s, 1H), 4.93 (s, 1H), 4.48 (s, 2H), 4.32 (td, J=13.8, 12.1, 7.8 Hz, 3H), 3.91 (t, J=6.2 Hz, 3H), 3.09 (q, J=7.2 Hz, 7H), 3.03 (t, J=7.0 Hz, 2H), 2.67 (dt, J=28.6, 7.7 Hz, 5H), 2.25 (s, 8H), 1.93 (dp, J=12.7, 6.7 Hz, 5H), 1.86-1.68 (m, 3H), 1.29-1.10 (m, 13H).

4-Amino-6-{(3R,4S)-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carbonitrile (chiral, absolute configuration undetermined) ("40")

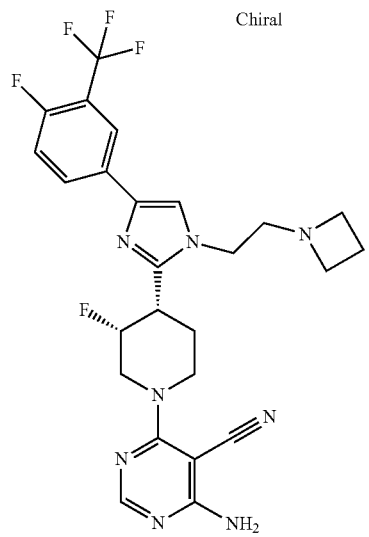 [SMILES: N#Cc1c(N)ncnc1N1CC[C@@H](c2nc(-c3ccc(F)c(C(F)(F)F)c3)cn2CCN2CCC2)[C@@H](F)C1]

The title compound was obtained by SFC chiral separation of racemic 4-amino-6-cis-4-[1-(2-azetidin-1-yl-ethyl)-4-(4-fluoro-3-trifluoromethyl-phenyl)-1H-imidazol-2-yl]-3-fluoro-piperidin-1-yl}-pyrimidine-5-carbonitrile. LC-MS (M+H=533, obsd.=533).

6-{cis-4-[1-Azetidin-3-ylmethyl-4-(4-fluoro-3-methyl-phenyl)-1H-imidazol-2-yl]-3-fluoro-piperidin-1-yl}-5-isopropyl-pyrimidin-4-ylamine (racemic) ("41")

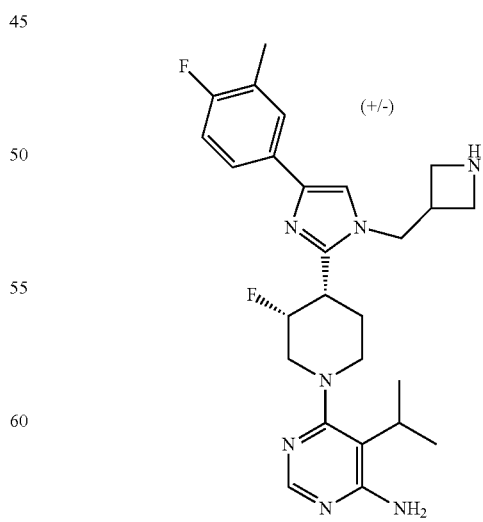

To a solution of racemic cis-3-[4-(4-fluoro-3-methyl-phenyl)-2-(3-fluoro-piperidin-4-yl)-imidazol-1-ylmethyl]- azetidine-1-carboxylic acid tert-butyl ester (62.44 mg; 0.14 mmol; 1.00 eq.) in NMP (0.3 ml), were added 2,3,4,6,7,8,9,10-octahydro-pyrimido[1,2-a]azepine (0.04 ml; 0.28 mmol; 2.00 eq.) and 6-chloro-5-isopropyl-pyrimidin-4-ylamine (24.00 mg; 0.14 mmol; 1.00 eq.). The reaction mixture was placed in microwave at 135° C. for 19 hr. the crude was purified by prep HP LC to yield cis-3-[2-1-(6-Amino-5-isopropyl-pyrimidin-4-yl)-3-fluoro-piperidin-4-yl]-4-(4-fluoro-3-methyl-phenyl)-imidazol-1-ylmethyl]-azetidine-1-carboxylic acid tert-butyl ester. LC-MS (M+H=582, obsd.=582).

To a solution of the above compound in DCM (2 ml), was added trifluoroacetic acid (1 ml). The mixture was stirred at RT for 2 hr. After removal of the solvents the residue was purified by prep HPLC to afford the title compound. LC-MS (M+H=482, obsd.=482). $^1$H NMR (400 MHz, Methanol-d4) δ 8.06 (d, J=4.4 Hz, 1H), 7.63 (d, J=7.9 Hz, 1H), 7.55 (t, J=6.6 Hz, 1H), 7.36 (s, 1H), 7.01 (t, J=9.0 Hz, 1H), 5.01 (s, 1H), 4.41-4.23 (m, 2H), 3.76 (dq, J=30.7, 11.4, 9.6 Hz, 2H), 3.66-3.55 (m, 2H), 3.48 (ddt, J=27.4, 11.3, 5.8 Hz, 3H), 3.27-3.15 (m, 2H), 3.09 (t, J=12.3 Hz, 1H), 2.83 (q, J=13.5, 12.7 Hz, 1H), 1.95-1.86 (m, 1H), 1.38 (dd, J=13.1, 7.2 Hz, 6H).

cis-4-[1-(2-Azetidin-1-yl-ethyl)-4-(4-fluoro-3-trifluoromethyl-phenyl)-1H-imidazol-2-yl]-3-fluoro-piperidin-1-yl}-7H-pyrrolo[2,3-d]pyrimidine-5-carbonitrile (racemic) ("42")

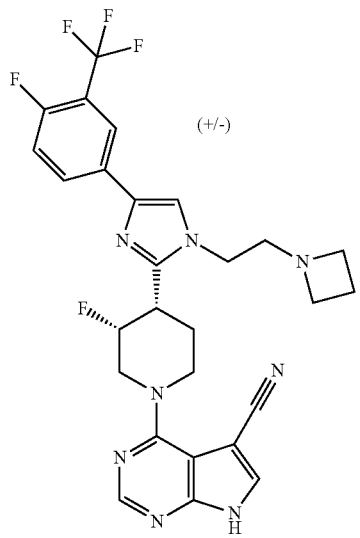 [SMILES: N#Cc1c[nH]c2ncnc(N3CC[C@@H](c4nc(-c5ccc(F)c(C(F)(F)F)c5)cn4CCN4CCC4)[C@@H](F)C3)c12]

A reaction mixture of 4-chloro-7H-pyrrolo[2,3-d]pyrimidine-5-carbonitrile (24.61 mg; 0.14 mmol; 1.02 eq.), cis-4-[1-(2-azetidin-1-yl-ethyl)-4-(4-fluoro-3-trifluoromethyl-phenyl)-1H-imidazol-2-yl]-3-fluoro-piperidine (56.00 mg; 0.14 mmol; 1.00 eq.), and ethyldiisopropylamine (22.70 mg; 0.18 mmol; 1.30 eq.) in ACN (1 ml) was stirred at 50° C. for 36 hr. After cooling to rt, the precipitate was collected by filtration to yield the title compound as a yellow solid. LC-MS (M+H=557, obsd.=557).

cis-4-[1-(2-Azetidin-1-yl-ethyl)-4-(2-trifluoromethyl-pyridin-4-yl)-1H-imidazol-2-yl]-3-fluoro-piperidin-1-yl}-7H-pyrrolo[2,3-d]pyrimidine-5-carbonitrile (racemic) ("43")

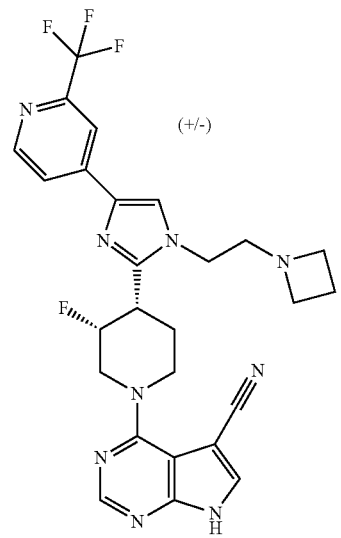 [SMILES: N#Cc1c[nH]c2ncnc(N3CC[C@@H](c4nc(-c5ccnc(C(F)(F)F)c5)cn4CCN4CCC4)[C@@H](F)C3)c12]

The title compound was prepared according to the procedure described for the preparation of compound "42" by using cis-4-[1-(2-azetidin-1-yl-ethyl)-2-(3,4)cis-3-fluoro-piperidin-4-yl)-1H-imidazol-4-yl]-2-trifluoromethyl-pyridine. LC-MS (M+H=540, obsd.=540).

4-Amino-6-{4-[1-(2-azetidin-1-yl-ethyl)-4-(4-fluoro-3-methyl-phenyl)-1H-imidazol-2-yl]-4-hydroxy-piperidin-1-yl}-pyrimidine-5-carbonitrile ("44")

To a solution of 4-[1-(2-azetidin-1-yl-ethyl)-4-(4-fluoro-3-methyl-phenyl)-1H-imidazol-2-yl]-4-(tert-butyl-dimethyl-silanyloxy)-piperidine (100.00 mg; 0.21 mmol; 1.00 eq.) in acetonitrile (2 ml), were added ethy-diisopropylamine (0.06 ml; 0.32 mmol; 1.50 eq.) and then 4-amino-6-chloro-pyrimidine-5-carbonitrile (33 mg, 0.21 mmol, 1.0 eq). The reaction mixture was stirred at RT overnight. After removal of the solvent, the residue was directly used for the next step reaction.

To the above product, was added 2 ml of TBAF (1.0M solution in THF). The resulting mixture was stirred at RT overnight. The crude was purified by prep HPLC to affold the title compound. LC-MS (M+H=515, obsd=515). $^1$H NMR (400 MHz, DMSO-d6) δ 8.06 (s, 1H), 7.67-7.58 (m, 1H), 7.55 (d, J=9.5 Hz, 2H), 7.28 (s, 2H), 7.08 (dd, J=11.7, 6.5 Hz, 1H), 4.32 (dt, J=13.2, 4.0 Hz, 2H), 4.18 (q, J=6.8 Hz, 2H), 3.72-3.53 (m, 2H), 3.23-3.03 (m, 5H), 2.77 (t, J=6.6 Hz, 2H), 2.28-2.23 (m, 3H), 2.23-2.11 (m, 2H), 1.97 (dd, J=10.9, 4.0 Hz, 4H), 1.62-1.47 (m, 1H), 1.32 (h, J=7.3 Hz, 1H), 0.95 (t, J=7.3 Hz, 2H).

1-(6-Amino-5-isopropyl-pyrimidin-4-yl)-4-[1-(2-azetidin-1-yl-ethyl)-4-(4-fluoro-3-methyl-phenyl)-1H-imidazol-2-yl]-piperidin-4-ol ("45")

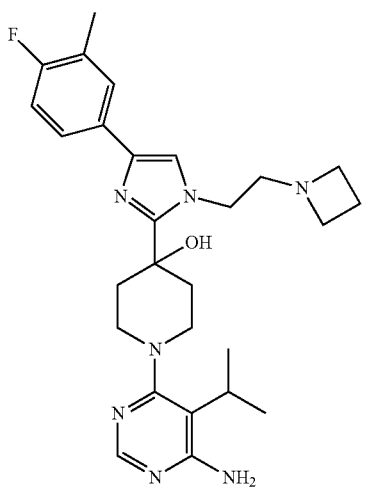 [SMILES: Cc1cc(-c2cn(CCN3CCC3)c(C3(O)CCN(c4ncnc(N)c4C(C)C)CC3)n2)ccc1F]

To a solution of 4-[1-(2-azetidin-1-yl-ethyl)-4-(4-fluoro-3-methyl-phenyl)-1H-imidazol-2-yl]-4-(tert-butyl-dimethyl-silanyloxy)-piperidine (100.00 mg; 0.21 mmol; 1.00 eq.) in DMSO (1 ml), were added 6-chloro-5-isopropyl-pyrimidin-4-ylamine (36.31 mg; 0.21 mmol; 1.00 eq.) and cesiumn carbonate (103.39 mg; 0.32 mmol; 1.50 eq.). The mixture was stirred at 120° C. for 48 h. The crude was purified by HPLC to affold the title compound. LC-MS (M+H=494, obsd=494). $^1$H NMR (400 MHz, DMSO-d6) δ 7.99 (s, 1H), 7.63 (dd, J=7.3, 1.9 Hz, 1H), 7.55 (d, J=4.4 Hz, 2H), 7.08 (dd, J=9.7, 8.5 Hz, 1H), 6.05 (s, 2H), 5.60 (s, 1H), 4.18 (t, J=6.7 Hz, 2H), 3.16 (q, J=7.9, 7.0 Hz, 6H), 2.78-2.69 (m, 2H), 2.26 (d, J=1.8 Hz, 4H), 2.05-1.85 (m, 4H), 1.28 (d, J=7.2 Hz, 6H).

1-(6-Amino-5-ethyl-pyrimidin-4-yl)-4-[1-(2-azetidin-1-yl-ethyl)-4-(4-fluoro-3-methyl-phenyl)-1H-imidazol-2-yl]-piperidin-4-ol ("46")

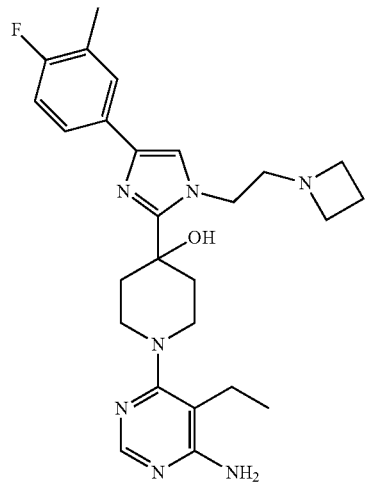

The title compound was prepared according to the procedure described for the preparation of compound "45" by using 4-[1-(2-azetidin-1-yl-ethyl)-4-(4-fluoro-3-methyl-phenyl)-1H-imidazol-2-yl]-4-(tert-butyl-dimethyl-silanyloxy)-piperidine reacted with 6-chloro-5-ethyl-pyrimidin-4-ylamine. LC-MS (M+H=480, obsd=480). $^1$H NMR (400 MHz, DMSO-d6) δ 7.98 (s, 1H), 7.68-7.60 (m, 1H), 7.60-7.47 (m, 2H), 7.08 (dd, J=9.7, 8.5 Hz, 1H), 6.19 (s, 2H), 5.61 (s, 1H), 4.18 (t, J=6.7 Hz, 2H), 3.32-3.19 (m, 4H), 3.15 (t, J=7.0 Hz, 4H), 2.76 (t, J=6.7 Hz, 2H), 2.46 (q, J=7.1 Hz, 2H), 2.31-2.20 (m, 5H), 2.05-1.85 (m, 4H), 1.11 (t, J=7.3 Hz, 3H).

1-(6-Amino-5-chloro-pyrimidin-4-yl)-4-[1-(2-azetidin-1-yl-ethyl)-4-(4-fluoro-3-methyl-phenyl)-1H-imidazol-2-yl]-piperidin-4-ol ("47")

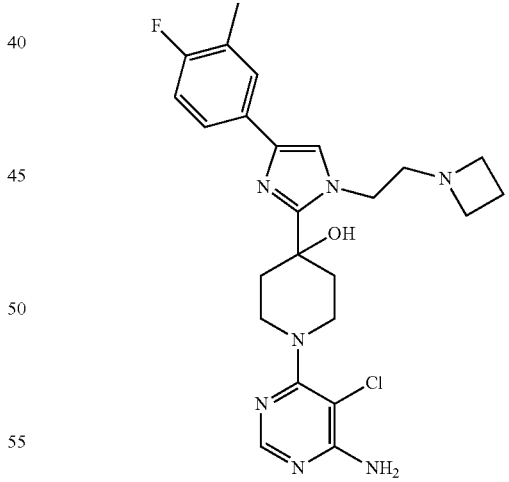

To a solution of 4-[1-(2-azetidin-1-yl-ethyl)-4-(4-fluoro-3-methyl-phenyl)-1H-imidazol-2-yl]-4-(tert-butyl-dimethyl-silanyloxy)-piperidine (100.00 mg; 0.21 mmol; 1.00 eq.) in acetonitrile (2 ml), were added thyldiisopropylamine (0.06 ml; 0.32 mmol; 1.50 eq.), then 5,6-dichloro-pyrimidin-4-ylamine (34.69 mgl; 0.21 mmol; 1.00 eq.). The reaction mixture was stirred 100° C. for 24 hr. The crude was purified by HPLC to affold the title compound. LC-MS (M+H=486, obsd=486). $^1$H NMR (400 MHz, DMSO-d6) δ 7.98 (s, 1H), 7.62 (dd, J=7.7, 2.2 Hz, 1H), 7.59-7.48 (m, 2H), 7.08 (t, J=9.1 Hz, 1H), 6.77 (s, 2H), 4.18 (t, J=6.6 Hz, 2H), 3.84 (dt, J=13.2, 4.1 Hz, 2H), 3.25-3.02 (m, 8H), 2.76 (t, J=6.6 Hz, 2H), 2.30-2.15 (m, 5H), 2.06-1.83 (m, 4H), 1.57 (td, J=10.7, 9.7, 5.9 Hz, 4H), 1.32 (h, J=7.3 Hz, 4H), 0.95 (t, J=7.3 Hz, 5H).

4-Amino-6-{4-{1-(2-azetidin-1-yl-ethyl)-4-(4-fluoro-3-methyl-phenyl)-1H-imidazol-2-yl]-3,3-difluoro-piperidin-1-yl}-pyrimidine-5-carbonitrile ("48")

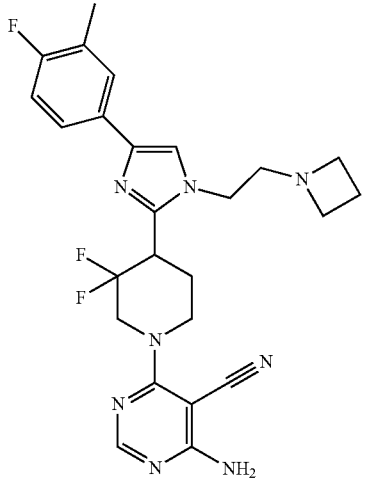 [SMILES: Cc1cc(-c2cn(CCN3CCC3)c(C3CCN(c4ncnc(N)c4C#N)CC3(F)F)n2)ccc1F]

To a solution of 4-[1-(2-azetidin-1-yl-ethyl)-4-(4-fluoro-3-methyl-phenyl)-1H-imidazol-2-yl]-3,3-difluoro-piperidine (140.00 mg; 0.37 mmol; 1.00 eq.) in acetonitrile (3 ml), were added ethyldiisopropylamine (0.10 ml; 0.55 mmol; 1.50 eq.) and 4-amino-6-chloro-pyrimidine-5-carbonitrile (57.18 mg; 0.37 mmol; 1.00 eq.). The mixture was stirred at RT overnight. The crude was purified by prep HPLC to affold the title compound. LC-MS (M+H=497, obsd=497). $^1$H NMR (400 MHz, DMSO-d6) δ 8.12 (d, J=1.3 Hz, 1H), 7.64 (d, J=9.2 Hz, 2H), 7.61-7.51 (m, 1H), 7.45 (d, J=23.3 Hz, 1H), 7.09 (t, J=9.2 Hz, 1H), 4.90-4.71 (m, 1H), 4.58 (d, J=13.8 Hz, 1H), 4.02-3.81 (m, 4H), 3.58 (t, J=12.1 Hz, 1H), 3.12 (dq, J=19.6, 6.8 Hz, 4H), 2.69 (dtd, J=18.1, 12.2, 6.4 Hz, 2H), 2.37 (d, J=11.4 Hz, 1H), 2.25 (s, 3H), 2.06 (d, J=14.1 Hz, 1H), 1.95 (q, J=7.0 Hz, 2H).

4-Amino-6-{4-[1-(2-azetidin-1-yl-ethyl)-4-(4-fluoro-3-methyl-phenyl)-1H-imidazol-2-yl]-3,3-difluoro-piperidin-1-yl}-pyrimidine-5-carboxylic acid amide ("49")

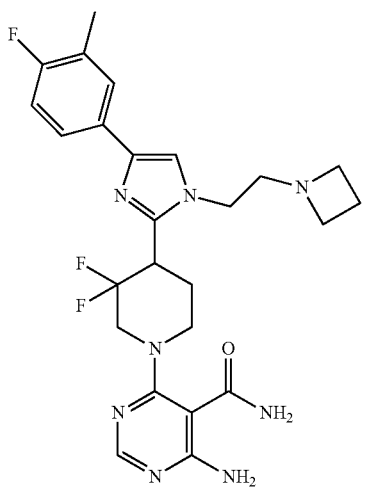 [SMILES: Cc1cc(-c2cn(CCN3CCC3)c(C3CCN(c4ncnc(N)c4C(N)=O)CC3(F)F)n2)ccc1F]

To a reaction mixture of 4-amino-6-{4-[1-(2-azetidin-1-yl-ethyl)-4-(4-fluoro-3-methyl-phenyl)-1H-imidazol-2-yl]-3,3-difluoro-piperidin-1-yl}-pyrimidine-5-carbonitrile (150.00 mg; 0.30 mmol; 1.00 eq.) in DMSO (40 ml) stirred at RT, were added $H_2O_2$ (0.29 ml; 3.02 mmol; 10.00 eq.) and 2.0M NaOH aqueous solution (1.51 ml; 3.02 mmol; 10.00 eq.). The reaction mixture was stirred at RT for 2 hr. The crude was purified by prep-HPLC (basic) to affold the title compound (60 mg). LC-MS (M+H=515, obsd=515). $^1$H NMR (400 MHz, DMSO-d6) δ 8.04 (d, J=1.3 Hz, 2H), 7.63 (t, J=6.9 Hz, 9H), 7.55 (t, J=6.7 Hz, 3H), 7.08 (t, J=9.1 Hz, 2H), 6.87 (s, 4H), 4.22-3.99 (m, 5H), 3.99-3.87 (m, 4H), 3.81 (ddt, J=21.1, 10.5, 5.7 Hz, 1H), 3.64 (dd, J=25.7, 13.4 Hz, 2H), 3.11 (dq, J=19.1, 6.8 Hz, 9H), 2.80-2.58 (m, 4H), 2.35 (d, J=11.4 Hz, 2H), 2.31 (s, OH), 2.25 (s, 5H), 1.95 (p, J=7.0 Hz, 6H).

6-{4-[1-(2-Azetidin-1-yl-ethyl)-4-(4-fluoro-3-methyl-phenyl)-1H-imidazol-2-yl]-3,3-difluoro-piperidin-1-yl}-5-isopropyl-pyrimidin-4-ylamine ("50")

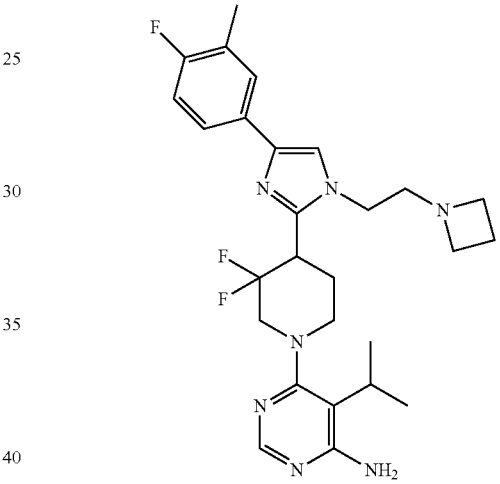

A reaction mixture of 6-chloro-5-isopropyl-pyrimidin-4-ylamine (55.00 mg; 0.32 mmol; 1.00 eq.), 4-[1-(2-azetidin-1-yl-ethyl)-4-(4-fluoro-3-methyl-phenyl)-1H-imidazol-2-yl]-3,3-difluoro-piperidine (121.27 mg; 0.32 mmol; 1.00 eq.), 2,3,4,6,7,8,9,10-octahydro-pyrimido[1,2-a]azepine (0.09 ml; 0.64 mmol; 2.00 eq.) and NMP (0.4 ml) in a 5 ml microwave tube was placed in microwave at 135° C. for 10 hr. The crude was purified by prep HPLC to affold the title compound. LC-MS (M+H=514, obsd=514). $^1$H NMR (400 MHz, DMSO-d6) δ 8.12-8.02 (m, 1H), 7.71-7.49 (m, 3H), 7.10 (t, J=9.3 Hz, 1H), 6.30 (s, 2H), 3.92 (d, J=7.3 Hz, 2H), 3.71 (d, J=22.8 Hz, 1H), 3.51 (d, J=10.8 Hz, 1H), 3.16-3.03 (m, 4H), 2.96 (t, J=11.5 Hz, 1H), 2.75-2.57 (m, 3H), 2.27 (s, 3H), 2.04-1.84 (m, 3H), 1.29 (dd, J=23.7, 7.2 Hz, 6H).

Biological Activity

P70S6K Enzyme Assay

P70S6K inhibitor compounds were diluted and plated in 96 well plates. A reaction mixture including the following components was then added to the compound plate to initiate the enzyme reaction; P70S6K (3 nM, T412E mutant, Millipore) was mixed with 24 μM ATP in an assay buffer containing 100 mM Hepes (pH 7.5), 5 mM MgCl2, 1 mM DTT, 0.015% Brij and 1 μM of the substrate peptide FITC-AHA-AKRRRLSSLRA-OH (derived from the S6 ribosomal protein sequence, FITC=fluorescein isothiocyanate, AHA=6-aminohexanoic acid). The reaction was incubated for 90 min at 25° C., before the addition of 10 mM EDTA to stop the reaction. The proportion of substrate and product (phosphorylated) peptide was analysed on a Caliper Life Sciences Lab Chip 3000, using a pressure of −1.4 psi, and upstream and downstream voltages of −3000 and −700 respectively. Product peaks were resolved before substrate peaks on the resulting chromatograms.

AKT Enzyme Assay

A TTP Mosquito liquid handling instrument was used to place 125 nl of the appropriate concentration of inhibitor in 100% DMSO (for a dose response curve calculation) into each well of a 384-well plate. To this reaction components were added to a final volume of 12.5 µl:

0.1 ng/µl His-AKT (Full Length), (Invitrogen, Part # P2999, Lot #641228C).
160 uM ATP (Fluka, 02055)
1 mM DTT (Sigma, D0632)
1 mM MgCl2 (Sigma, M1028)
1 µM substrate peptide (sequence FITC-AHA-GRPRTSS-FAEG-NH2), synthesized by Tufts Peptide Synthesis service.
100 mM HEPES pH 7.5 (Calbiochem, 391338)
0.015% Brij-35 (Sigma, B4184)

The reaction was incubated for 90 min at 25 C., and then stopped by the addition of 70 µl of Stop buffer (100 mM HEPES pH 7.5, 0.015% Brij-35, 10 mM EDTA (Sigma, E7889)).

The plate was read on a Caliper LC 3000 in an Off-Chip mobility shift assay format, using the following parameters for a 12-sipper chip: screening pressure −2.3 psi, upstream voltage −500, and downstream voltage −3000. These conditions caused unphosphorylated substrate and phosphorylated product peptide to resolve as separate peaks allowing direct measurement of percentage of conversion of substrate to product.

The percent conversion was plotted against concentration of inhibitor to produce a sigmoidal dose response curve, from which an IC50 was calculated.

The values for the p70S6K and AKT enzyme inhibition assay for the compounds set out in the Experimental section are presented in Table 4.

TABLE 4 p70S6K and AKT Enzyme Inhibition by Compound Described by Formula (I)

| Compound No. | IC$_{50}$ p70S6K (nM) | IC$_{50}$ AKT (nM) |
|---|---|---|
| 1 | +++ | +++ |
| 2 | +++ | +++ |
| 3 | ++ | ++ |
| 4 | ++ | + |
| 5 | ++ | + |
| 6 | + | + |
| 7 | ++ | + |
| 8 | ++ | + |
| 9 | ++ | ++ |
| 10 | +++ | +++ |
| 11 | ++ | ++ |
| 12 | ++ | ++ |
| 13 | ++ | ++ |
| 14 | ++ | ++ |
| 15 | ++ | + |
| 16 | ++ | ++ |
| 17 | ++ | + |
| 18 | ++ | ++ |
| 19 | ++ | ++ |
| 20 | ++ | ++ |

TABLE 4-continued p70S6K and AKT Enzyme Inhibition by Compound Described by Formula (I)

| Compound No. | IC$_{50}$ p70S6K (nM) | IC$_{50}$ AKT (nM) |
|---|---|---|
| 21 | ++ | + |
| 22 | ++ | ++ |
| 23 | ++ | ++ |
| 24 | ++ | ++ |
| 25 | ++ | ++ |
| 26 | ++ | + |
| 27 | ++ | ++ |
| 28 | + | + |
| 29 | ++ | ++ |
| 30 | ++ | + |
| 31 | ++ | + |
| 32 | ++ | ++ |
| 33 | ++ | ++ |
| 34 | ++ | + |
| 35 | ++ | ++ |
| 36 | ++ | ++ |
| 37 | ++ | ++ |
| 38 | ++ | ++ |
| 39 | ++ | ++ |
| 40 | ++ | ++ |
| 41 | ++ | ++ |
| 42 | ++ | ++ |
| 43 | ++ | ++ |
| 44 | ++ | ++ |
| 45 | ++ | ++ |
| 46 | ++ | ++ |
| 47 | ++ | ++ |
| 48 | ++ | ++ |
| 49 | + | + |
| 50 | ++ | ++ |

+++ <1 nM
++ 1-10 nM
+ >10 nM

All patents, patent application, patent publications, non-patent publications, and any other reference cited herein are hereby incorporated by reference.

We claim:

1. A compound of Formula (I)

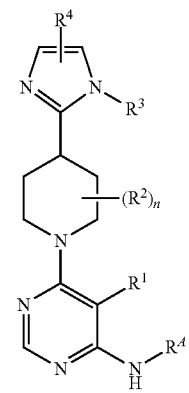

wherein:
R$^A$ and R$^1$, together with the atoms to which each is attached, forms a 5-membered monocyclic heteroaryl ring having 1 nitrogen; which is optionally substituted;
each R$^2$ is independently Hal or A;
A is unbranched or branched alkyl group having 1, 2, 3, 4, 5 of 6 C atoms in which 1-4 H atoms can be replaced, independently of each other, by Hal;

R³ an unbranched or branched linear or mono- or bicyclic alkyl group having 1, 2, 3, 4, 5, 6, 7, 8 or 9 C atoms, in which one or two CH₂ groups may be replaced by an —O— or —NH— group, and/or in which one or two CH groups may be replaced by —N— and/or in which 1, 2 or 3 H atoms may be replaced by Hal or OH; or R³ is unbranched or branched alkyl group having 1, 2, 3, 4, 5 of 6 C atoms, which is substituted by a 3-6 membered heterocyclic ring, which may be further optionally substituted;

R⁴ is $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is mono-, di- or trisubstituted by Hal, LA, OH, O(LA), NH₂ and/or NH(LA), N(LA)₂, NO₂, CN, OCN, COOH, COO(LA), CONH₂, CONH(LA), CON(LA)₂, NHCO(LA), NHCONH(LA), NHCONH₂, NHSO₂(LA), CHO or CO(LA);

LA is an unbranched or branched, saturated or partially unsaturated, linear hydrocarbon chain having 1, 2, 3 or 4 C atoms, wherein 1, 2 or 3 H atoms may be replaced by Hal;

Hal is F, Cl, Br or I; and n is 1 or 2;

or a pharmaceutically acceptable salt thereof.

2. The compound of claim 1 wherein each R² is independently Hal, methyl, ethyl, n-propyl, i-propyl, n-butyl, s-butyl, t-butyl, straight chain or branched pentyl, or straight chain or branched hexyl.

3. The compound of claim 2 wherein each R² is independently F, or methyl.

4. The compound of claim 1, wherein R³ is selected from Table 2:

TABLE 2

Substituents for R³ in Formula (I):

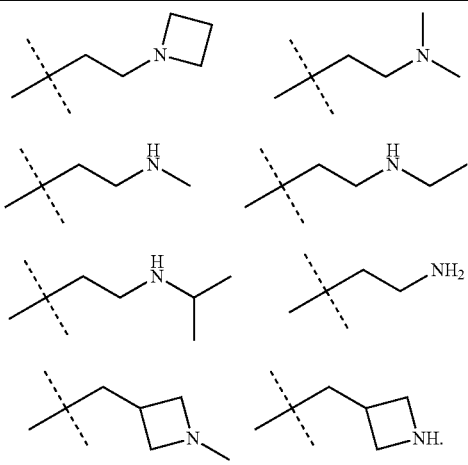

5. The compound of claim 1, wherein R⁴ is $C_{5-10}$ aryl or a 5-6 membered monocyclic heteroaryl ring having 1-4 heteroatoms independently selected from nitrogen, oxygen, or sulfur; each of which is mono-, di- or trisubstituted by Hal, LA, OH, O(LA), NH₂ and/or NH(LA), N(LA)₂, NO₂, CN, OCN, COOH, COO(LA), CONH₂, CONH(LA), CON(LA)₂, NHCO(LA), NHCONH(LA), NHCONH₂, NHSO₂(LA), CHO or CO(LA).

6. The compound of claim 5, wherein R⁴ is selected from Table 3.

TABLE 3

Substituents for R⁴ in Formula (I):

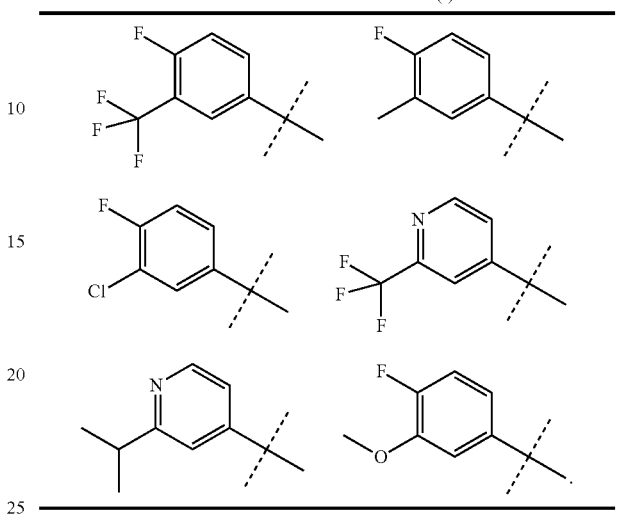

7. The compound of claim 1, of formula (V):

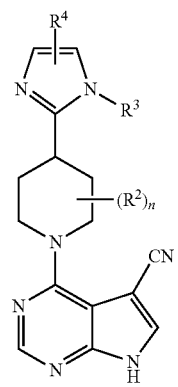

(V)

or a pharmaceutically acceptable salt thereof.

8. A compound according to claim 1, selected from the group consisting of:

cis-4-[1-(2-Azetidin-1-yl-ethyl)-4-(4-fluoro-3-trifluoromethyl-phenyl)-1H-imidazol-2-yl]-3-fluoro-piperidin-1-yl}-7H-pyrrolo[2,3-d]pyrimidine-5-carbonitrile (racemic) ("42"); and cis-4-[1-(2-Azetidin-1-yl-ethyl)-4-(2-trifluoromethyl-pyridin-4-yl)-1H-imidazol-2-yl]-3-fluoro-piperidin-1-yl}-7H-pyrrolo[2,3-d]pyrimidine-5-carbonitrile (racemic) ("43");

and pharmaceutically acceptable salts, thereof.

9. A pharmaceutical composition comprising a compound according to claim 1, or a pharmaceutically acceptable salt, or solvate thereof, as active ingredient, together with a pharmaceutically acceptable carrier.

10. A method for treating cancer, comprising administering to a subject a compound of claim 1, or a pharmaceutically acceptable salt, or solvate thereof.

11. The method of claim 10, wherein said cancer is selected from the group consisting of brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma and Kaposi's sarcoma.

12. A kit comprising separate packs of:
   a) an effective amount of a compound according to claim 1 or a pharmaceutically acceptable salt, or solvate thereof, and
   b) an effective amount of a further medicament active ingredient.

* * * * *